(12) United States Patent
Winzer et al.

(10) Patent No.: US 10,006,010 B2
(45) Date of Patent: Jun. 26, 2018

(54) CYTOCHROME P450 FUSION PROTEIN

(71) Applicants: The University of York, York (GB); Sun Pharmaceutical Industries (Australia) Pty Ltd, Notting Hill, Victoria (AU)

(72) Inventors: Thilo Winzer, York (GB); Ian Graham, York (GB); Tracy Carol Walker, Latrobe (AU)

(73) Assignees: The University of York, York (GB); Sun Pharmaceutical Industries (Australia) Pty Ltd, Notting Hill, Victoria (AU)

( * ) Notice: Subject to any disclaimer, the term of this patent is extended or adjusted under 35 U.S.C. 154(b) by 5 days.

(21) Appl. No.: 15/304,455

(22) PCT Filed: May 15, 2015

(86) PCT No.: PCT/GB2015/051446
§ 371 (c)(1),
(2) Date: Oct. 14, 2016

(87) PCT Pub. No.: WO2015/173590
PCT Pub. Date: Nov. 19, 2015

(65) Prior Publication Data
US 2017/0058267 A1   Mar. 2, 2017

(30) Foreign Application Priority Data

May 16, 2014 (GB) .................................. 1408729.0
Apr. 22, 2015 (GB) .................................. 1506805.9

(51) Int. Cl.
*C12N 9/02* (2006.01)
*C12P 17/12* (2006.01)
*C12N 15/82* (2006.01)

(52) U.S. Cl.
CPC .......... *C12N 9/0071* (2013.01); *C12N 9/0004* (2013.01); *C12N 9/0077* (2013.01); *C12N 15/8243* (2013.01); *C12P 17/12* (2013.01); *C07K 2319/00* (2013.01)

(58) Field of Classification Search
None
See application file for complete search history.

(56) References Cited

FOREIGN PATENT DOCUMENTS

| WO | WO 00/58333 A1 | 10/2000 |
|---|---|---|
| WO | WO 2013/136057 A2 * | 9/2013 |
| WO | WO 2015/021561 A1 | 2/2015 |
| WO | WO 2015/081437 A1 | 6/2015 |

OTHER PUBLICATIONS

Farrow et al., 2015, Nature Chemical Biology 11: 728-732.*
Farrow et al., "Stereochemical inversion of (S)-reticuline by a cytochrome P450 fusion in opium poppy," *Nat Chem Biol.* 11:728-732, 2015.
Accession No. B9VRJ6, Database UniProt [Online], Mar. 24, 2009.
Accession No. FJ596168, Database EMBL [Online], Feb. 3, 2009.
Allen et al., "RNAi-Mediated Replacement of Morphine With the Nonnarcotic Alkaloid Reticuline in Opium Poppy," *Nat Biotechnol.* 22:1559-1566, 2004.
De-Eknamkul and Zenk, "Purification and Properties of 1,2-Dehydroreticuline Reductase from *Papaver somniferum* Seedlings," *Phytochemistry* 31:813-821, 1992.
Hirata et al., "1,2-Dehydroreticuline Synthase, the Branch Point Enzyme Opening the Morphinan Biosynthetic Pathway," *Phytochemistry* 65:1039-1046, 2004.
PCT/GB2015/051446 International Search Report and Written Opinion dated Sep. 14, 2015 (14 pages).

* cited by examiner

*Primary Examiner* — Amjad A Abraham
*Assistant Examiner* — Bratislav Stankovic
(74) *Attorney, Agent, or Firm* — Klarquist Sparkman, LLP

(57) ABSTRACT

This disclosure relates to the isolation of a nucleic acid molecule[s] that encode a novel cytochrome P450 and an oxidoreductase from a *Papaver somniferum* [*P. somniferum*] cultivar, transgenic cells transformed with said nucleic acid molecule and sequence variants thereof; and including methods for the production of intermediates in the production of morphinans.

19 Claims, 6 Drawing Sheets

FIG. 5C
FIG. 5D
FIG. 5E
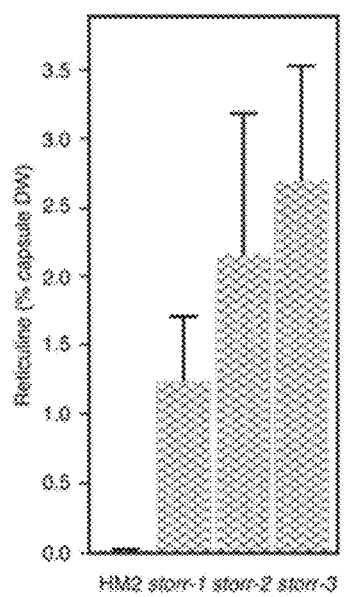
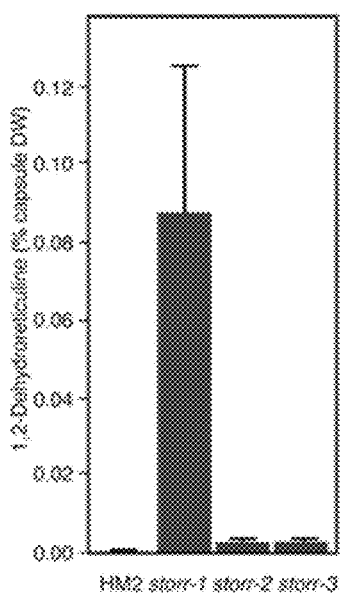
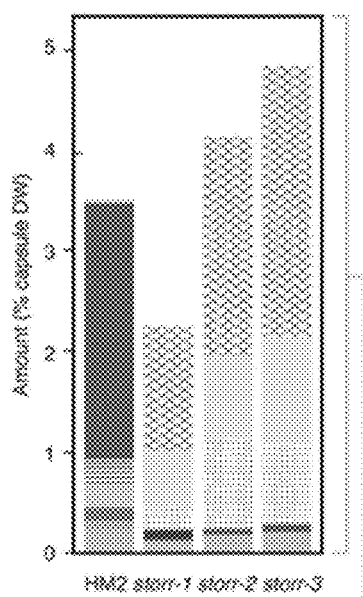
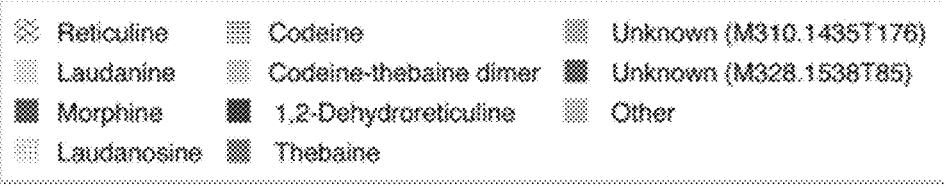

SEQUENCE LISTING

<160> NUMBER OF SEQ ID NOS: 51

<210> SEQ ID NO 1
<211> LENGTH: 901
<212> TYPE: PRT
<213> ORGANISM: Papaver somniferum

<400> SEQUENCE: 1

```
Met Glu Leu Gln Tyr Ile Ser Tyr Phe Gln Pro Thr Ser Ser Val Val
1               5                   10                  15

Ala Leu Leu Leu Ala Leu Val Ser Ile Leu Ser Ser Val Val Val Leu
            20                  25                  30

Arg Lys Thr Phe Leu Asn Asn Tyr Ser Ser Ser Pro Ala Ser Ser Thr
        35                  40                  45

Lys Thr Ala Val Leu Ser His Gln Arg Gln Gln Ser Cys Ala Leu Pro
    50                  55                  60

Ile Ser Gly Leu Leu His Ile Phe Met Asn Lys Asn Gly Leu Ile His
65                  70                  75                  80

Val Thr Leu Gly Asn Met Ala Asp Lys Tyr Gly Pro Ile Phe Ser Phe
                85                  90                  95

Pro Thr Gly Ser His Arg Thr Leu Val Val Ser Ser Trp Glu Met Val
            100                 105                 110

Lys Glu Cys Phe Thr Gly Asn Asn Asp Thr Ala Phe Ser Asn Arg Pro
        115                 120                 125

Ile Pro Leu Ala Phe Lys Thr Ile Phe Tyr Ala Cys Gly Gly Ile Asp
    130                 135                 140

Ser Tyr Gly Leu Ser Ser Val Pro Tyr Gly Lys Tyr Trp Arg Glu Leu
145                 150                 155                 160

Arg Lys Val Cys Val His Asn Leu Leu Ser Asn Gln Gln Leu Leu Lys
                165                 170                 175

Phe Arg His Leu Ile Ile Ser Gln Val Asp Thr Ser Phe Asn Lys Leu
            180                 185                 190

Tyr Glu Leu Cys Lys Asn Ser Glu Asp Asn His Gly Asn Tyr Thr Thr
        195                 200                 205

Thr Thr Thr Thr Ala Ala Gly Met Val Arg Ile Asp Asp Trp Leu Ala
```

-continued

```
            210                 215                 220
Glu Leu Ser Phe Asn Val Ile Gly Arg Ile Val Cys Gly Phe Gln Ser
225                 230                 235                 240

Gly Pro Lys Thr Gly Ala Pro Ser Arg Val Glu Gln Phe Lys Glu Ala
                245                 250                 255

Ile Asn Glu Ala Ser Tyr Phe Met Ser Thr Ser Pro Val Ser Asp Asn
                260                 265                 270

Val Pro Met Leu Gly Trp Ile Asp Gln Leu Thr Gly Leu Thr Arg Asn
            275                 280                 285

Met Lys His Cys Gly Lys Lys Leu Asp Leu Val Val Glu Ser Ile Ile
            290                 295                 300

Asn Asp His Arg Gln Lys Arg Arg Phe Ser Arg Thr Lys Gly Gly Asp
305                 310                 315                 320

Glu Lys Asp Asp Glu Gln Asp Asp Phe Ile Asp Ile Cys Leu Ser Ile
                325                 330                 335

Met Glu Gln Pro Gln Leu Pro Gly Asn Asn Asn Pro Ser Gln Ile Pro
                340                 345                 350

Ile Lys Ser Ile Val Leu Asp Met Ile Gly Gly Thr Asp Thr Thr
            355                 360                 365

Lys Leu Thr Thr Ile Trp Thr Leu Ser Leu Leu Asn Asn Pro His
            370                 375                 380

Val Leu Asp Lys Ala Lys Gln Glu Val Asp Ala His Phe Arg Thr Lys
385                 390                 395                 400

Arg Arg Ser Thr Asn Asp Ala Ala Ala Val Val Asp Phe Asp Asp
                405                 410                 415

Ile Arg Asn Leu Val Tyr Ile Gln Ala Ile Ile Lys Glu Ser Met Arg
                420                 425                 430

Leu Tyr Pro Ala Ser Pro Val Val Glu Arg Leu Ser Gly Glu Asp Cys
                435                 440                 445

Val Val Gly Gly Phe His Val Pro Ala Gly Thr Arg Leu Trp Ala Asn
            450                 455                 460

Val Trp Lys Met Gln Arg Asp Pro Lys Val Trp Asp Pro Leu Val
465                 470                 475                 480

Phe Arg Pro Asp Arg Phe Leu Ser Asp Glu Gln Lys Met Val Asp Val
                485                 490                 495

Arg Gly Gln Asn Tyr Glu Leu Leu Pro Phe Gly Ala Gly Arg Arg Val
                500                 505                 510

Cys Pro Gly Val Ser Phe Ser Leu Asp Leu Met Gln Leu Val Leu Thr
            515                 520                 525

Arg Leu Ile Leu Glu Phe Glu Met Lys Ser Pro Ser Gly Lys Val Asp
530                 535                 540

Met Thr Ala Thr Pro Gly Leu Met Ser Tyr Lys Val Ile Pro Leu Asp
545                 550                 555                 560

Ile Leu Leu Thr His Arg Arg Ile Lys Pro Cys Val Gln Ser Ala Ala
                565                 570                 575

Ser Glu Arg Asp Met Glu Ser Ser Gly Val Pro Val Ile Thr Leu Gly
                580                 585                 590

Ser Gly Lys Val Met Pro Val Leu Gly Met Gly Thr Phe Glu Lys Val
            595                 600                 605

Gly Lys Gly Ser Glu Arg Glu Arg Leu Ala Ile Leu Lys Ala Ile Glu
            610                 615                 620

Val Gly Tyr Arg Tyr Phe Asp Thr Ala Ala Ala Tyr Glu Thr Glu Glu
625                 630                 635                 640
```

```
Val Leu Gly Glu Ala Ile Ala Glu Ala Leu Gln Leu Gly Leu Val Lys
                645                 650                 655

Ser Arg Asp Glu Leu Phe Ile Ser Ser Met Leu Trp Cys Thr Asp Ala
            660                 665                 670

His Ala Asp Arg Val Leu Leu Ala Leu Gln Asn Ser Leu Arg Asn Leu
        675                 680                 685

Lys Leu Glu Tyr Val Asp Leu Tyr Met Leu Pro Phe Pro Ala Ser Leu
    690                 695                 700

Lys Pro Gly Lys Ile Thr Met Asp Ile Pro Glu Glu Asp Ile Cys Arg
705                 710                 715                 720

Met Asp Tyr Arg Ser Val Trp Ala Ala Met Glu Glu Cys Gln Asn Leu
                725                 730                 735

Gly Phe Thr Lys Ser Ile Gly Val Ser Asn Phe Ser Cys Lys Lys Leu
            740                 745                 750

Gln Glu Leu Met Ala Thr Ala Asn Ile Pro Pro Ala Val Asn Gln Val
        755                 760                 765

Glu Met Ser Pro Ala Phe Gln Gln Lys Lys Leu Arg Glu Tyr Cys Asn
    770                 775                 780

Ala Asn Asn Ile Leu Val Ser Ala Ile Ser Val Leu Gly Ser Asn Gly
785                 790                 795                 800

Thr Pro Trp Gly Ser Asn Ala Val Leu Gly Ser Glu Val Leu Lys Lys
                805                 810                 815

Ile Ala Met Ala Lys Gly Lys Ser Val Ala Gln Val Ser Met Arg Trp
            820                 825                 830

Val Tyr Glu Gln Gly Ala Ser Leu Val Val Lys Ser Phe Ser Glu Glu
    835                 840                 845

Arg Leu Arg Glu Asn Leu Asn Ile Phe Asp Trp Glu Leu Thr Lys Glu
    850                 855                 860

Asp His Glu Lys Ile Gly Glu Ile Pro Gln Cys Arg Ile Leu Ser Ala
865                 870                 875                 880

Tyr Phe Leu Val Ser Pro Asn Gly Pro Phe Lys Ser Gln Glu Glu Leu
                885                 890                 895

Trp Asp Asp Glu Ala
            900

<210> SEQ ID NO 2
<211> LENGTH: 580
<212> TYPE: PRT
<213> ORGANISM: Papaver somniferum

<400> SEQUENCE: 2

Met Glu Leu Gln Tyr Ile Ser Tyr Phe Gln Pro Thr Ser Ser Val Val
1               5                   10                  15

Ala Leu Leu Leu Ala Leu Val Ser Ile Leu Ser Ser Val Val Val Leu
            20                  25                  30

Arg Lys Thr Phe Leu Asn Asn Tyr Ser Ser Ser Pro Ala Ser Ser Thr
        35                  40                  45

Lys Thr Ala Val Leu Ser His Gln Arg Gln Gln Ser Cys Ala Leu Pro
    50                  55                  60

Ile Ser Gly Leu Leu His Ile Phe Met Asn Lys Asn Gly Leu Ile His
65                  70                  75                  80

Val Thr Leu Gly Asn Met Ala Asp Lys Tyr Gly Pro Ile Phe Ser Phe
                85                  90                  95

Pro Thr Gly Ser His Arg Thr Leu Val Val Ser Ser Trp Glu Met Val
```

-continued

```
                100                 105                 110
Lys Glu Cys Phe Thr Gly Asn Asn Asp Thr Ala Phe Ser Asn Arg Pro
            115                 120                 125

Ile Pro Leu Ala Phe Lys Thr Ile Phe Tyr Ala Cys Gly Gly Ile Asp
        130                 135                 140

Ser Tyr Gly Leu Ser Ser Val Pro Tyr Gly Lys Tyr Trp Arg Glu Leu
145                 150                 155                 160

Arg Lys Val Cys Val His Asn Leu Leu Ser Asn Gln Gln Leu Leu Lys
                165                 170                 175

Phe Arg His Leu Ile Ile Ser Gln Val Asp Thr Ser Phe Asn Lys Leu
            180                 185                 190

Tyr Glu Leu Cys Lys Asn Ser Glu Asp Asn His Gly Asn Tyr Thr Thr
        195                 200                 205

Thr Thr Thr Thr Ala Ala Gly Met Val Arg Ile Asp Asp Trp Leu Ala
210                 215                 220

Glu Leu Ser Phe Asn Val Ile Gly Arg Ile Val Cys Gly Phe Gln Ser
225                 230                 235                 240

Gly Pro Lys Thr Gly Ala Pro Ser Arg Val Glu Gln Phe Lys Glu Ala
                245                 250                 255

Ile Asn Glu Ala Ser Tyr Phe Met Ser Thr Ser Pro Val Ser Asp Asn
            260                 265                 270

Val Pro Met Leu Gly Trp Ile Asp Gln Leu Thr Gly Leu Thr Arg Asn
        275                 280                 285

Met Lys His Cys Gly Lys Lys Leu Asp Leu Val Val Glu Ser Ile Ile
        290                 295                 300

Asn Asp His Arg Gln Lys Arg Arg Phe Ser Arg Thr Lys Gly Gly Asp
305                 310                 315                 320

Glu Lys Asp Asp Glu Gln Asp Asp Phe Ile Asp Ile Cys Leu Ser Ile
                325                 330                 335

Met Glu Gln Pro Gln Leu Pro Gly Asn Asn Asn Pro Ser Gln Ile Pro
            340                 345                 350

Ile Lys Ser Ile Val Leu Asp Met Ile Gly Gly Gly Thr Asp Thr Thr
        355                 360                 365

Lys Leu Thr Thr Ile Trp Thr Leu Ser Leu Leu Leu Asn Asn Pro His
        370                 375                 380

Val Leu Asp Lys Ala Lys Gln Glu Val Asp Ala His Phe Arg Thr Lys
385                 390                 395                 400

Arg Arg Ser Thr Asn Asp Ala Ala Ala Ala Val Val Asp Phe Asp Asp
                405                 410                 415

Ile Arg Asn Leu Val Tyr Ile Gln Ala Ile Ile Lys Glu Ser Met Arg
            420                 425                 430

Leu Tyr Pro Ala Ser Pro Val Val Glu Arg Leu Ser Gly Glu Asp Cys
        435                 440                 445

Val Val Gly Gly Phe His Val Pro Ala Gly Thr Arg Leu Trp Ala Asn
        450                 455                 460

Val Trp Lys Met Gln Arg Asp Pro Lys Val Trp Asp Pro Leu Val
465                 470                 475                 480

Phe Arg Pro Asp Arg Phe Leu Ser Asp Glu Gln Lys Met Val Asp Val
                485                 490                 495

Arg Gly Gln Asn Tyr Glu Leu Leu Pro Phe Gly Ala Gly Arg Arg Val
            500                 505                 510

Cys Pro Gly Val Ser Phe Ser Leu Asp Leu Met Gln Leu Val Leu Thr
        515                 520                 525
```

```
Arg Leu Ile Leu Glu Phe Glu Met Lys Ser Pro Ser Gly Lys Val Asp
    530                 535                 540

Met Thr Ala Thr Pro Gly Leu Met Ser Tyr Lys Val Ile Pro Leu Asp
545                 550                 555                 560

Ile Leu Leu Thr His Arg Arg Ile Lys Pro Cys Val Gln Ser Ala Ala
                565                 570                 575

Ser Glu Arg Asp
            580

<210> SEQ ID NO 3
<211> LENGTH: 321
<212> TYPE: PRT
<213> ORGANISM: Papaver somniferum

<400> SEQUENCE: 3

Met Glu Ser Ser Gly Val Pro Val Ile Thr Leu Gly Ser Gly Lys Val
1               5                   10                  15

Met Pro Val Leu Gly Met Gly Thr Phe Glu Lys Val Gly Lys Gly Ser
                20                  25                  30

Glu Arg Glu Arg Leu Ala Ile Leu Lys Ala Ile Glu Val Gly Tyr Arg
            35                  40                  45

Tyr Phe Asp Thr Ala Ala Ala Tyr Glu Thr Glu Glu Val Leu Gly Glu
        50                  55                  60

Ala Ile Ala Glu Ala Leu Gln Leu Gly Leu Val Lys Ser Arg Asp Glu
65                  70                  75                  80

Leu Phe Ile Ser Ser Met Leu Trp Cys Thr Asp Ala His Ala Asp Arg
                85                  90                  95

Val Leu Leu Ala Leu Gln Asn Ser Leu Arg Asn Leu Lys Leu Glu Tyr
            100                 105                 110

Val Asp Leu Tyr Met Leu Pro Phe Pro Ala Ser Leu Lys Pro Gly Lys
        115                 120                 125

Ile Thr Met Asp Ile Pro Glu Glu Asp Ile Cys Arg Met Asp Tyr Arg
130                 135                 140

Ser Val Trp Ala Ala Met Glu Glu Cys Gln Asn Leu Gly Phe Thr Lys
145                 150                 155                 160

Ser Ile Gly Val Ser Asn Phe Ser Cys Lys Lys Leu Gln Glu Leu Met
                165                 170                 175

Ala Thr Ala Asn Ile Pro Pro Ala Val Asn Gln Val Glu Met Ser Pro
            180                 185                 190

Ala Phe Gln Gln Lys Leu Arg Glu Tyr Cys Asn Ala Asn Asn Ile
        195                 200                 205

Leu Val Ser Ala Ile Ser Val Leu Gly Ser Asn Gly Thr Pro Trp Gly
210                 215                 220

Ser Asn Ala Val Leu Gly Ser Glu Val Leu Lys Lys Ile Ala Met Ala
225                 230                 235                 240

Lys Gly Lys Ser Val Ala Gln Val Ser Met Arg Trp Val Tyr Glu Gln
                245                 250                 255

Gly Ala Ser Leu Val Val Lys Ser Phe Ser Glu Glu Arg Leu Arg Glu
            260                 265                 270

Asn Leu Asn Ile Phe Asp Trp Glu Leu Thr Lys Glu Asp His Glu Lys
        275                 280                 285

Ile Gly Glu Ile Pro Gln Cys Arg Ile Leu Ser Ala Tyr Phe Leu Val
290                 295                 300

Ser Pro Asn Gly Pro Phe Lys Ser Gln Glu Glu Leu Trp Asp Asp Glu
```

Ala

<210> SEQ ID NO 4
<211> LENGTH: 2830
<212> TYPE: DNA
<213> ORGANISM: Papaver somniferum

<400> SEQUENCE: 4

```
atggagctcc aatatatttc ttattttcaa ccaacttcct ccgttgttgc tcttctactt      60
gctcttgtat ccatcttatc cagtgtcgtt gttttgagga agacattttt gaataactac     120
tcatcatcac ctgcatcatc cacaaaaaca gcggtacttt ctcatcagcg gcagcagtcg     180
tgtgcattgc caatttccgg tctcctccat atttttcatga ataaaaacgg cttaattcat     240
gtaactcttg gaaatatggc tgataaatac ggtccgattt cagtttccc aacaggtagc      300
catagaactc tcgttgtgag cagttgggag atggtaaaag agtgttttac tggcaacaat     360
gacactgctt tctcaaaccg tcctatcccg ttagctttta agactatatt ctatgcatgc     420
ggtggcatag actcatacgg tcttttcgagt gtaccttatg gaaaatattg gagggagctt    480
cgaaaggtct gtgtgcataa cctcctgtct aatcaacaac tactcaagtt cagacacttg     540
ataatttctc aagtcgatac gtcttttcaat aagctgtatg agttatgcaa aaactctgaa    600
gacaaccatg gaaactatac tactactact actaccgcag ctggcatggt gagaatcgat     660
gattggctcg ccgaattatc gttcaatgtg ataggaagaa tagtctgcgg attccaatca     720
ggccctaaga caggtgctcc aagcaggggtg gaacaattta agaagcaat taatgaagca     780
tcttatttta tgtcgacatc tccagtgtca gataatgttc caatgctagg gtggattgac    840
caattgacag gtcttacgag aaatatgaag cactgcggaa agaaattaga cttggtggtc    900
gagagcataa ttaatgatca tcgtcaaaag agacgattct ctagaactaa aggaggagat    960
gagaaggacg atgaacaaga tgacttcatc gacatttgtt tgtcaataat ggagcaacca   1020
cagcttcctg caacaataa tccttctcag atacctatca aatctattgt cctggacatg   1080
ataggtgggg gcactgacac cacaaaaactg accaccatct ggaccctttc cttgctgctg   1140
aacaaccccc atgtgttgga caaggcaaaa caagaagtgg atgcacactt tcgaaccaaa   1200
aggagatcaa caaatgatgc agcagcagcc gtggtggatt ttgatgatat tcgtaacctt   1260
gtctacatcc aggcaatcat caaagaatca atgcggttgt atccagccag ccccgtggtg   1320
gagcgactga gcggcgaaga ttgtgtggtc ggtgggtttc atgtaccagc agggacgaga   1380
ttatgggcta acgtatggaa gatgcaacga ccctaaag tatgggatga tccattggtg      1440
tttcgaccag acagattttt gagcgatgaa cagaagatgg ttgatgtaag gggtcaaaat   1500
tatgagctgt taccatttgg agccggtcga cgtgtatgtc caggtgtatc cttctctttg   1560
gatctaatgc aactggtact gactcgtctt attctcgagt ttgaaatgaa gtctcctagc   1620
gggaaagtgg acatgacagc aacaccagga ttaatgagtt acaaggtgat cccccttgac   1680
attctgctca cccatcgtcg cataaagccg tgtgtgcagt cagcagcctc tgagagagac   1740
atggagagta tggtgtacc agtaatcact ctgggctcgg gcaaggtgat gcctgttctt    1800
ggcatgggaa catttgagaa agttggtaaa gggtccgaaa gagagaggtt ggcgatttta   1860
aaagcgatag aggtgggtta cagatacttc gatacagctg ctgcatacga aactgaagag   1920
gttcttggag aagctattgc tgaagcactt caacttggcc tagtcaaatc tcgagatgaa   1980
cttttcatca gttccatgct ctggtgcact gatgctcacg ctgatcgtgt cctcctcgct   2040
```

-continued

```
cttcagaatt cgctgaggaa tcttaaattg gagtatgtgg atctatatat gttacccttc    2100
ccggcaagct tgaagcctgg gaagataacg atggacatac cagaggaaga tatttgtcgc    2160
atggactaca ggtctgtatg ggcagccatg gaagagtgtc aaaaccttgg cttcactaaa    2220
tcaatcggtg ttagcaattt ctcctgcaaa aagcttcagg aattgatggc gactgccaac    2280
atccctccag ctgtgaatca agtggagatg agcccggctt ccaacaaaa gaagctgaga    2340 gagtattgca acgcaaataa tatattagtc agtgcaatct ctgtactggg atcaaacgga    2400
accccatggg gctccaatgc agttttgggt tctgaggtgc ttaagaaaat tgctatggcc    2460
aaaggaaaat ctgttgctca ggttagtatg agatgggttt acgagcaagg cgcgagtctt    2520
gtggtaaaaa gtttcagtga agagagattg agggaaaact tgaacatatt tgactgggaa    2580
ctcactaagg aagaccatga aaagatcggt gagattccac agtgcagaat cttgagtgct    2640
tattttttgg tctcacctaa tggaccttc aaatctcaag aagagttgtg ggatgatgaa    2700
gcttgaaaca tcgatcactt aactctagac atgcatttat aagagaagct tccccctgctg    2760 tgtgctcaat cttgatttat tttatcaaat tacatcttgc tataagggag tcacggatct    2820
cattcccttc                                                           2830
```

<210> SEQ ID NO 5
<211> LENGTH: 1740
<212> TYPE: DNA
<213> ORGANISM: Papaver somniferum

<400> SEQUENCE: 5

```
atggagctcc aatatatttc ttattttcaa ccaacttcct ccgttgttgc tcttctactt      60
gctcttgtat ccatcttatc cagtgtcgtt gttttgagga agacattttt gaataactac    120
tcatcatcac ctgcatcatc cacaaaaaca gcggtacttt ctcatcagcg gcagcagtcg    180
tgtgcattgc caatttccgg tctcctccat attttcatga ataaaaacgg cttaattcat    240
gtaactcttg gaaatatggc tgataaatac ggtccgattt cagtttccc aacaggtagc    300 catagaactc tcgttgtgag cagttgggag atggtaaaag agtgttttac tggcaacaat    360
gacactgctt tctcaaaccg tcctatcccg ttagctttta agactatatt ctatgcatgc    420
ggtggcatag actcatacgg tcttctcgagt gtaccttatg gaaaatattg gagggagctt    480
cgaaaggtct gtgtgcataa cctcctgtct aatcaacaac tactcaagtt cagacacttg    540
ataatttctc aagtcgatac gtctttcaat aagctgtatg agttatgcaa aaactctgaa    600
gacaaccatg gaaactatac tactactact actaccgcag ctggcatggt gagaatcgat    660
gattggctcg ccgaattatc gttcaatgtg ataggaagaa tagtctgcgg attccaatca    720
ggccctaaga caggtgctcc aagcagggtg gaacaattta agaagcaat taatgaagca    780 tcttatttta tgtcgacatc tccagtgtca gataatgttc caatgctagg gtggattgac    840
caattgacag gtcttacgag aaatatgaag cactgcggaa agaaattaga cttggtggtc    900
gagagcataa ttaatgatca tcgtcaaaag agacgattct ctagaactaa aggaggagat    960
gagaaggacg atgaacaaga tgacttcatc gacatttgtt tgtcaataat ggagcaacca   1020
cagcttcctg gcaacaataa tccttctcag ataccatca aatctattgt cctggacatg   1080
ataggtgggg gcactgacac cacaaaactg accaccatct ggaccctttc cttgctgctg   1140 aacaacccc atgtgttgga caaggcaaaa caagaagtgg atgcacactt tcgaaccaaa   1200
aggagatcaa caaatgatgc agcagcagcc gtggtgaatt ttgatgatat tcgtaacctt   1260
```

```
gtctacatcc aggcaatcat caaagaatca atgcggttgt atccagccag ccccgtggtg    1320
gagcgactga gcggcgaaga ttgtgtggtc ggtgggtttc atgtaccagc agggacgaga    1380
ttatgggcta acgtatggaa gatgcaacga accctaaag tatgggatga tccattggtg     1440
tttcgaccag acagatttt gagcgatgaa cagaagatgg ttgatgtaag gggtcaaaat    1500
tatgagctgt taccatttgg agccggtcga cgtgtatgtc caggtgtatc cttctctttg    1560
gatctaatgc aactggtact gactcgtctt attctcgagt ttgaaatgaa gtctcctagc    1620
gggaaagtgg acatgacagc aacaccagga ttaatgagtt acaaggtgat ccccttgac    1680 attctgctca cccatcgtcg cataaagccg tgtgtgcagt cagcagcctc tgagagagac    1740
```

<210> SEQ ID NO 6
<211> LENGTH: 1090
<212> TYPE: DNA
<213> ORGANISM: Papaver somniferum

<400> SEQUENCE: 6

```
atggagagta gtggtgtacc agtaatcact ctgggctcgg gcaaggtgat gcctgttctt     60
ggcatgggaa catttgagaa agttggtaaa gggtccgaaa gagagaggtt ggcgatttta    120
aaagcgatag aggtgggtta cagatacttc gatacagctg ctgcatacga aactgaagag    180
gttcttggag aagctattgc tgaagcactt caacttggcc tagtcaaatc tcgagatgaa    240
cttttcatca gttccatgct ctggtgcact gatgctcacg ctgatcgtgt cctcctcgct    300
cttcagaatt cgctgaggaa tcttaaattg gagtatgtgg atctatatat gttacccttc    360
ccggcaagct tgaagcctgg gaagataacg atggacatac cagaggaaga tatttgtcgc    420
atggactaca ggtctgtatg ggcagccatg aagagtgtc aaaaccttgg cttcactaaa    480
tcaatcggtg ttagcaattt ctcctgcaaa aagcttcagg aattgatggc gactgccaac    540
atccctccag ctgtgaatca agtggagatg agcccggctt ccaacaaaa gaagctgaga    600 gagtattgca acgcaaataa tatattagtc agtgcaatct ctgtactggg atcaaacgga    660
accccatggg gctccaatgc agttttgggt tctgaggtgc ttaagaaaat tgctatggcc    720
aaaggaaaat ctgttgctca ggttagtatg agatgggttt acgagcaagg cgcgagtctt    780
gtggtaaaaa gtttcagtga agagagattg agggaaaact tgaacatatt tgactgggaa    840
ctcactaagg aagaccatga aaagatcggt gagattccac agtgcagaat cttgagtgct    900
tatttttggg tctcacctaa tggacctttc aaatctcaag aagagttgtg ggatgatgaa    960
gcttgaaaca tcgatcactt aactctagac atgcatttat aagagaagct tcccctgctg    1020
tgtgctcaat cttgattta tttatcaaat tacatcttgc tataagggag tcacggatct    1080
cattcccttc                                                             1090
```

<210> SEQ ID NO 7
<211> LENGTH: 12
<212> TYPE: PRT
<213> ORGANISM: artificial sequence
<220> FEATURE:
<223> OTHER INFORMATION: Linker linking SEQ ID2 and 3

<400> SEQUENCE: 7

```
Lys Pro Cys Val Gln Ser Ala Ala Ser Glu Arg Asp
1               5                   10
```

<210> SEQ ID NO 8
<211> LENGTH: 36
<212> TYPE: DNA

<213> ORGANISM: artificial sequence
<220> FEATURE:
<223> OTHER INFORMATION: Linker linking SEQ ID 5 and 6

<400> SEQUENCE: 8
aagccgtgtg tgcagtcagc agcctctgag agagac                                36

<210> SEQ ID NO 9
<211> LENGTH: 1483
<212> TYPE: DNA
<213> ORGANISM: Papaver somniferum

<400> SEQUENCE: 9
gccgtgtgtg cagtcagcag cctctgagag agacatggag agtagtggtg taccagtaat      60
tactctgagc tcgggcaagt tgatgcctgt tctgggcatg ggaacatttg agaaagttgg     120
taaagggtcc gaaagagaga ggttggtgat tttaaaagcg atagaggtgg gttacagata     180
cttcgataca gctgctgcat acgaaactga agaggttctt ggagaagcta ttgctgaagc     240
actccaactt ggcctaatca atctcgaga tgaacttttc atcagttcca tgctctggtg      300
cactgatgct catcctgatc gtgtcctcct cgctcttcag aattctctga ggtaaacttt     360
tttgatgcaa attaggctta tatatatatg tgcaaagcct ttgcacatac cagtaggtac     420
acttaaaaca tctatcatat tttagataaa tgaaattgtt ttgtgtgata tagccatata     480
ggaatcttaa attggagtat ctggatctat atatgttacc cttcccggta agcttgaagc     540
cagggaagat aacgatggac atacaagagg aagatatttg tcgcatggac tacaggtctg     600
tatgggcagc catggaagag tgtcagaacc ttggcttcac taaatcaatc ggtgttagta     660
atttctcctg caaaaagctt caggaattga tggcgaccgc caacatccct ccagatgtga     720
atcaagtgag tactcttact tgaaagtttt gataaaacat cggaagattt ctaatgctta     780
ttaaatttcc aacattatgc ataatactac tactctttat aatgttgatt aaggtggaga     840
tgagcccggc tttccaacaa agaagctga gagattattg caacgcaaat aatatactag      900
tcagtgcagt ctctatactg ggatcaaacg gaaccccatg gggctccaat gcagttttgg     960
gttctgaggt gcttaggaaa attgctatgg ccaaaggaaa atctgttgct caggttggtc    1020
aaattctctg catatgccat agtgtggtct ctgttctttg gcatcgtatt tgcatcacat    1080
tgtattcctt ccttacacgg aatgtaactt acatttgtat tgcgtactga tcaggttagt    1140
atgagatggg tttacgatca aggcgcgagt cttgtggtaa aaagtttcag tgaagagaga    1200
ttgagggaaa acttgaacat atttgactgg gaactcacta aggaagacca tgaaaagatc    1260
ggtgagattc cacagtgcag aatcttgagt gcttattttt tggtctcacc taatggacct    1320
ttcaaatctc aagaagagtt gtgggatgac gaagcttgaa acatcgatca tttaactcta    1380
gacatgcatt tataaaagaa gcttcccctg ctgtgtgctc aatcttgatt tattttatca    1440
aattacatct ggctataagg aagtcacgga tctcattccc ttc                       1483

<210> SEQ ID NO 10
<211> LENGTH: 966
<212> TYPE: DNA
<213> ORGANISM: Papaver somniferum

<400> SEQUENCE: 10
atggagagta gtggtgtacc agtaattact ctgagctcgg gcaagttgat gcctgttctg      60
ggcatgggaa catttgagaa agttggtaaa gggtccgaaa gagagaggtt ggtgatttta     120
aaagcgatag aggtgggtta cagatacttc gatacagctg ctgcatacga aactgaagag     180

-continued

```
gttcttggag aagctattgc tgaagcactc caacttggcc taatcaaatc tcgagatgaa    240
cttttcatca gttccatgct ctggtgcact gatgctcatc ctgatcgtgt cctcctcgct    300
cttcagaatt ctctgaggaa tcttaaattg gagtatctgg atctatatat gttacccttc    360
ccggtaagct tgaagccagg gaagataacg atggacatac aagaggaaga tatttgtcgc    420
atggactaca ggtctgtatg ggcagccatg gaagagtgtc agaaccttgg cttcactaaa    480
tcaatcggtg ttagtaattt ctcctgcaaa aagcttcagg aattgatggc gaccgccaac    540
atccctccag atgtgaatca agtggagatg agcccggctt ccaacaaaa gaagctgaga    600
gattattgca acgcaaataa tatactagtc agtgcagtct ctatactggg atcaaacgga    660
accccatggg gctccaatgc agttttgggt tctgaggtgc ttaggaaaat tgctatggcc    720
aaaggaaaat ctgttgctca ggttagtatg agatgggttt acgatcaagg cgcgagtctt    780
gtggtaaaaa gtttcagtga agagagattg agggaaaact tgaacatatt tgactgggaa    840
ctcactaagg aagaccatga aaagatcggt gagattccac agtgcagaat cttgagtgct    900
tatttttggg tctcacctaa tggacctttc aaatctcaag aagagttgtg ggatgacgaa    960
gcttga                                                               966
```

<210> SEQ ID NO 11
<211> LENGTH: 321
<212> TYPE: PRT
<213> ORGANISM: Papaver somniferum

<400> SEQUENCE: 11

```
Met Glu Ser Ser Gly Val Pro Val Ile Thr Leu Ser Ser Gly Lys Leu
1               5                   10                  15

Met Pro Val Leu Gly Met Gly Thr Phe Glu Lys Val Gly Lys Gly Ser
            20                  25                  30

Glu Arg Glu Arg Leu Val Ile Leu Lys Ala Ile Glu Val Gly Tyr Arg
        35                  40                  45

Tyr Phe Asp Thr Ala Ala Tyr Glu Thr Glu Val Leu Gly Glu
    50                  55                  60

Ala Ile Ala Glu Ala Leu Gln Leu Gly Leu Ile Lys Ser Arg Asp Glu
65                  70                  75                  80

Leu Phe Ile Ser Ser Met Leu Trp Cys Thr Asp Ala His Pro Asp Arg
                85                  90                  95

Val Leu Leu Ala Leu Gln Asn Ser Leu Arg Asn Leu Lys Leu Glu Tyr
            100                 105                 110

Leu Asp Leu Tyr Met Leu Pro Phe Pro Val Ser Leu Lys Pro Gly Lys
        115                 120                 125

Ile Thr Met Asp Ile Gln Glu Glu Asp Ile Cys Arg Met Asp Tyr Arg
    130                 135                 140

Ser Val Trp Ala Ala Met Glu Glu Cys Gln Asn Leu Gly Phe Thr Lys
145                 150                 155                 160

Ser Ile Gly Val Ser Asn Phe Ser Cys Lys Lys Leu Gln Glu Leu Met
                165                 170                 175

Ala Thr Ala Asn Ile Pro Pro Asp Val Asn Gln Val Glu Met Ser Pro
            180                 185                 190

Ala Phe Gln Gln Lys Lys Leu Arg Asp Tyr Cys Asn Ala Asn Asn Ile
        195                 200                 205

Leu Val Ser Ala Val Ser Ile Leu Gly Ser Asn Gly Thr Pro Trp Gly
    210                 215                 220
```

-continued

Ser Asn Ala Val Leu Gly Ser Glu Val Leu Arg Lys Ile Ala Met Ala
225                 230                 235                 240

Lys Gly Lys Ser Val Ala Gln Val Ser Met Arg Trp Val Tyr Asp Gln
            245                 250                 255

Gly Ala Ser Leu Val Val Lys Ser Phe Ser Glu Glu Arg Leu Arg Glu
            260                 265                 270

Asn Leu Asn Ile Phe Asp Trp Glu Leu Thr Lys Glu Asp His Glu Lys
        275                 280                 285

Ile Gly Glu Ile Pro Gln Cys Arg Ile Leu Ser Ala Tyr Phe Leu Val
    290                 295                 300

Ser Pro Asn Gly Pro Phe Lys Ser Gln Glu Glu Leu Trp Asp Asp Glu
305                 310                 315                 320

Ala

<210> SEQ ID NO 12
<211> LENGTH: 39
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(39)
<223> OTHER INFORMATION: R = A or G, V = A, C or G; N = A/T or C/G

<400> SEQUENCE: 12
attctagatc cracatgttt tttttttttt tttttttvn                          39

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
gggttgaatc atggagctc                                                19

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
gaagggaatg agatccgtga c                                             21

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
gccgtgtgtg cagtcagcag                                               20

<210> SEQ ID NO 16
<211> LENGTH: 21
<212> TYPE: DNA
<213> ORGANISM: Artificial Sequence
<220> FEATURE:
<223> OTHER INFORMATION: Primer

```
<400> SEQUENCE: 16
gaagggaatg agatccgtga c                                              21

<210> SEQ ID NO 17
<211> LENGTH: 101
<212> TYPE: DNA
<213> ORGANISM: Papaver somniferum
<220> FEATURE:
<221> NAME/KEY: misc_feature
<222> LOCATION: (1)..(101)
<223> OTHER INFORMATION: n is either G or A

<400> SEQUENCE: 17
tggcctagtc aaatctcgag atgaactttt catcagttcc atgctctgnt gcactgatgc    60
tcacgctgat cgtgtcctcc tcgctcttca gaattcgctg a                       101

<210> SEQ ID NO 18
<211> LENGTH: 201
<212> TYPE: DNA
<213> ORGANISM: Papaver somniferum
<220> FEATURE:
<221> NAME/KEY: misc_feature
<222> LOCATION: (1)..(201)
<223> OTHER INFORMATION: n is either G or A

<400> SEQUENCE: 18
tgctccaagc agggtggaac aatttaaaga agcaattaat gaagcatctt attttatgtc    60
gacatctcca gtgtcagata atgttccaat gctagggtgn attgaccaat tgacaggtct   120
tacgagaaat atgaagcact gcggaaagaa attagacttg gtggtcgaga gcataattaa   180
tgatcatcgt caaaagagac g                                            201

<210> SEQ ID NO 19
<211> LENGTH: 217
<212> TYPE: DNA
<213> ORGANISM: Papaver somniferum
<220> FEATURE:
<221> NAME/KEY: misc_feature
<222> LOCATION: (1)..(217)
<223> OTHER INFORMATION: n is either G or A

<400> SEQUENCE: 19
gtgtatcctt ctctttggat ctaatgcaac tggtactgac tcgtcttatt ctcgagtttg    60
aaatgaagtc tcctagcggg aaagtggaca tgacagcaac accangatta atgagttaca   120
aggtgatccc ccttgacatt ctgctcaccc atcgtcgcat aaagccgtgt gtgcagtcag   180
cagcctctga gagagacatg gagagtagtg gtgtacc                           217

<210> SEQ ID NO 20
<211> LENGTH: 22
<212> TYPE: DNA
<213> ORGANISM: Artificial sequence
<220> FEATURE:
<223> OTHER INFORMATION: Primer

<400> SEQUENCE: 20
atcagcgtga gcatcagtgc ac                                             22

<210> SEQ ID NO 21
<211> LENGTH: 23
<212> TYPE: DNA
<213> ORGANISM: Artificial sequence
<220> FEATURE:
```

```
<223> OTHER INFORMATION: Primer

<400> SEQUENCE: 21
gatcagcgtg agcatcagtg cat                                             23

<210> SEQ ID NO 22
<211> LENGTH: 29
<212> TYPE: DNA
<213> ORGANISM: Artificial sequence
<220> FEATURE:
<223> OTHER INFORMATION: Primer

<400> SEQUENCE: 22
tctcgagatg aactttcat cagttccat                                        29

<210> SEQ ID NO 23
<211> LENGTH: 25
<212> TYPE: DNA
<213> ORGANISM: Artificial sequence
<220> FEATURE:
<223> OTHER INFORMATION: Primer

<400> SEQUENCE: 23
cgtaagacct gtcaattggt caatc                                           25

<210> SEQ ID NO 24
<211> LENGTH: 25
<212> TYPE: DNA
<213> ORGANISM: Artificial sequence
<220> FEATURE:
<223> OTHER INFORMATION: Primer

<400> SEQUENCE: 24
cgtaagacct gtcaattggt caatt                                           25

<210> SEQ ID NO 25
<211> LENGTH: 28
<212> TYPE: DNA
<213> ORGANISM: Artificial sequence
<220> FEATURE:
<223> OTHER INFORMATION: Primer

<400> SEQUENCE: 25
tccagtgtca gataatgttc caatgcta                                        28

<210> SEQ ID NO 26
<211> LENGTH: 22
<212> TYPE: DNA
<213> ORGANISM: Artificial sequence
<220> FEATURE:
<223> OTHER INFORMATION: Primer

<400> SEQUENCE: 26
gtggacatga cagcaacacc ag                                              22

<210> SEQ ID NO 27
<211> LENGTH: 25
<212> TYPE: DNA
<213> ORGANISM: Artificial sequence
<220> FEATURE:
<223> OTHER INFORMATION: Primer

<400> SEQUENCE: 27
aaagtggaca tgacagcaac accaa                                           25
```

<210> SEQ ID NO 28
<211> LENGTH: 25
<212> TYPE: DNA
<213> ORGANISM: Artificial sequence
<220> FEATURE:
<223> OTHER INFORMATION: Primer

<400> SEQUENCE: 28

```
caaggggat caccttgtaa ctcat                                   25
```

<210> SEQ ID NO 29
<211> LENGTH: 2706
<212> TYPE: DNA
<213> ORGANISM: papaver somniferum

<400> SEQUENCE: 29

```
atggagctcc aatatatttc ttattttcaa ccaacttcct ccgttgttgc tcttctactt    60
gctcttgtat ccatcttatc cagtgtcgtt gttttgagga agacattttt gaataactac   120
tcatcatcac ctgcatcatc cacaaaaaca gcggtacttt ctcatcagcg gcagcagtcg   180
tgtgcattgc caatttccgg tctcctccat attttcatga ataaaaacgg cttaattcat   240
gtaactcttg gaaatatggc tgataaatac ggtccgattt tcagtttccc aacaggtagc   300
catagaactc tcgttgtgag cagttgggag atggtaaaag agtgttttac tggcaacaat   360
gacactgctt tctcaaaccg tcctatcccg ttagctttta agactatatt ctatgcatgc   420
ggtggcatag actcatacgg tctttcgagt gtaccttatg aaaatattg gagggagctt   480
cgaaaggtct gtgtgcataa cctcctgtct aatcaacaac tactcaagtt cagacacttg   540
ataatttctc aagtcgatac gtctttcaat aagctgtatg agttatgcaa aaactctgaa   600
gacaaccatg gaaactatac tactactact actaccgcag ctggcatggt gagaatcgat   660
gattggctcg ccgaattatc gttcaatgtg ataggaagaa tagtctgcgg attccaatca   720
ggccctaaga caggtgctcc aagcaggtg gaacaattta agaagcaat taatgaagca   780
tcttatttta tgtcgacatc tccagtgtca gataatgttc caatgctagg gtggattgac   840
caattgacag gtcttacgag aaatatgaag cactgcggaa agaaattaga cttggtggtc   900
gagagcataa ttaatgatca tcgtcaaaag agacgattct ctagaactaa aggaggagat   960
gagaaggacg atgaacaaga tgacttcatc gacatttgtt tgtcaataat ggagcaacca  1020
cagcttcctg gcaacaataa tccttctcag atacctatca aatctattgt cctggacatg  1080
ataggtgggg gcactgacac cacaaaactg accaccatct ggaccctttc cttgctgctg  1140
aacaacccc atgtgttgga caaggcaaaa caagaagtgg atgcacactt cgaaccaaa  1200
aggagatcaa caaatgatgc agcagcagcc gtggtggatt ttgatgatat tcgtaacctt  1260
gtctacatcc aggcaatcat caaagaatca atgcggttgt atccagccag ccccgtggtg  1320
gagcgactga gcggcgaaga ttgtgtggtc ggtgggtttc atgtaccagc agggacgaga  1380
ttatgggcta acgtatggaa gatgcaacga gaccctaaag tatgggatga tccattggtg  1440
tttcgaccag acagattttt gagcgatgaa cagaagatgg ttgatgtaag gggtcaaaat  1500
tatgagctgt taccatttgg agccggtcga cgtgtatgtc caggtgtatc cttctctttg  1560
gatctaatgc aactggtact gactcgtctt attctcgagt ttgaaatgaa gtctcctagc  1620
gggaaagtgg acatgacagc aacaccagga ttaatgagtt acaaggtgat ccccttgac  1680
attctgctca cccatcgtcg cataaagccg tgtgtgcagt cagcagcctc tgagagagac  1740
atggagagta gtggtgtacc agtaatcact ctgggctcgg gcaaggtgat gcctgttctt  1800
```

```
ggcatgggaa catttgagaa agttggtaaa gggtccgaaa gagagaggtt ggcgattta      1860 aaagcgatag aggtgggtta cagatacttc gatacagctg ctgcatacga aactgaagag      1920
gttcttggag aagctattgc tgaagcactt caacttggcc tagtcaaatc tcgagatgaa      1980
cttttcatca gttccatgct ctggtgcact gatgctcacg ctgatcgtgt cctcctcgct      2040
cttcagaatt cgctgaggaa tcttaaattg gagtatgtgg atctatatat gttacccttc      2100
ccggcaagct tgaagcctgg gaagataacg atggacatac cagaggaaga tatttgtcgc      2160
atggactaca ggtctgtatg ggcagccatg gaagagtgtc aaaaccttgg cttcactaaa      2220
tcaatcggtg ttagcaattt ctcctgcaaa aagcttcagg aattgatggc gactgccaac      2280
atccctccag ctgtgaatca agtggagatg agcccggctt ccaacaaaa gaagctgaga      2340 gagtattgca acgcaaataa tatattagtc agtgcaatct ctgtactggg atcaaacgga      2400
accccatggg gctccaatgc agttttgggt tctgaggtgc ttaagaaaat tgctatggcc      2460
aaaggaaaat ctgttgctca ggttagtatg agatgggttt acgagcaagg cgcgagtctt      2520
gtggtaaaaa gtttcagtga agagagattg agggaaaact tgaacatatt tgactgggaa      2580
ctcactaagg aagaccatga aaagatcggt gagattccac agtgcagaat cttgagtgct      2640 tatttttttgg tctcacctaa tggaccttc aaatctcaag aagagttgtg ggatgatgaa      2700
gcttga                                                                 2706
```

<210> SEQ ID NO 30
<211> LENGTH: 2052
<212> TYPE: DNA
<213> ORGANISM: Artificial Sequence
<220> FEATURE:
<223> OTHER INFORMATION: Yeast codon optimised PsCPR

<400> SEQUENCE: 30

```
atgggttcaa caaacttagc caactcaata gaatcaatgt taggtatctc aataggttca       60
gaatacatct ccgatccaat ctttatcatg gtcactacag ttgcttccat gttaattggt      120
tttggtttct ttgcatgtat gaaatcttca tccagtcaat ctaagccaat cgaaacttac      180
aagcctatca tcgacaagga agaagaagaa atcgaagttg atccaggtaa attaaattg      240 acaatctttt tcggtacaca aaccggtact gcagaaggtt ttgccaaagc tttggcagaa      300
gaaattaaag caaagtacaa aaaggccgtt gtaaaggtcg ttgatttgga tgactatgct      360
gcagaagatg accaatacga agaaagttg aaaaggaat ctttggtttt ctttatggta      420
gctacatatg gtgacggtga acctaccgat aatgccgcta gatttttacaa gtggttcaca      480 caagaacatg aacgtggtga atggttgcaa caattaacct atggtgtttt tggtttgggt      540
aacagacaat acgaacactt caacaaaatt gcagtcgacg ttgatgaaca attgggtaaa      600
caaggtgcta agagaatagt acaagtcggt ttaggtgacg acgatcaatg tatcgaagac      660 gatttttactg cttggagaga attgttgtgg acagaattgg atcaattgtt gaaggacgaa      720
gatgcagccc catctgttgc taccccttat attgcaactg taccagaata cagagtagtc      780
atacatgaaa ccactgttgc tgcattggac gataaacaca ttaatactgc caacggtgac      840
gttgctttcg atatcttgca tccatgtaga acaatcgtag ctcaacaaag agaattgcat      900
aagcctaaga gtgatagatc ttgcatccac ttggaattcg atatctctgg ttcttcattg      960
acatacgaaa ccggtgacca tgttggtgta tacgccgaaa actgtgatga acccgttgaa      1020
gaagctggta aattgttggg tcaaccattg gatttgttat tttcaataca cacagacaag      1080
gaagatggtt ccctcaagg ttccagtttg ccacctccat tccctggtcc atgcactttg      1140
```

```
agatctgcct tagctagata tgcagatttg ttaaatcctc caagaaaagc ttcattgata    1200
gcattatccg cacatgcctc agttccatcc gaagctgaaa gattgagatt tttatcttca    1260
cctttgggta aaacgaata ctctaagtgg gttgtaggta gtcaaagatc tttgttagaa     1320
atcatggcag aattcccatc agccaaacct ccattgggtg ttttctttgc cgctgtagct    1380
cctagattac ctccaagata ttactccatc tccagttctc caagtttgc acctagtaga     1440 attcatgtca catgtgcctt ggtttatggt caatctccaa ccggtagagt ccatagaggt    1500
gtttgctcaa cttggatgaa acacgccgtc ccacaagata gttgggctcc tatattcgtt    1560
agaacttcta acttcaagtt gcctgctgat ccatcaaccc ctatcattat ggttggtcca    1620
ggtactggtt tagcaccttt tagaggtttc ttgcaagaaa aatggccctt aaaagaaaac    1680
ggtgctcaat tgggtccagc agtttttattt ttcggttgta gaaacagaaa catggacttc    1740
atctatgaag atgaattgaa caacttcgta gaaagaggtg tcattagtga attagttata    1800
gcattttcta gagaaggtga aaagaaagaa tacgttcaac ataagatgat ggaaaaggct    1860
acagacgtat ggaatgtcat ctctggtgac ggttatttgt acgtatgcgg tgacgccaag    1920
ggtatggcta gagatgtcca tagaactta cacacaattg ctcaagaaca aggtccaatg     1980
gaatcatccg cagccgaagc tgcagttaag aaattgcaag tcgaagaaag atatttgaga    2040
gatgtttggt aa                                                         2052

<210> SEQ ID NO 31
<211> LENGTH: 2706
<212> TYPE: DNA
<213> ORGANISM: Artificial Sequence
<220> FEATURE:
<223> OTHER INFORMATION: Yeast Codon optimized STORR (CYP82Y2)

<400> SEQUENCE: 31
atggaattac aatacatctc ctactttcaa ccaacctctt cagtcgtcgc tttgttatta     60
gcattagtct ctatcttatc ctccgtagtt gtattgagaa agacattttt gaacaactac    120
tcttcatccc cagccagttc tacaaagacc gctgtttgt cacatcaaag acaacaatcc     180
tgtgctttgc ctatcagtgg tttgttgcat atattcatga acaaaaacgg tttgatccac    240
gttacattgg gtaatatggc tgataagtac ggtccaatct ttagtttccc tacaggttct    300
cacagaacct tggtcgtttc atcctgggaa atggttaagg aatgcttcac tggtaacaac    360
gatacagctt tctcaaatag accaatacct ttagccttta agactatctt ctatgcttgt    420
ggtggtattg attcctacgg tttgagttct gttccatacg gtaaatactg gagagaattg    480
agaaaggtct gcgttcataa cttgttgtct aaccaacaat tgttgaagtt tagacacttg    540
attatatcac aagttgacac atccttcaac aaattgtacg aattgtgtaa gaactctgaa    600
gataaccatg gtaactacac tacaaccact acaaccgctg ctggtatggt tagaattgat    660
gactggttgg ctgaattgtc ttttaatgtt atcggtagaa tcgtatgcgg tttccaatca    720
ggtccaaaaa ctggtgcacc ttccagagtt gaacaattca agaagcaat taacgaagcc    780 agttatttca tgtcaacatc cccagtctct gacaatgttc ctatgttagg ttggattgat    840
caattgaccg gtttgactag aaacatgaag cattgtggta aaaagttgga cttggtagtc    900
gaatcaatca ttaatgatca cagacaaaag agaagatttt ccagaactaa aggtggtgac    960
gaaaaggatg acgaacaaga tgacttcatc gatatctgct tgtcaatcat ggaacaacca   1020
caattacctg gtaacaacaa cccatctcaa atccctatta aatcaatcgt tttggacatg   1080
```

| attggtggtg gtactgatac tacaaagttg accactatat ggacattgtc tttgttgttg | 1140 |
| aacaacccac atgtcttaga caaagcaaag caagaagttg atgcccactt tagaaccaaa | 1200 |
| agaagatcta ctaacgacgc cgctgcagcc gttgtagatt tcgatgacat cagaaatttg | 1260 |
| gtttacatcc aagccataat caaggaatcc atgagattgt acccagctag tcctgtcgtt | 1320 |
| gaaagattat ctggtgaaga ttgtgtagtc ggtggttttc atgtaccagc tggtactaga | 1380 |
| ttatgggcaa acgtctggaa aatgcaaaga gatcctaagg tttgggatga cccattggtt | 1440 |
| tttagacctg atagattctt atcagacgaa caaaagatgg tagatgtcag aggtcaaaac | 1500 |
| tacgaattgt tgccattcgg tgctggtaga gagtatgtc ctggtgtcag tttctctttg | 1560 |
| gatttgatgc aattagtttt gaccagattg atattggaat tcgaaatgaa gtcaccatcc | 1620 |
| ggtaaagttg atatgactgc tacaccaggt ttgatgtctt acaaagtaat ccctttggat | 1680 |
| atcttgttga cacatagaag aattaaacca tgcgttcaat cagctgcatc cgaaagagat | 1740 |
| atggaatcat ccggtgttcc agtaatcacc ttgggttctg gtaaagtcat gcctgttttg | 1800 |
| ggtatgggta cttttgaaaa agttggtaaa ggttccgaaa gagaaagatt ggctatatta | 1860 |
| aaggcaatcg aagtaggtta tagatacttc gatacagccg ctgcatatga aaccgaagaa | 1920 |
| gtcttgggtg aagcaattgc cgaagctttg caattgggtt tagttaaatc tagagatgaa | 1980 |
| ttgtttataa gttctatgtt gtggtgtact gatgcacacg ccgacagagt attgttggct | 2040 |
| ttgcaaaaca gtttgagaaa tttgaagttg aatatgtcg atttgtacat gttaccattt | 2100 |
| cctgcatctt tgaagccagg taaaatcaca atggatatcc tgaagaaga catctgtaga | 2160 |
| atggattaca gaagtgtttg ggccgctatg gaagaatgcc aaaacttagg ttttacaaag | 2220 |
| tctatcggtg ttagtaactt ctcttgtaaa aagttgcaag aattaatggc taccgcaaac | 2280 |
| attccacctg ctgtaaatca agtcgaaatg tcaccagcat tccaacaaaa gaaattgaga | 2340 |
| gaatactgca atgcaaacaa tatattggtc tcagccatct ccgttttagg ttctaacggt | 2400 |
| actccttggg gttccaatgc tgtattgggt agtgaagtct tgaagaaaat tgccatggct | 2460 |
| aaaggtaaaa gtgttgcaca agtatctatg agatgggttt atgaacaagg tgcctctttg | 2520 |
| gttgtaaaga gttttctga agaaagattg agagaaaact taaacatctt cgactgggaa | 2580 |
| ttgacaaagg aagatcatga aaagattggt gaaataccac aatgtagaat attgtctgct | 2640 |
| tactttttag tttcaccaaa tggtcctttc aaatctcaag aagaattatg ggatgacgaa | 2700 |
| gcataa | 2706 |

<210> SEQ ID NO 32
<211> LENGTH: 1743
<212> TYPE: DNA
<213> ORGANISM: Artificial Sequence
<220> FEATURE:
<223> OTHER INFORMATION: Yeast codon optimized CYP82Y2

<400> SEQUENCE: 32

| atggaattac aatacatttc ttactttcaa cctacatcct ctgtcgtcgc cttgttatta | 60 |
| gcattagtct ctatcttatc ctccgtcgtt gtattgagaa agacattttt gaacaactac | 120 |
| tcttcatccc cagcaagttc tacaaagacc gccgttttat cacatcaaag acaacaatcc | 180 |
| tgtgctttgc ctataagtgg tttgttgcat atctttatga caaaaacgg tttgatccac | 240 |
| gtaacattgg gtaatatggc tgataagtac ggtccaattt tctctctttcc tacaggttcc | 300 |
| cacagaacct agtcgtttc atcctgggaa atggttaagg aatgcttcac tggtaacaac | 360 |
| gatacagctt tcagtaatag accaatccct ttggctttta aaactatttt ctatgcctgt | 420 |

```
ggtggtatag attcttacgg tttaagttct gttccatatg gtaaatactg gagagaattg      480
agaaaggttt gcgtacataa cttgttatca aatcaacaat tgttgaagtt tagacactta      540
ataatcagtc aagttgatac atctttcaac aaattatatg aattgtgtaa gaattctgaa      600
gacaaccatg gtaattacac tacaaccact acaaccgctg ctggtatggt tagaattgat      660
gactggttag ccgaattgtc ttttaatgtc ataggtagaa tcgtttgcgg tttccaatca      720
ggtccaaaaa ctggtgcacc ttccagagtt gaacaattca agaagccat aaacgaagct       780 agttatttca tgtcaacatc cccagtatct gataatgtcc ctatgttggg ttggattgac      840
caattaaccg gtttgactag aaacatgaag cattgtggta aaaagttgga tttggtagtc      900
gaatcaatca ttaatgacca cagacaaaag agaagatttt ccagaactaa aggtggtgac      960
gaaaaggatg acgaacaaga tgacttcatc gacatctgct tgtctatcat ggaacaacca     1020
caattgcctg gtaacaacaa cccatctcaa atccctatta aatcaatcgt tttggatatg     1080
attggtggtg gtacagacac tacaaagtta accactattt ggaccttgtc attgttgttg     1140
aacaacccac atgttttgga taaggctaag caagaagtag acgcacactt tagaaccaaa     1200
agaagatcca ctaacgatgc cgctgcagcc gttgtagact tcgatgacat aagaaatttg     1260
gtttacatcc aagctataat caaagaatcc atgagattgt acccagcaag tcctgtcgtt     1320
gaaagattgt ctggtgaaga ttgtgtagtc ggtggttttc atgtcccagc cggtactaga     1380
ttgtgggcta acgtttggaa aatgcaaaga gatcctaaag tatgggatga cccattagtc     1440
tttagacctg atagattctt gtctgacgaa caaaagatgg tcgatgttag aggtcaaaac     1500
tacgaattgt tgccatttgg tgctggtaga agagtttgtc ctggtgtaag tttctctttg     1560
gatttgatgc aattagtttt gaccagattg atattggaat tcgaaatgaa gtcaccatcc     1620
ggtaaagtag atatgactgc tacaccaggt ttaatgtctt acaaagtcat tcctttggat     1680
atcttgttga cacatagaag aattaagcca tgcgttcaaa gtgctgcatc tgaaagagat     1740
taa                                                                   1743
```

<210> SEQ ID NO 33
<211> LENGTH: 966
<212> TYPE: DNA
<213> ORGANISM: Artificial Sequence
<220> FEATURE:
<223> OTHER INFORMATION: Yeast codon optimised Oxidoreductase

<400> SEQUENCE: 33

```
atggaatcct ctggtgtccc tgttatcaca ttgggttctg gtaaagttat gcctgtcttg       60
ggtatgggta catttgaaaa ggtcggtaaa ggttctgaaa gagaaagatt agccatcttg      120
aaggctattg aagttggtta tagatacttt gacactgctg cagcctatga acagaagaa      180 gtattaggtg aagccatcgc tgaagcattg caattaggtt tggtcaagtc tagagatgaa      240
ttattcattt cttcaatgtt gtggtgtaca gatgcccatg ctgacagagt tttgttagct      300 ttgcaaaaact cttttgagaaa cttaaagttg gaatacgtag atttgtacat gttgccattt      360
cctgcttcat tgaagccagg taaaatcacc atggatatcc tgaagaaga catatgtaga      420 atggattaca gatccgtttg ggctgcaatg gaagaatgcc aaaatttggg ttttaccaag      480
agtatcggtg tttctaactt ctcatgtaaa aagttgcaag aattgatggc aactgccaat      540
atcccacctg ctgtcaacca agttgaaatg tccccagcat tccaacaaaa gaaattgaga      600
gaatactgca acgcaaacaa cattttagtt tccgccataa gtgtattggg ttcaaatggt      660
```

```
actccttggg gttccaacgc tgtcttaggt agtgaagttt tgaaaaagat tgctatggca    720
aagggtaaat ctgtagccca agtctcaatg agatgggttt atgaacaagg tgcatcatta    780
gttgtaaaat cctttagtga agaaagattg agagaaaatt tgaacatatt cgactgggaa    840
ttgacaaaag aagatcacga aaagattggt gaaataccac aatgcagaat cttgtctgct    900
tacttttggg tttcaccaaa tggtcctttc aagtctcaag aagaattgtg ggatgacgaa    960
gcataa                                                               966

<210> SEQ ID NO 34
<211> LENGTH: 40
<212> TYPE: DNA
<213> ORGANISM: Artificial Sequence
<220> FEATURE:
<223> OTHER INFORMATION: Primer XhoIF

<400> SEQUENCE: 34
aaaaggatcc aaaatgggt tcaaacaact tagccaactc                            40

<210> SEQ ID NO 35
<211> LENGTH: 40
<212> TYPE: DNA
<213> ORGANISM: Artificial Sequence
<220> FEATURE:
<223> OTHER INFORMATION: Primer CPR BamH1

<400> SEQUENCE: 35
aaaactcgag ttaccaaaca tctctcaaat atctttcttc                            40

<210> SEQ ID NO 36
<211> LENGTH: 44
<212> TYPE: DNA
<213> ORGANISM: Artificial Sequence
<220> FEATURE:
<223> OTHER INFORMATION: Primer CYP82X

<400> SEQUENCE: 36
aaaagcggcc gcaaaatgg aattacaata catctcctac tttc                        44

<210> SEQ ID NO 37
<211> LENGTH: 36
<212> TYPE: DNA
<213> ORGANISM: Artificial Sequence
<220> FEATURE:
<223> OTHER INFORMATION: Primer CYP82X

<400> SEQUENCE: 37
aaaattaatt aattatgctt cgtcatccca taattc                                36

<210> SEQ ID NO 38
<211> LENGTH: 44
<212> TYPE: DNA
<213> ORGANISM: Artificial Sequence
<220> FEATURE:
<223> OTHER INFORMATION: Primer CYO82X NotI F

<400> SEQUENCE: 38
aaaagcggcc gcaaaatgg aattacaata catttcttac tttc                        44

<210> SEQ ID NO 39
<211> LENGTH: 31
<212> TYPE: DNA
<213> ORGANISM: Artificial Sequence
<220> FEATURE:
<223> OTHER INFORMATION: Primer CYP82X PacI R
```

```
<400> SEQUENCE: 39
aaaattaatt aatctctttc agatgcagca c                               31

<210> SEQ ID NO 40
<211> LENGTH: 38
<212> TYPE: DNA
<213> ORGANISM: Artificial Sequence
<220> FEATURE:
<223> OTHER INFORMATION: Primer oxired NotI F

<400> SEQUENCE: 40
aaaagcggcc gcaaaaatgg aatcctctgg tgtccctg                        38

<210> SEQ ID NO 41
<211> LENGTH: 36
<212> TYPE: DNA
<213> ORGANISM: Artificial Sequence
<220> FEATURE:
<223> OTHER INFORMATION: Primer oxired R

<400> SEQUENCE: 41
aaaattaatt aattatgctt cgtcatccca caattc                          36

<210> SEQ ID NO 42
<211> LENGTH: 45
<212> TYPE: DNA
<213> ORGANISM: Artificial Sequence
<220> FEATURE:
<223> OTHER INFORMATION: Primer

<400> SEQUENCE: 42
tccagggacc agcaatggag ctccaatata tttcttattt tcaac                45

<210> SEQ ID NO 43
<211> LENGTH: 42
<212> TYPE: DNA
<213> ORGANISM: Artificial Sequence
<220> FEATURE:
<223> OTHER INFORMATION: Primer

<400> SEQUENCE: 43
tgaggagaag gcgcgttaag cttcatcatc ccacaactct tc                   42

<210> SEQ ID NO 44
<211> LENGTH: 8
<212> TYPE: PRT
<213> ORGANISM: Artificial Sequence
<220> FEATURE:
<223> OTHER INFORMATION: STORR Peptide

<400> SEQUENCE: 44

Thr Ala Val Leu Ser His Gln Arg
1               5

<210> SEQ ID NO 45
<211> LENGTH: 13
<212> TYPE: PRT
<213> ORGANISM: Artificial Sequence
<220> FEATURE:
<223> OTHER INFORMATION: STORR Peptide

<400> SEQUENCE: 45

Tyr Gly Pro Ile Phe Ser Phe Pro Thr Gly Ser His Arg
1               5                   10
```

<210> SEQ ID NO 46
<211> LENGTH: 10
<212> TYPE: PRT
<213> ORGANISM: Artificial Sequence
<220> FEATURE:
<223> OTHER INFORMATION: STORR Peptide

<400> SEQUENCE: 46

Ile Val Cys Gly Phe Gln Ser Gly Pro Lys
1               5                   10

<210> SEQ ID NO 47
<211> LENGTH: 10
<212> TYPE: PRT
<213> ORGANISM: Artificial Sequence
<220> FEATURE:
<223> OTHER INFORMATION: STORR Peptide

<400> SEQUENCE: 47

Leu Tyr Pro Ala Ser Pro Val Val Glu Arg
1               5                   10

<210> SEQ ID NO 48
<211> LENGTH: 12
<212> TYPE: PRT
<213> ORGANISM: Artificial Sequence
<220> FEATURE:
<223> OTHER INFORMATION: STORR Peptide

<400> SEQUENCE: 48

Ile Lys Pro Cys Val Gln Ser Ala Ala Ser Glu Arg
1               5                   10

<210> SEQ ID NO 49
<211> LENGTH: 8
<212> TYPE: PRT
<213> ORGANISM: Artificial Sequence
<220> FEATURE:
<223> OTHER INFORMATION: STORR Peptide

<400> SEQUENCE: 49

Ile Gly Glu Ile Pro Gln Cys Arg
1               5

<210> SEQ ID NO 50
<211> LENGTH: 966
<212> TYPE: DNA
<213> ORGANISM: Papaver somniferum

<400> SEQUENCE: 50
atggagagta gtggtgtacc agtaatcact ctgggctcgg gcaaggtgat gcctgttctt      60
ggcatgggaa catttgagaa agttggtaaa gggtccgaaa gagagaggtt ggcgatttta     120
aaagcgatag aggtgggtta cagatacttc gatacagctg ctgcatacga aactgaagag     180
gttcttggag aagctattgc tgaagcactt caacttggcc tagtcaaatc tcgagatgaa     240
cttttcatca gttccatgct ctggtgcact gatgctcacg ctgatcgtgt cctcctcgct     300
cttcagaatt cgctgaggaa tcttaaattg gagtatgtgg atctatatat gttacccttc     360
ccggcaagct tgaagcctgg gaagataacg atggacatac agaggaaga tatttgtcgc     420 atggactaca ggtctgtatg ggcagccatg aagagtgtc aaaaccttgg cttcactaaa     480
tcaatcggtg ttagcaattt ctcctgcaaa aagcttcagg aattgatggc gactgccaac     540
atccctccag ctgtgaatca agtggagatg agcccggctt ccaacaaaaa gaagctgaga     600

| | | | |
|---|---|---|---|
| gagtattgca | acgcaaataa | tatattagtc agtgcaatct ctgtactggg atcaaacgga | 660 |
| accccatggg | gctccaatgc | agtttTgggt tctgaggtgc ttaagaaaat tgctatggcc | 720 |
| aaaggaaaat | ctgttgctca | ggttagtatg agatgggttt acgagcaagg cgcgagtctt | 780 |
| gtggtaaaaa | gtttcagtga | agagagattg agggaaaact tgaacatatt tgactgggaa | 840 |
| ctcactaagg | aagaccatga | aaagatcggt gagattccac agtgcagaat cttgagtgct | 900 |
| tatttttgg | tctcacctaa | tggaccttTc aaatctcaag aagagttgtg ggatgatgaa | 960 |
| gcttga | | | 966 |

<210> SEQ ID NO 51
<211> LENGTH: 2650
<212> TYPE: DNA
<213> ORGANISM: Papaver somniferum

<400> SEQUENCE: 51

| | | | |
|---|---|---|---|
| cggcacgagc | ttgttagtat | cttctagggt ttgaaaagaa gcacagggag aagcaaaagt | 60 |
| cgaatctact | tgaaatacat | tcgattgctt ctctctgttt aagcttcaga gtctctgcta | 120 |
| attatgggtt | cgaataattt | agctaattcg attgaatcga tgttaggaat atcaatagga | 180 |
| tcagaatata | tttctgaccc | aatTTTcatt atggtcacaa ctgtagcttc aatgctgatt | 240 |
| ggatttggtt | tcttcgcatg | tatgaaatct tcgtcttctc aatcaaaacc tattgaaact | 300 |
| tataaaccaa | taattgataa | agaagaagag gagattgaag ttgatcctgg taaaattaag | 360 |
| ctcactatat | tttttggtac | tcagactggt actgctgaag gatttgctaa ggcattggca | 420 |
| gaagaaatta | aggcaaagta | caagaaagca gttgttaaag tagttgaccT ggatgactat | 480 |
| gcagccgagg | atgatcaata | tgaagagaaa ttaaagaaag agtctttggt gttttTcatg | 540 |
| gtagccactt | atggtgatgg | tgagccaact gacaatgctg cgagatttta caatggtTc | 600 |
| actcaggaac | atgaaagggg | agagtggctt cagcaactaa cttatggtgt ttttggtttg | 660 |
| ggtaaccgtc | aatacgagca | tttcaacaag atcgcggtag atgtggatga gcaactcggt | 720 |
| aaacaaggtg | caaagcgcat | tgttcaagtg gggctcggtg acgatgatca atgcattgaa | 780 |
| gatgatttta | ctgcttggcg | agaattgttg tggactgaat tggatcagtt gctcaaagat | 840 |
| gaggatgctg | ctccttcagt | ggctacaccg tatattgcta ctgttcctga atacagggta | 900 |
| gtgattcacg | aaactacggt | cgcggctctg atgataaac acataaatac tgctaacggc | 960 |
| gatgttgcat | tgatattct | ccatccttgc agaaccattg ttgctcaaca aagagagctc | 1020 |
| cacaaaccca | gtctgatag | atcctgtata catctgagt tcgacatatc aggctcttcc | 1080 |
| cttacatatg | agactggaga | tcatgttggt gtttatgctg agaactgcga tgaaactgtc | 1140 |
| gaggaagcag | gaagctgtt | gggtcaaccc ctggatttgc tgttttcaat tcacacggat | 1200 |
| aaagaagacg | ggtcaccca | gggaagctca ttaccacctc cttTcccagg tccttgcacc | 1260 |
| ttacgatctg | ccctagcacg | ctatgctgat cttTtgaatc ctcctagaaa ggcttctctg | 1320 |
| attgctctgt | ccgctcatgc | atctgtaccc agtgaagcag agagattgcg cttttTgtca | 1380 |
| tcacctctgg | gaaagaatga | gtattcaaaa tgggtagtTg gaagtcagag gagtcttttg | 1440 |
| gagatcatgg | ccgagtttcc | atcagcaaaa ccccctcttg gtgttttctT tgctgcagta | 1500 |
| gccctcgct | taccgcctcg | atactattct atctcatcct ctcctaagtt tgctccctca | 1560 |
| agaattcatg | tgacgtgtgc | tttagtatat ggtcaaagcc ctaccggaag ggttcaccga | 1620 |
| ggagtgtgtt | cgacatggat | gaagcatgca gttcctcagg atagctgggc tcctattTtt | 1680 |

```
gttcgaacgt caaacttcaa gttaccagct gacccctcaa ctccaattat catggtggga    1740
cctggtacag ggttagctcc tttcagagga tttctgcagg aaagaatggc cctcaaggaa    1800
aatggtgctc aacttggccc agcagtgctc tttttcggat gtaggaatcg taatatggac    1860
ttcatttatg aagacgaact aaacaacttc gtggaacgag gagtaatttc ggagctagtt    1920 attgccttt  cacgtgaagg ggaaaagaag gaatatgttc aacataagat gatggagaaa    1980
gcaacggatg tatggaatgt gatatcaggg gacggttatc tctatgtgtg tggtgatgcc    2040
aagggaatgg ccagagatgt ccatcgcacg ttgcatacca ttgcccaaga acagggaccc    2100
atggaatcat ctgctgccga agctgcagta aagaaactcc aagttgaaga acgatatcta    2160
agagatgtct ggtgatcgaa tgtagcttgc caagtcccct tttcttggct ggtctgttta    2220
tggtttctat tatattattg atcctcctct gaaaatccca agcacttcca gacatccctc    2280
gattcttcct ccagtggttc caaatcgaag ctcggtataa ttgagagcag tgcaattgtg    2340
actacatgag aagcaaacat cgaataccat agaattagaa agatcaaaat tctcttatca    2400
gaacaatgtt acaggcaaaa ctgtgtttgc ttaatataaa tttcacacca tgggtgtgga    2460
caacactgaa acagtattag ctataccaac aaagttatgc aaggaaacac aaactagtta    2520
gatcttctct ttggattgat tactgtaagt tctaaccaga tgatagattg tacttaaaga    2580
ttcttgtttt cttatggcta ccgagaggag tatattaatg catttagagt tttgagaaaa    2640
aaaaaaaaaa                                                          2650
```

CYTOCHROME P450 FUSION PROTEIN

CROSS REFERENCE TO RELATED APPLICATIONS

This is the U.S. National Stage of International Application No. PCT/GB2015/051446, filed May 15, 2015, which was published in English under PCT Article 21(2), which in turn claims the benefit of Great Britain Application No. 1408729.0 filed May 16, 2014 and Great Britain Application No. 1506805.9 filed Apr. 22, 2015.

FIELD OF THE INVENTION

This disclosure relates to the isolation of a nucleic acid molecule[s] that encode a novel cytochrome P450 and an oxidoreductase from a *Papaver somniferum* [*P. somniferum*] cultivar, transgenic cells transformed with said nucleic acid molecule and sequence variants thereof; and including processes for the production of intermediates in the production of phenanthrene alkaloids such as for example, morphine, codeine, oripavine and thebaine.

BACKGROUND TO THE INVENTION

The opium poppy, *Papaver somniferum* L., is an important source of a variety of alkaloids. Due to their narcotic and analgesic properties, opiate alkaloids and their derivates are desired for use in therapy. *P. somniferum* is a source of clinically useful alkaloids such as morphine, codeine, thebaine, noscapine [also known as narcotine] and papaverine. Morphine is the most abundant opiate alkaloid found in opium and is a powerful analgesic routinely used to reduce pain in humans. Opiate alkaloids are extracted from latex harvested from the green seed pods of opium poppy or from the poppy straw which is the dried mature plant. Morphinan alkaloids are known to derive from the intermediate (R)-reticuline. (R)-reticuline is thought to be formed by its enantiomer (S)-reticuline in a two-step isomerization process. In the first step, (S)-reticuline is transformed to 1,2-dehydroreticuline by the 1,2-dehydroreticuline synthase, and then reduced in the presence of NADPH to (R)-reticuline (FIG. 1). However, genes encoding the enzymes that perform the early conversion steps have not been identified thereby preventing engineering efforts employing the native enzymes.

Cytochrome P450 is a superfamily of monooxygenases with diverse catalytic activities such as oxidation, peroxidation and reduction. The primary chemical reaction catalysed by these monooxygenases is the two electron activation of molecular dioxygen, whereby one oxygen atom is inserted into the substrate with concomitant reduction of the second atom to water. Typically, NAD(P)H provides the required electron equivalents via a number of different redox partners. Many cytochrome P450s have been identified, with one third belonging to the plant kingdom, and found to be involved in the synthesis of a vast number of plant intermediate metabolites such as alkaloids, terpenoids, lipids, glycosides and glucosinolates. Cytochrome P450s are also known to be involved in the metabolism and detoxification of pesticides and other xenobiotic compounds. In eukaryotes, cytochrome P450s are mostly integral membrane bound proteins whereas prokaryotic cytochrome P450s are usually soluble and located in the cytoplasm. Typically, a cytochrome P450 enzyme requires a partnering reductase for the activation of molecular oxygen, which involves transferring two reducing equivalents from NAD(P)H to the heme of the cytochrome P450. Dependent on their redox partner, cytochrome P450 enzymes can be generally divided into two classes. In eukaryotes two component cytochrome P450 systems anchored to the membrane of the endoplasmic reticulum are prevalent comprising a flavin adenine dinucleotide/flavin mononucleotide (FAD/FMN) containing NADPH reductase partnered with a cytochrome P450 flavoprotein. In prokaryotes mainly three component systems can be found comprising an NAD(P)H-binding flavoprotein reductase, a small iron sulphur protein and the cytochrome P450 component. However, naturally occurring fusions of cytochrome P450 systems have also been identified, such as the fusions of the cytochrome P450 heme domain to its flavodoxin redox partner in *Rhodococcus rhodocrous* strain 11Y, or the soluble monooxygenase cytochrome P450BM3 from *Bacillus megaterium* comprising a diflavin reductase fused to the cytochrome P450 forming a self-sufficient system. Another self-sufficient fusion has been identified in *Rhodococcus* sp NCIMB 9784.

Plant cytochrome P450s are known to be involved in alkaloid metabolism and have been successfully cloned, expressed and characterized. For example, WO2009/064771 and WO2008/070274, each disclose cytochrome P450 genes and their use in the alteration of alkaloid content in *Nicotiana tabacum*. These disclosures describe the inhibition of specific P450s resulting in reduction in the amount of N' nitrosonornicotine, a known carcinogen, in planta. European application EP11748702.5 discloses cytochrome P450s unique to *Papaver somniferum* cultivars that produce noscapine. Furthermore, De-Eknamkul W and Zenk M. H. Phytochemistry [1992] Vol 31[3], p 813-821 discloses a 1,2-dehydroreticuline reductase activity that reduces stereospecifically 1,2-dehydroreticuline to (R)-reticuline isolated from *Papaver somniferum*. The enzyme activity is characterised and shown to be inhibited by (S)- and (R)-reticuline and is only present in morphinan alkaloid producing plants. WO99/35902 discloses mutant *Papaver somniferum* that show enhanced production of (S)-reticuline although the exact genetic nature of the mutant plants is not fully characterised.

This disclosure relates to a cytochrome P450 and an oxidoreductase from a *Papaver somniferum* cultivar involved in the two step isomerisation process of (S)-reticuline via 1,2-dehydroreticuline to (R)-reticuline, compounds essential for intermediates in the production of morphinans.

STATEMENTS OF INVENTION

According to an aspect of the invention there is provided an isolated polypeptide wherein said polypeptide comprises:
  i) a domain comprising an amino acid sequence comprising a cytochrome P450 activity wherein said activity catalyses the conversion of (S)-reticuline to 1,2-dehydroreticuline; and
  ii) a domain comprising an amino acid sequence comprising an oxidoreductase activity wherein said activity catalyses the conversion of 1,2-dehydroreticuline to (R)-reticuline.

In an aspect or preferred embodiment of the invention said polypeptide is selected from the group consisting of:
  i) a polypeptide comprising an amino acid sequence as set forth in SEQ ID NO: 1; or
  ii) a polypeptide comprising an amino acid sequence as set forth in SEQ ID NO: 2; or
  iii) a polypeptide comprising an amino acid sequence as set forth in SEQ ID NO: 3; or iv) a polypeptide comprising an amino acid sequence set forth in SEQ ID NO: 11; or v) a modified polypeptide comprising an amino acid sequence that is at least 50% identical to the full length amino acid sequence as set forth in SEQ ID NO: 1, 2, 3 or 11, wherein said sequence is modified by addition, deletion or substitution of one or more amino acid sequences and wherein said polypeptide has retained or enhanced enzyme activity when compared to the polypeptide comprising the amino acid sequence set forth in SEQ ID NO: 1, 2, 3 or 11; and/or vi) a polypeptide comprising the amino acid sequence KPCVQSAASERD set forth in SEQ ID NO: 7.

According to a further aspect of the invention there is provided a polypeptide comprising an amino acid sequence as set forth in SEQ ID NO: 1, or an amino acid sequence that is at least 50% identical to SEQ ID NO: 1.

According to a further aspect of the invention there is provided a polypeptide comprising an amino acid sequence as set forth in SEQ ID NO: 2, or an amino acid sequence that is at least 59% identical to SEQ ID NO: 2, wherein the polypeptide is an in-frame translational fusion with an oxidoreductase polypeptide.

According to a further aspect of the invention there is provided a polypeptide comprising an amino acid sequence as set forth in SEQ ID NO: 3, or an amino acid sequence that is at least 75% identical to SEQ ID NO: 3, wherein the polypeptide is an in-frame translational fusion with an cytochrome P450 polypeptide.

According to a further aspect of the invention there is provided an isolated polypeptide wherein said polypeptide is selected from the group consisting of:

i) a domain comprising an amino acid sequence comprising a cytochrome P450 activity wherein said activity catalyses the conversion of (S)-reticuline to 1,2-dehydroreticuline; or ii) a modified polypeptide comprising an amino acid sequence that is at least 59% identical to the full length amino acid sequence as set forth in SEQ ID NO: 2, wherein said sequence is modified by addition, deletion or substitution of one or more amino acid sequences and wherein said polypeptide has retained or enhanced enzyme activity when compared to the polypeptide comprising the amino acid sequence set forth in SEQ ID NO: 2.

According to a further aspect of the invention there is provided an isolated polypeptide wherein said polypeptide is selected from the group consisting of:

i) a domain comprising an amino acid sequence comprising an oxidoreductase activity wherein said activity catalyses the conversion of 1,2-dehydroreticuline to (R)-reticuline; or ii) a modified polypeptide comprising an amino acid sequence that is at least 75% identical to the full length amino acid sequence as set forth in SEQ ID NO: 3, wherein said sequence is modified by addition, deletion or substitution of one or more amino acid sequences and wherein said polypeptide has retained or enhanced enzyme activity when compared to the polypeptide comprising the amino acid sequence set forth in SEQ ID NO: 3.

According to a further aspect of the invention there is provided an isolated polypeptide wherein said polypeptide is selected from the group consisting of:

i) a domain comprising an amino acid sequence comprising an oxidoreductase activity wherein said activity catalyses the conversion of 1,2-dehydroreticuline to (R)-reticuline; or ii) a modified polypeptide comprising an amino acid sequence that is at least 75% identical to the full length amino acid sequence as set forth in SEQ ID NO: 11, wherein said sequence is modified by addition, deletion or substitution of one or more amino acid sequences and wherein said polypeptide has retained or enhanced enzyme activity when compared to the polypeptide comprising the amino acid sequence set forth in SEQ ID NO: 11.

A modified polypeptide as herein disclosed may differ in amino acid sequence by one or more substitutions, additions, deletions, truncations that may be present in any combination and includes polymorphic sequence variants that the skilled person would expect to exist in nature. Among preferred variants are those that vary from a reference polypeptide by conservative amino acid substitutions. Such substitutions are those that substitute a given amino acid by another amino acid of like characteristics. The following non-limiting list of amino acids are considered conservative replacements (similar): a) alanine, serine, and threonine; b) glutamic acid and aspartic acid; c) asparagine and glutamine d) arginine and lysine; e) isoleucine, leucine, methionine and valine and f) phenylalanine, tyrosine and tryptophan. Most highly preferred are variants that retain or enhance the same biological function and activity as the reference polypeptide from which it varies.

In a preferred embodiment of the invention said modified polypeptide is a variant and is at least 50%, 55%, 59%, 60%, 65%, 70%, 75%, 80%, 85%, 90%, 95%, 96%, 97%, 98% or 99% identical to the amino acid sequence set forth in SEQ ID NO: 1, 2, 3 or 11 over the full amino acid sequence.

In a preferred embodiment of the invention said variant is a polymorphic sequence variant.

According to a further aspect of the invention there is provided an isolated nucleic acid molecule that encodes a polypeptide according to the invention.

In a preferred embodiment of the invention said isolated nucleic acid molecule is selected from the group consisting of:

i) a nucleotide sequence as set forth in SEQ ID NO: 4, 5, 6 or 9;

ii) a nucleotide sequence wherein said sequence is degenerate as a result of the genetic code to the nucleotide sequence defined in (i);

iii) a nucleic acid molecule the complementary strand of which hybridizes under stringent hybridization conditions to the nucleotide sequence set forth in SEQ ID NO: 4, 5, 6 or 9 and which encodes a polypeptide that has cytochrome P450 and/or oxidoreductase activity as herein disclosed.

In a preferred embodiment of the invention said nucleic acid molecule comprises a nucleotide sequence set forth in SEQ ID NO: 4 wherein said nucleotide sequence comprises an open reading frame between nucleotides 1 to 2706.

In a preferred embodiment of the invention said open reading frame comprises the nucleotide sequence set forth in SEQ ID NO: 29.

In a preferred embodiment of the invention said nucleic acid molecule comprises a nucleotide sequence set forth in SEQ ID NO: 6 wherein said nucleotide sequence comprises an open reading frame between nucleotides 1 to 966.

In a preferred embodiment of the invention said open reading frame comprises the nucleotide sequence set forth in SEQ ID NO: 50.

In a preferred embodiment of the invention said nucleic acid molecule comprises a nucleotide sequence set forth in SEQ ID NO: 9.

In a preferred embodiment of the invention said comprises the nucleotide sequence set forth in SEQ ID NO: 10.

According to an aspect of the invention there is provided an isolated nucleic acid molecule is selected from the group consisting of:
  i) a nucleotide sequence as set forth in SEQ ID NO: 31, 32 or 33;
  ii) a nucleotide sequence wherein said sequence is degenerate as a result of the genetic code to the nucleotide sequence defined in (i) above;
  iii) a nucleic acid molecule the complementary strand of which hybridizes under stringent hybridization conditions to the nucleotide sequence set forth in SEQ ID NO: 31, 32 or 33 and which encodes a polypeptide that has cytochrome P450 and/or oxidoreductase activity as herein disclosed.

According to an aspect of the invention there is provided an isolated nucleic acid molecule selected from the group consisting of:
i) a nucleotide sequence as set forth in SEQ ID NO: 30;
ii) a nucleotide sequence wherein said sequence is degenerate as a result of the genetic code to the nucleotide sequence defined in (i) above;
iii) a nucleic acid molecule the complementary strand of which hybridizes under stringent hybridization conditions to the nucleotide sequence set forth in SEQ ID NO: 30 which encodes a polypeptide that has cytochrome P450 reductase activity.

According to an aspect of the invention there is provided an isolated nucleic acid molecule selected from the group consisting of:
i) a nucleotide sequence as set forth in SEQ ID NO: 10.
ii) a nucleotide sequence wherein said sequence is degenerate as a result of the genetic code to the nucleotide sequence defined in (i) above;
iii) a nucleic acid molecule the complementary strand of which hybridizes under stringent hybridization conditions to the nucleotide sequence set forth in SEQ ID NO: 10 which encodes a polypeptide that has oxidoreductase activity According to an aspect of the invention there is provided an isolated nucleic acid molecule selected from the group consisting of:
i) a nucleotide sequence as set forth in SEQ ID NO: 50;
ii) a nucleotide sequence wherein said sequence is degenerate as a result of the genetic code to the nucleotide sequence defined in (i) above;
iii) a nucleic acid molecule the complementary strand of which hybridizes under stringent hybridization conditions to the nucleotide sequence set forth in SEQ ID NO: 50 which encodes a polypeptide that has oxidoreductase activity According to an aspect of the invention there is provided an isolated nucleic acid molecule selected from the group consisting of:
i) a nucleotide sequence as set forth in SEQ ID NO: 29;
ii) a nucleotide sequence wherein said sequence is degenerate as a result of the genetic code to the nucleotide sequence defined in (i) above;
iii) a nucleic acid molecule the complementary strand of which hybridizes under stringent hybridization conditions to the nucleotide sequence set forth in SEQ ID NO: 29 which encodes a polypeptide that has cytochrome P450 and/or oxidoreductase activity Hybridization of a nucleic acid molecule occurs when two complementary nucleic acid molecules undergo an amount of hydrogen bonding to each other. Isolated nucleic acid molecules as referred herein include genomic DNA, cDNA molecules and RNA molecules. The stringency of hybridization can vary according to the environmental conditions surrounding the nucleic acids, the nature of the hybridization method, and the composition and length of the nucleic acid molecules used. Calculations regarding hybridization conditions required for attaining particular degrees of stringency are discussed in Sambrook et al., Molecular Cloning: A Laboratory Manual (Cold Spring Harbor Laboratory Press, Cold Spring Harbor, N.Y., 2001); and Tijssen, Laboratory Techniques in Biochemistry and Molecular Biology—Hybridization with Nucleic Acid Probes Part I, Chapter 2 (Elsevier, New York, 1993). The $T_m$ is the temperature at which 50% of a given strand of a nucleic acid molecule is hybridized to its complementary strand. The following is an exemplary set of hybridization conditions and is not limiting:

Very High Stringency (Allows Sequences that Share at Least 90% Identity to Hybridize)
  Hybridization: 5×SSC at 65° C. for 16 hours
  Wash twice: 2×SSC at room temperature (RT) for 15 minutes each
  Wash twice: 0.5×SSC at 65° C. for 20 minutes each
High Stringency (Allows Sequences that Share at Least 80% Identity to Hybridize)
  Hybridization: 5×-6×SSC at 65° C.-70° C. for 16-20 hours
  Wash twice: 2×SSC at RT for 5-20 minutes each
  Wash twice: 1×SSC at 55° C.-70° C. for 30 minutes each
Low Stringency (Allows Sequences that Share at Least 50% Identity to Hybridize)
  Hybridization: 6×SSC at RT to 55° C. for 16-20 hours
  Wash at least twice: 2×-3×SSC at RT to 55° C. for 20-30 minutes each.

In a preferred embodiment of the invention said isolated nucleic acid molecule is at least 50% identical to the nucleotide sequence set forth in SEQ ID NO: 4, 5, 6 or 9.

Preferably, the isolated nucleic acid molecule is at least 55%, 60%, 65%, 70%, 75%, 80%, 90%, 91%, 92%, 93%, 94%, 95%, 96%, 97%, 98% or 99% identical to the nucleotide sequence set forth in SEQ ID NO: 4, 5, 6, or 9 over the full nucleotide sequence.

Preferably, said isolated nucleic acid molecule is at least 70%, 75%, 80%, 90%, 91%, 92%, 93%, 94%, 95%, 96%, 97%, 98% or 99% identical to the nucleotide sequence set forth in SEQ ID NO: 10, 29, 30, 31, 32, 33 or 50 over the full nucleotide sequence.

In a preferred embodiment of the invention said nucleic acid molecule comprises or consists of a nucleotide sequence as represented in SEQ ID NO: 4, 5, 6 or 9.

In a preferred embodiment of the invention said nucleic acid molecule comprises or consists of a nucleotide sequence as represented in SEQ ID NO: 10, 29, 30, 31, 32, 33 or 50.

According to a further aspect of the invention there is provided a vector comprising a nucleic acid molecule encoding a polypeptide according to the invention wherein said nucleic acid molecule is operably linked to a nucleic acid molecule comprising a promoter sequence.

In a preferred embodiment of the invention said nucleic acid sequence comprising a promoter confers constitutive expression on the nucleic acid molecule according to the invention.

In an alternative preferred embodiment of the invention said nucleic acid molecule comprising a promoter confers regulated expression on the nucleic acid molecule according to the invention.

In a preferred embodiment of the invention said regulated expression is tissue or developmentally regulated expression.

In a further alternative embodiment of the invention said regulated expression is inducible expression.

In an alternative embodiment of the invention a vector including a nucleic acid molecule according to the invention need not include a promoter or other regulatory sequence, particularly if the vector is to be used to introduce the nucleic acid molecule into cells for recombination into the gene.

Preferably, the nucleic acid molecule according to the invention is under the control of, and operably linked to, an appropriate promoter or other regulatory elements for transcription in a host cell such as a microbial (e.g. bacterial, yeast) or plant cell. The vector may be a bi-functional expression vector which functions in multiple hosts. In the case of cytochrome P450 or oxidoreductase genomic DNA this may contain its own promoter or other regulatory elements and in the case of cDNA this may be under the control of an appropriate promoter or other regulatory elements for expression in the host cell.

By "promoter" is meant a nucleotide sequence upstream from the transcriptional initiation site and which contains all the regulatory regions required for transcription. Suitable promoters include constitutive, tissue-specific, inducible, developmental or other promoters for expression in plant cells comprised in plants depending on design. Such promoters include viral, fungal, bacterial, animal and plant-derived promoters capable of functioning in plant cells.

Constitutive promoters include, for example CaMV 35S promoter (Odell et al. (1985) Nature 313, 9810-812); rice actin (McElroy et al. (1990) Plant Cell 2: 163-171); ubiquitin (Christian et al. (1989) Plant Mol. Biol. 18 (675-689); pEMU (Last et al. (1991) Theor Appl. Genet. 81: 581-588); MAS (Velten et al. (1984) EMBO J. 3. 2723-2730); ALS promoter (U.S. application Ser. No. 08/409,297), and the like. Other constitutive promoters include those in U.S. Pat. Nos. 5,608,149; 5,608,144; 5,604,121; 5,569,597; 5,466,785; 5,399,680, 5,268,463; and 5,608,142, each of which is incorporated by reference.

Chemical-regulated promoters can be used to modulate the expression of a gene in a plant through the application of an exogenous chemical regulator. Depending upon the objective, the promoter may be a chemical-inducible promoter, where application of the chemical induced gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) Proc. Natl. Acad. Sci. USA 88: 10421-10425 and McNellis et al. (1998) Plant J. 14(2): 247-257) and tetracycline-inducible and tetracycline-repressible promoters (see, for example, Gatz et al. (1991) Mol. Gen. Genet. 227: 229-237, and U.S. Pat. Nos. 5,814,618 and 5,789,156, herein incorporated by reference.

Where enhanced expression in particular tissues is desired, tissue-specific promoters can be utilised. Tissue-specific promoters include those described by Yamamoto et al. (1997) Plant J. 12(2): 255-265; Kawamata et al. (1997) Plant Cell Physiol. 38(7): 792-803; Hansen et al. (1997) Mol. Gen. Genet. 254(3): 337-343; Russell et al. (1997) Transgenic Res. 6(2): 157-168; Rinehart et al. (1996) Plant Physiol. 112(3): 1331-1341; Van Camp et al. (1996) Plant Physiol. 112(2): 525-535; Canevascni et al. (1996) Plant Physiol. 112(2): 513-524; Yamamoto et al. (1994) Plant Cell Physiol. 35(5): 773-778; Lam (1994) Results Probl. Cell Differ. 20: 181-196; Orozco et al. (1993) Plant Mol. Biol. 23(6): 1129-1138; Mutsuoka et al. (1993) Proc. Natl. Acad. Sci. USA 90 (20): 9586-9590; and Guevara-Garcia et al (1993) Plant J. 4(3): 495-50.

"Operably linked" means joined as part of the same nucleic acid molecule, suitably positioned and oriented for transcription to be initiated from the promoter. DNA operably linked to a promoter is "under transcriptional initiation regulation" of the promoter. In a preferred aspect, the promoter is a tissue specific promoter, an inducible promoter or a developmentally regulated promoter.

Particular of interest in the present context are nucleic acid constructs which operate as plant vectors. Specific procedures and vectors previously used with wide success in plants are described by Guerineau and Mullineaux (1993) (Plant transformation and expression vectors. In: Plant Molecular Biology Labfax (Croy RRD ed) Oxford, BIOS Scientific Publishers, pp 121-148. Suitable vectors may include plant viral-derived vectors (see e.g. EP194809). If desired, selectable genetic markers may be included in the construct, such as those that confer selectable phenotypes such as resistance to herbicides (e.g. kanamycin, hygromycin, phosphinotricin, chlorsulfuron, methotrexate, gentamycin, spectinomycin, imidazolinones and glyphosate).

According to a further aspect of the invention there is provided a transgenic cell transformed or transfected with a nucleic acid molecule or vector according to the invention.

According to an aspect of the invention there is provided an isolated transgenic cell transformed or transfected with a nucleic acid molecule or vector according to the invention.

In a preferred embodiment of the invention said cell is a plant cell.

In a preferred embodiment of the invention said plant cell is from the genus *Papaver*. In a preferred embodiment of the invention said plant cell is a *Papaver somniferum* cell. According to a further aspect of the invention there is provided a transgenic plant comprising a plant cell according to the invention.

In a preferred embodiment of the invention said plant is from the genus *Papaver*; preferably *Papaver somniferum, P. setigerum, P. bracteatum, P. orientale, P. pseudo-orientale, P. lasiothrix, P. cylindricum, P. fugax, P. triniifolium.*

In an alternative preferred embodiment of the invention said cell is a microbial cell; preferably a bacterial or fungal cell [e.g. yeast, *Saccharomyces cerevisae*].

In a further alternative preferred embodiment of the invention said bacterial cell is selected from the group consisting of *Escherichia coli, Corynebacterium, Pseudomonas fluorescens* or *Agrobacterium tumefaciens.*

In a further alternative preferred embodiment of the invention said fungal cell is selected from the group consisting of *Saccharomyces cerevisae* or *Pichia Pastoris.*

In a preferred embodiment of the invention said cell is adapted such that the nucleic acid molecule according to the invention is over-expressed when compared to a non-transgenic cell of the same species.

In a preferred embodiment of the invention said microbial cell expresses a cytochrome P450 encoded by a nucleotide sequence selected from the group consisting of:
i) a nucleotide sequence as set forth in SEQ ID NO: 5 or 32;
ii) a nucleotide sequence wherein said sequence is degenerate as a result of the genetic code to the nucleotide sequence defined in (i) above;
iii) a nucleic acid molecule the complementary strand of which hybridizes under stringent hybridization conditions to the nucleotide sequence set forth in SEQ ID NO: 5 or 32 and which encodes a polypeptide that has cytochrome P450 activity.

In a preferred embodiment of the invention said microbial cell expresses an oxidoreductase encoded by a nucleotide sequence selected from the group consisting of:
i) a nucleotide sequence as set forth in SEQ ID NO: 6, 10, 33 or 50;
ii) a nucleotide sequence wherein said sequence is degenerate as a result of the genetic code to the nucleotide sequence defined in (i);
iii) a nucleic acid molecule the complementary strand of which hybridizes under stringent hybridization conditions to the nucleotide sequence set forth in SEQ ID NO: 6, 10, 33 or 50 and which encodes a polypeptide that has oxidoreductase activity.

In a preferred embodiment of the invention said microbial cell expresses a cytochrome P450 reductase.

Cytochrome P450s are heme containing enzymes and require auxiliary reductases for the activation of molecular oxygen. These auxiliary reductases transfer two electrons from the cofactors such as NAD (P)H to the heme of the cytochrome P450. It will be apparent that a cytochrome P450 domain derived from the fusion protein according to the invention or the fusion protein comprising the cytochrome P450 and oxidoreductase requires such auxiliary reductase for activity.

In a preferred embodiment of the invention said microbial cell expresses an NADH or NADPH dependent cytochrome P450 reductase.

In a preferred embodiment of the invention said microbial cell is transformed with a nucleic acid molecule or vector comprising said NADH or NADPH dependent cytochrome P450 reductase.

In a preferred embodiment of the invention said microbial cell is transformed with a nucleic acid molecule or vector encoding a plant NADH or NADPH dependent cytochrome P450 reductase.

In a preferred embodiment of the invention said reductase is encoded by a nucleotide sequence selected from the group consisting of:
i) a nucleotide sequence as set forth in SEQ ID NO: 30;
ii) a nucleotide sequence wherein said sequence is degenerate as a result of the genetic code to the nucleotide sequence defined in (i) above;
iii) a nucleic acid molecule the complementary strand of which hybridizes under stringent hybridization conditions to the nucleotide sequence set forth in SEQ ID NO: 30 and which encodes a polypeptide that has NADH or NADPH dependent cytochrome P450 reductase activity.

In a preferred embodiment of the invention said nucleotide sequence is at least 70%, 75%, 80%, 90%, 91%, 92%, 93%, 94%, 95%, 96%, 97%, 98% or 99% identical to the nucleotide sequence set forth in SEQ ID NO: 30 over the full nucleotide sequence.

In an alternative preferred embodiment of the invention said cytochrome P450 reductase is encoded by a nucleotide sequence selected from the group consisting of:
i) a nucleotide sequence as set forth in SEQ ID NO: 51;
ii) a nucleotide sequence wherein said sequence is degenerate as a result of the genetic code to the nucleotide sequence defined in (i);
iii) a nucleic acid molecule the complementary strand of which hybridizes under stringent hybridization conditions to the nucleotide sequence set forth in SEQ ID NO: 51 and which encodes a polypeptide that has NADH or NADPH dependent cytochrome P450 reductase activity.

In a preferred embodiment of the invention said nucleotide sequence is at least 70%, 75%, 80%, 90%, 91%, 92%, 93%, 94%, 95%, 96%, 97%, 98% or 99% identical to the nucleotide sequence set forth in SEQ ID NO: 51 over the full nucleotide sequence.

According to an aspect of the invention there is provided a process for the production of a polypeptide according to the invention comprising:
i) providing a cell that expresses a polypeptide selected from the group consisting of:
  a) a polypeptide comprising an amino acid sequence as set forth in SEQ ID NO: 1; or
  b) a polypeptide comprising an amino acid sequence as set forth in SEQ ID NO: 2; or
  c) a polypeptide comprising an amino acid sequence as set forth in SEQ ID NO: 3; or
  d) a polypeptide comprising an amino acid sequence as set forth in SEQ ID NO: 11; or
  e) a modified polypeptide comprising an amino acid sequence that is at least 50% identical to the full length amino acid sequence as set forth in SEQ ID NO: 1, 2, 3 or 11, wherein said sequence is modified by addition, deletion or substitution of one or more amino acid sequences when compared to the polypeptide comprising the amino acid sequence set forth in SEQ ID NO: 1, 2, 3 or 11; and/or
  f) a polypeptide comprising the amino acid sequence KPCVQSAASERD as set forth in SEQ ID NO: 7;
ii) culturing said cell under cell culture conditions conducive to the expression of said polypeptide; and optionally
iii) extracting said polypeptide from the cell or cell culture medium.

In a preferred process of the invention said cell is a transgenic cell according to the invention.

In a preferred process of the invention said transgenic cell is transformed with a vector according to the invention.

In a preferred process of the invention said polypeptide comprises an amino acid sequence as set forth in SEQ ID NO: 1.

In a preferred process of the invention said polypeptide comprises an amino acid sequence as set forth in SEQ ID NO: 2.

In a preferred process of the invention said polypeptide comprises an amino acid sequence as set forth in SEQ ID NO: 3.

In a preferred process of the invention said polypeptide comprises an amino acid sequence as set forth in SEQ ID NO: 11.

In a preferred process of the invention said cell is a microbial cell; preferably a bacterial cell.

In a further preferred process of the invention said bacterial cell is selected from the group consisting of *Escherichia coli, Corynebacterium, Pseudomonas fluorescens* or *Agrobacterium tumefaciens*.

In an alternative preferred process of the invention said microbial cell is a yeast cell.

In a further preferred process of the invention said yeast cell is selected from the group consisting of *Saccharomyces cerevisae* or *Pichia Pastoris*.

According to a further aspect of the invention there is provided a nucleic acid molecule comprising a transcription cassette wherein said cassette includes a nucleotide sequence designed with reference to SEQ ID NO: 4, 5, 6 or 9 and is adapted for expression by provision of at least one promoter operably linked to said nucleotide sequence such that both sense and antisense molecules are transcribed from said cassette.

In a preferred embodiment of the invention said nucleic acid molecule comprises a transcription cassette wherein said cassette includes a nucleotide sequence at least 55%, 60%, 65%, 70%, 75%, 80%, 90%, 91%, 92%, 93%, 94%, 95%, 96%, 97%, 98%, 99% or 100% identical to the nucleotide sequence set forth in SEQ ID NO: 4, 5, 6 or 9.

In a preferred embodiment of the invention said nucleic acid molecule comprises a transcription cassette wherein said cassette includes a nucleotide sequence designed with reference to SEQ ID NO: 29.

In a preferred embodiment of the invention said nucleic acid molecule comprises a transcription cassette wherein said cassette includes a nucleotide sequence at least 55%, 60%, 65%, 70%, 75%, 80%, 90%, 91%, 92%, 93%, 94%, 95%, 96%, 97%, 98%, 99% or 100% identical to the nucleotide sequence set forth in SEQ ID NO: 29.

In a preferred embodiment of the invention said nucleic acid molecule comprises a transcription cassette wherein said cassette includes a nucleotide sequence designed with reference to SEQ ID NO: 50.

In a preferred embodiment of the invention said nucleic acid molecule comprises a transcription cassette wherein said cassette includes a nucleotide sequence at least 55%, 60%, 65%, 70%, 75%, 80%, 90%, 91%, 92%, 93%, 94%, 95%, 96%, 97%, 98%, 99% or 100% identical to the nucleotide sequence set forth in SEQ ID NO: 50.

In a preferred embodiment of the invention said nucleic acid molecule comprises a transcription cassette wherein said cassette includes a nucleotide sequence designed with reference to SEQ ID NO: 10.

In a preferred embodiment of the invention said nucleic acid molecule comprises a transcription cassette wherein said cassette includes a nucleotide sequence at least 55%, 60%, 65%, 70%, 75%, 80%, 90%, 91%, 92%, 93%, 94%, 95%, 96%, 97%, 98%, 99% or 100% identical to the nucleotide sequence set forth in SEQ ID NO: 10.

In a preferred embodiment of the invention said nucleic acid molecule comprises a transcription cassette wherein said cassette includes a nucleotide sequence designed with reference to a SEQ ID NO: 4 and/or SEQ ID NO: 5 and/or SEQ ID NO: 6 and/or SEQ ID NO: 9 and/or SEQ ID NO: 10 and/or SEQ ID NO: 29 and/or SEQ ID NO: 50.

In a preferred embodiment of the invention said cassette is adapted such that both sense and antisense ribonucleic acid molecules are transcribed from said cassette wherein said sense and antisense nucleic acid molecules are adapted to anneal over at least part or all of their length to form a inhibitory RNA or short hairpin RNA.

In a preferred embodiment of the invention said cassette is provided with at least two promoters adapted to transcribe both sense and antisense strands of said ribonucleic acid molecule.

In an alternative preferred embodiment of the invention said cassette comprises a nucleic acid molecule wherein said molecule comprises a first part linked to a second part wherein said first and second parts are complementary over at least part of their sequence and further wherein transcription of said nucleic acid molecule produces a ribonucleic acid molecule which forms a double stranded region by complementary base pairing of said first and second parts thereby forming a short hairpin RNA.

A technique to specifically ablate gene function is through the introduction of double stranded RNA, also referred to as small inhibitory/interfering RNA (siRNA) or short hairpin RNA [shRNA], into a cell which results in the destruction of mRNA complementary to the sequence included in the siRNA/shRNA molecule. The siRNA molecule comprises two complementary strands of RNA (a sense strand and an antisense strand) annealed to each other to form a double stranded RNA molecule. The siRNA molecule is typically derived and designed with reference to exons of the gene which is to be ablated. There are numerous publically available websites that allow the optimal design of siRNA/shRNA molecules that require the introduction of a sequence, i.e. nucleotide sequences according to the invention, as a start point in the design of siRNA/shRNA molecules. The mechanism of RNA interference is being elucidated. Many organisms respond to the presence of double stranded RNA by activating a cascade that leads to the formation of siRNA. The presence of double stranded RNA activates a protein complex comprising RNase III which processes the double stranded RNA into smaller fragments (siRNAs, approximately 21-29 nucleotides in length) which become part of a ribonucleoprotein complex. The siRNA acts as a guide for the RNase complex to cleave mRNA complementary to the antisense strand of the siRNA thereby resulting in destruction of the mRNA.

In a preferred embodiment of the invention said nucleic acid molecule is part of a vector adapted for expression in a plant cell.

According to a further aspect of the invention there is provided a plant cell transfected with a nucleic acid molecule or vector according to the invention wherein said cell has reduced expression of the nucleic acid molecule according to the invention.

According to an aspect of the invention there is provided a process for the transformation of (S)-reticuline to (R)-reticuline comprising:

i) providing a transgenic plant cell according to the invention;
ii) cultivating said plant cell to produce a transgenic plant; and optionally
iii) harvesting said transgenic plant, or part thereof.

In a preferred method of the invention the transformation of (S)-reticuline to (R)-reticuline is via 1,2-dehydroreticuline.

In a preferred method of the invention said plant cell is transformed with a nucleic acid molecule encoding a cytochrome P450 reductase.

In a preferred method of the invention said plant cell is transformed with a nucleic acid molecule encoding a cytochrome P450 reductase according to the invention.

In a preferred method of the invention said plant cell is transformed with a nucleic acid molecule encoding an NADH or NADPH dependent cytochrome P450 reductase.

In a preferred method of the invention said plant cell is transformed with a nucleic acid molecule encoding an NADH or NADPH dependent cytochrome P450 reductase according to the invention.

In a preferred method of the invention said harvested plant material is dried and (R)-reticuline is extracted.

According to an alternative aspect of the invention there is provided a process for the transformation of (S)-reticuline to (R)-reticuline comprising:
i) providing a transgenic microbial cell according to the invention that expresses the nucleic acid molecule according to the invention in culture with at least (S)-reticuline;
ii) cultivating the microbial cell under conditions that transform (S)-reticuline;
and optionally
iii) isolating (R)-reticuline from the microbial cell or cell culture.

In a preferred method of the invention the transformation of (S)-reticuline to (R)-reticuline is via 1,2-dehydroreticuline.

In a preferred method of the invention said microbial cell is transformed with a nucleic acid molecule encoding a cytochrome P450 reductase.

In a preferred method of the invention said microbial cell is transformed with a nucleic acid molecule encoding a cytochrome P450 reductase according to the invention.

In a preferred method of the invention said microbial cell is transformed with a nucleic acid molecule encoding an NADH or NADPH reductase.

In a preferred method of the invention said microbial cell is transformed with a nucleic acid molecule encoding an NADH or NADPH reductase according to the invention.

According to an alternative aspect of the invention there is provided a process for the transformation of 1, 2-dehydroreticuline to (R)-reticuline comprising:
i) providing a transgenic microbial cell according to the invention that expresses the nucleic acid molecule according to the invention in culture with at least 1,2-dehydroreticuline;
ii) cultivating the microbial cell under conditions that transform 1,2-dehydroreticuline; and optionally
iii) isolating (R)-reticuline from the microbial cell or cell culture.

In a preferred method of the invention said microbial cell is a bacterial cell or fungal/yeast cell.

In a further preferred method of the invention said bacterial cell is selected from the group consisting of *Escherichia coli, Corynebacterium, Pseudomonas fluorescens* or *Agrobacterium tumefaciens.*

In a preferred method of the invention said fungal/yeast cell is selected from the group consisting of *Saccharomyces cerevisae* or *Pichia Pastoris.*

Assembly methods using restriction enzymes and DNA ligases to join DNA segments together, either sequentially or in a single reaction or use homology-dependent assembly in vitro or in vivo are known in the art. Furthermore, highly efficient, rapid and easy recombinational assembly methods have been developed using integrases to assemble predesigned pathways and devices from DNA parts allowing, once the individual cassette is assembled, the replacement, deletion or addition of genes or other DNA elements at will (Colloms et al., Rapid metabolic pathway assembly and modification using serine integrase site-specific recombination. Nucleic Acids Research, 2014, Vol. 42, No. 4). Thus the recombinational assembly method provides great flexibility and rapid pathway optimization and allows the reconstruction of metabolic pathways in host cells such as microbial cells e.g. bacteria, yeast and fungal cells.

According to an aspect of the invention there is provided the use of a polypeptide or nucleic acid molecule according to the invention in engineering one or more metabolic pathways in a host microbial cell.

If microbial cells are used as organisms in the process according to the invention they are grown or cultured in the manner with which the skilled worker is familiar, depending on the host organism. As a rule, microorganisms are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C., while gassing in oxygen.

The pH of the liquid medium can either be kept constant, that is to say regulated during the culturing period, or not. The cultures can be grown batchwise, semi-batchwise or continuously. Nutrients can be provided at the beginning of the fermentation or fed in semi-continuously or continuously. The opiate alkaloids produced can be isolated from the organisms as described above by processes known to the skilled worker, for example by extraction, distillation, crystallization, if appropriate precipitation with salt, and/or chromatography. To this end, the organisms can advantageously be disrupted beforehand. In this process, the pH value is advantageously kept between pH 4 and 12, preferably between pH 6 and 9, especially preferably between pH 7 and 8.

The culture medium to be used must suitably meet the requirements of the strains in question. Descriptions of culture media for various microorganisms can be found in the textbook "Manual of Methods for General Bacteriology" of the American Society for Bacteriology (Washington D.C., USA, 1981).

As described above, these media which can be employed in accordance with the invention usually comprise one or more carbon sources, nitrogen sources, inorganic salts, vitamins and/or trace elements.

Preferred carbon sources are sugars, such as mono-, di- or polysaccharides. Examples of carbon sources are glucose, fructose, mannose, galactose, ribose, sorbose, ribulose, lactose, maltose, sucrose, raffinose, starch or cellulose. Sugars can also be added to the media via complex compounds such as molasses or other by-products from sugar refining. The addition of mixtures of a variety of carbon sources may also be advantageous. Other possible carbon sources are oils and fats such as, for example, soya oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol, and/or organic acids such as, for example, acetic acid and/or lactic acid.

Nitrogen sources are usually organic or inorganic nitrogen compounds or materials comprising these compounds. Examples of nitrogen sources comprise ammonia in liquid or gaseous form or ammonium salts such as ammonium sulfate, ammonium chloride, ammonium phosphate, ammonium carbonate or ammonium nitrate, nitrates, urea, amino acids or complex nitrogen sources such as cornsteep liquor, soya meal, soya protein, yeast extract, meat extract and others. The nitrogen sources can be used individually or as a mixture.

Inorganic salt compounds which may be present in the media comprise the chloride, phosphorus and sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing fine chemicals, in particular of methionine.

Phosphoric acid, potassium dihydrogenphosphate or dipotassium hydrogenphosphate or the corresponding sodium-containing salts may be used as sources of phosphorus.

Chelating agents may be added to the medium in order to keep the metal ions in solution. Particularly suitable chelating agents comprise dihydroxyphenols such as catechol or protocatechuate and organic acids such as citric acid.

The fermentation media used according to the invention for culturing microorganisms usually also comprise other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, cornsteep liquor and the like. It is moreover possible to add suitable precursors to the culture medium. The exact composition of the media compounds heavily depends on the particular experiment and is decided upon individually for each specific case. Information on the optimization of media can be found in the textbook "Applied Microbiol. Physiology, A Practical Approach" (Editors P. M. Rhodes, P. F. Stanbury, IRL Press (1997) pp. 53-73, ISBN 0 19 963577 3). Growth media can also be obtained from commercial suppliers, for example Standard 1 (Merck) or BHI (brain heart infusion, DIFCO) and the like.

All media components are sterilized, either by heat (20 min at 1.5 bar and 121° C.) or by filter sterilization. The components may be sterilized either together or, if required, separately. All media components may be present at the start of the cultivation or added continuously or batchwise, as desired.

The culture temperature is normally between 15° C. and 45° C., preferably at from 25° C. to 40° C., and may be kept constant or may be altered during the experiment. The pH of the medium should be in the range from 5 to 8.5, preferably around 7.0. The pH for cultivation can be controlled during cultivation by adding basic compounds such as sodium hydroxide, potassium hydroxide, ammonia and aqueous ammonia or acidic compounds such as phosphoric acid or sulfuric acid. Foaming can be controlled by employing antifoams such as, for example, fatty acid polyglycol esters. To maintain the stability of plasmids it is possible to add to the medium suitable substances having a selective effect, for example antibiotics. Aerobic conditions are maintained by introducing oxygen or oxygen-containing gas mixtures such as, for example, ambient air into the culture. The temperature of the culture is normally 20° C. to 45° C. and preferably 25° C. to 40° C. The culture is continued until formation of the desired product is at a maximum. This aim is normally achieved within 10 to 160 hours.

The fermentation broth can then be processed further. The biomass may, according to requirement, be removed completely or partially from the fermentation broth by separation methods such as, for example, centrifugation, filtration, decanting or a combination of these methods or be left completely in said broth. It is advantageous to process the biomass after its separation.

However, the fermentation broth can also be thickened or concentrated without separating the cells, using known methods such as, for example, with the aid of a rotary evaporator, thin-film evaporator, falling-film evaporator, by reverse osmosis or by nanofiltration. Finally, this concentrated fermentation broth can be processed to obtain 1,2-dehydroreticuline or (R)-reticuline present therein.

According to a further aspect of the invention there is provided the use of a gene encoded by a nucleic acid molecule comprising the nucleotide sequence set forth in SEQ ID NO: 4, 5, 6 or 9, or a nucleic acid molecule the complementary strand of which hybridizes under stringent hybridization conditions to the nucleotide sequence set forth in SEQ ID NO: 4, 5, 6 or 9 and encodes a polypeptide according to the invention as a means to identify a locus wherein said locus is associated with altered expression or activity of a cytochrome P450 or oxidoreductase.

In an aspect of the invention said nucleic acid molecule is at least 55%, 60%, 65%, 70%, 75%, 80%, 90%, 91%, 92%, 93%, 94%, 95%, 96%, 97%, 98% or 99% identical to the nucleotide sequence set forth in SEQ ID NO: 29 over the full nucleotide sequence.

In a preferred embodiment of the invention said nucleic acid molecule comprises or consists of the nucleotide sequence set forth in SEQ ID NO: 29.

In one aspect of the invention said nucleic acid molecule is at least 55%, 60%, 65%, 70%, 75%, 80%, 90%, 91%, 92%, 93%, 94%, 95%, 96%, 97%, 98% or 99% identical to the nucleotide sequence set forth in SEQ ID NO: 10 over the full nucleotide sequence.

In a preferred embodiment of the invention said nucleic acid molecule comprises or consists of the nucleotide sequence set forth in SEQ ID NO: 10.

In one aspect of the invention said nucleic acid molecule is at least 55%, 60%, 65%, 70%, 75%, 80%, 90%, 91%, 92%, 93%, 94%, 95%, 96%, 97%, 98% or 99% identical to the nucleotide sequence set forth in SEQ ID NO: 50 over the full nucleotide sequence.

In a preferred embodiment of the invention said nucleic acid molecule comprises or consists of the nucleotide sequence set forth in SEQ ID NO: 50.

Mutagenesis as a means to induce phenotypic changes in organisms is well known in the art and includes but is not limited to the use of mutagenic agents such as chemical mutagens (e.g. base analogues, deaminating agents, DNA intercalating agents, alkylating agents, transposons, bromine, sodium azide] and physical mutagens [e.g. ionizing radiation, psoralen exposure combined with UV irradiation).

According to a further aspect of the invention there is provided a method to produce a *Papaver* plant that has altered expression of a polypeptide according to the invention comprising the steps of:
 i) mutagenesis of wild-type seed from a *Papaver* plant that does express said polypeptide;
 ii) cultivation of the seed in i) to produce first and subsequent generations of plants;
 iii) obtaining seed from the first generation plant and subsequent generations of plants;
 iv) determining if the seed from said first and subsequent generations of plants has altered nucleotide sequence and/or altered expression of said polypeptide;
 v) obtaining a sample and analysing the nucleic acid sequence of a nucleic acid molecule selected from the group consisting of:

a) a nucleic acid molecule comprising a nucleotide sequence as represented in SEQ ID NO: 4, 5, 6 or 9;
b) a nucleic acid molecule that hybridises to a complementary strand of said nucleic acid molecule in a) under stringent hybridisation conditions and that encodes a polypeptide with cytochrome P450 and/or oxidoreductase polypeptide activity; and optionally
vi) comparing the nucleotide sequence of the nucleic acid molecule in said sample to a nucleotide sequence of a nucleic acid molecule of the original wild-type plant.

In a preferred method of the invention said nucleic acid molecule is at least 55%, 60%, 65%, 70%, 75%, 80%, 90%, 91%, 92%, 93%, 94%, 95%, 96%, 97%, 98% or 99% identical to the nucleotide sequence set forth in SEQ ID NO: 29 over the full nucleotide sequence.

In a preferred method of the invention said nucleic acid molecule comprises or consists of the nucleotide sequence set forth in SEQ ID NO: 29.

In a preferred method of the invention said nucleic acid molecule is at least 55%, 60%, 65%, 70%, 75%, 80%, 90%, 91%, 92%, 93%, 94%, 95%, 96%, 97%, 98% or 99% identical to the nucleotide sequence set forth in SEQ ID NO: 10 over the full nucleotide sequence.

In a preferred method of the invention said nucleic acid molecule comprises or consists of the nucleotide sequence set forth in SEQ ID NO: 10.

In a preferred method of the invention said nucleic acid molecule is at least 55%, 60%, 65%, 70%, 75%, 80%, 90%, 91%, 92%, 93%, 94%, 95%, 96%, 97%, 98% or 99% identical to the nucleotide sequence set forth in SEQ ID NO: 50 over the full nucleotide sequence.

In a preferred method of the invention said nucleic acid molecule comprises or consists of the nucleotide sequence set forth in SEQ ID NO: 50.

In a preferred method of the invention said nucleic acid molecule is analysed by a method comprising the steps of:
i) extracting nucleic acid from said mutated plants;
ii) amplification of a part of said nucleic acid molecule by a polymerase chain reaction;
iii) forming a preparation comprising the amplified nucleic acid and nucleic acid extracted from wild-type seed to form heteroduplex nucleic acid;
iv) incubating said preparation with a single stranded nuclease that cuts at a region of heteroduplex nucleic acid to identify the mismatch in said heteroduplex; and
v) determining the site of the mismatch in said nucleic acid heteroduplex.

In a preferred method of the invention said nucleic acid molecule is at least 55%, 60%, 65%, 70%, 75%, 80%, 90%, 91%, 92%, 93%, 94%, 95%, 96%, 97%, 98% or 99% identical to the nucleotide sequence set forth in SEQ ID NO: 29 over the full nucleotide sequence.

In a preferred method of the invention said nucleic acid molecule comprises or consists of a nucleotide sequence set forth in SEQ ID NO: 29.

In a preferred method of the invention said nucleic acid molecule is at least 55%, 60%, 65%, 70%, 75%, 80%, 90%, 91%, 92%, 93%, 94%, 95%, 96%, 97%, 98% or 99% identical to the nucleotide sequence set forth in SEQ ID NO: 10 over the full nucleotide sequence.

In a preferred method of the invention said nucleic acid molecule comprises or consists of the nucleotide sequence set forth in SEQ ID NO: 10.

In a preferred method of the invention said nucleic acid molecule is at least 55%, 60%, 65%, 70%, 75%, 80%, 90%, 91%, 92%, 93%, 94%, 95%, 96%, 97%, 98% or 99% identical to the nucleotide sequence set forth in SEQ ID NO: 50 over the full nucleotide sequence.

In a preferred method of the invention said nucleic acid molecule comprises or consists of the nucleotide sequence set forth in SEQ ID NO: 50.

In a preferred method of the invention said nucleic acid molecule is at least 55%, 60%, 65%, 70%, 75%, 80%, 90%, 91%, 92%, 93%, 94%, 95%, 96%, 97%, 98% or 99% identical to the nucleotide sequence set forth in SEQ ID NO: 50 over the full nucleotide sequence.

In a preferred method of the invention said nucleic acid molecule comprises or consists of the nucleotide sequence set forth in SEQ ID NO: 50.

In a preferred method of the invention said *Papaver* plant has enhanced polypeptide expression and/or activity.

In a preferred method of the invention said *Papaver* plant has reduced or abrogated polypeptide expression and/or activity.

In a preferred method of the invention said *Papaver* plant is *Papaver somniferum, P. setigerum, P. bracteatum, P. orientale, P. pseudo-orientale, P. lasiothrix, P. cylindricum, P. fugax, P. triniifolium.*

According to a further aspect of the invention there is provided a plant obtained by the method according to the invention.

According to an aspect of the invention there is provided a plant wherein said plant comprises a viral vector that includes all or part of a gene comprising a nucleic acid molecule according to the invention.

In a preferred embodiment of the invention said gene is encoded by a nucleic acid molecule comprising a nucleic acid sequence selected from the group consisting of:
i) a nucleic acid molecule comprising a nucleotide sequence as represented in SEQ ID NO: 4, 5, 6 or 9;
ii) a nucleic acid molecule comprising a nucleotide sequence that hybridises under stringent hybridisation conditions to a nucleic acid molecule in (i) and which encodes a polypeptide according to the invention;
iii) a nucleic acid molecule that encodes a variant polypeptide that varies from a polypeptide comprising the amino acid sequence as represented in SEQ ID NO: 1, 2, 3 or 11.

In a preferred embodiment of the invention said nucleic acid molecule is at least 55%, 60%, 65%, 70%, 75%, 80%, 90%, 91%, 92%, 93%, 94%, 95%, 96%, 97%, 98% or 99% identical to the nucleotide sequence set forth in SEQ ID NO: 29 over the full nucleotide sequence.

In a preferred embodiment of the invention said nucleic acid molecule comprises or consists of a nucleotide sequence as set forth in SEQ ID NO: 29.

In a preferred embodiment of the invention said nucleic acid molecule is at least 55%, 60%, 65%, 70%, 75%, 80%, 90%, 91%, 92%, 93%, 94%, 95%, 96%, 97%, 98% or 99% identical to the nucleotide sequence set forth in SEQ ID NO: 10 over the full nucleotide sequence.

In a preferred embodiment of the invention said nucleic acid molecule comprises or consists of the nucleotide sequence set forth in SEQ ID NO: 10.

In a preferred embodiment of the invention said nucleic acid molecule is at least 55%, 60%, 65%, 70%, 75%, 80%, 90%, 91%, 92%, 93%, 94%, 95%, 96%, 97%, 98% or 99% identical to the nucleotide sequence set forth in SEQ ID NO: 50 over the full nucleotide sequence.

In a preferred embodiment of the invention said nucleic acid molecule comprises or consists of the nucleotide sequence set forth in SEQ ID NO: 50.

According to a further aspect of the invention there is provided a viral vector comprising all or part of a nucleic acid molecule according to the invention.

According to an aspect of the invention there is provided the use of a viral vector according to the invention in viral induced gene silencing in a plant.

In a preferred embodiment of the invention said plant is from the genus *Papaver*, preferably *Papaver somniferum, P. setigerum, P. bracteatum, P. orientale, P. pseudo-orientale, P. lasiothrix, P. cylindricum, P. fugax, P. triniifolium.*

Virus induced gene silencing [VIGS] is known in the art and exploits a RNA mediated antiviral defence mechanism. In plants that are infected with an unmodified virus a defence mechanism is induced that specifically targets the viral genome. However, viral vectors which are engineered to include nucleic acid molecules derived from host plant genes also induce specific inhibition of viral vector expression and additionally target host mRNA. This allows gene specific gene silencing without genetic modification of the plant genome and is essentially a non-transgenic modification.

Throughout the description and claims of this specification, the words "comprise" and "contain" and variations of the words, for example "comprising" and "comprises", means "including but not limited to", and is not intended to (and does not) exclude other moieties, additives, components, integers or steps. "Consisting essentially" means having the essential integers but including integers which do not materially affect the function of the essential integers.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF SUMMARY OF THE DRAWINGS

An embodiment of the invention will now be described by example only and with reference to the following figures and tables:

FIGS. 5A-5E Characterization of opium poppy mutants disrupted in the conversion of (S)- to (R)-reticuline. (A) Schematic overview of benzylisoquinoline alkaloid (BIA) metabolism depicting the central role of reticuline epimerization. (B) Position of the storr-1, storr-2 and storr-3 mutations in the predicted fusion protein. (C) Mean ±SD capsule reticuline content in High Morphine 2 (HM2=MORPHINE CVS1) wild type and storr mutants (HM2 n=5, storr-1 n=12, storr-2 n=17, storr-3 n=15). Reticuline content was verified as >99.2% (S)-reticuline in all mutants by chiral HPLC (Table 8). (D) 1,2-dehydroreticuline. (E) All compounds >1% total alkaloids (n=10) identified with minor peaks (n=379) grouped as "Other";

SEQ ID NO SUMMARY

Figure 1:
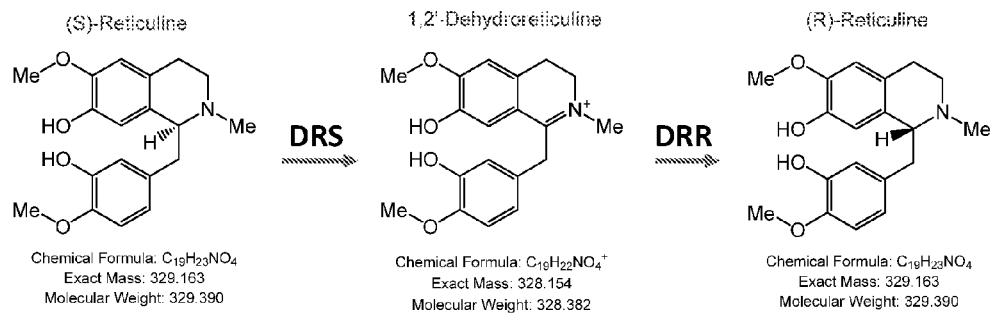
FIG. 1 illustrates the two-step conversion of (S)-reticuline to (R)-reticuline via 1,2-dehydroreticuline discussed in the field (Ziegler et al. (2009) Phytochem. 70 (15-16):1696-1707; Ziegler and Facchini (2008) Annu. Rev. Plant Biol. 59: 735-69; Hirata et al. (2004) Phytochem. 65: 1039-1046)); De-Eknamkul and Zenk (1992) Phytochem. 31, 813-821.

SEQ ID NO 1: CYP450/oxidoreductase fusion protein amino acid sequence
SEQ ID NO 2: CYP450: 1-568(580) amino acid sequence. Amino acids 1-580 include a 12 amino acid long peptide linker (SEQ ID NO: 7). Amino acids 1-568 refer to the sequence without the peptide linker.
SEQ ID NO 3: oxidoreductase amino acid sequence
SEQ ID NO 4: CYP450/oxidoreductase cDNA nucleotide sequence
SEQ ID NO 5: CYP450 nucleotide sequence
SEQ ID NO 6: oxidoreductase A nucleotide sequence
SEQ ID NO 7: peptide linker amino acid sequence
SEQ ID NO 8: nucleotide sequence encoding peptide linker
SEQ ID NO 9: oxidoreductase B genomic nucleotide sequence (Exon 1: nucleotides 35-351; Exon 2: nucleotides 482-725, Exon 3: nucleotides 834-1013, Exon 4: nucleotides 1135-1359)
SEQ ID NO 10: oxidoreductase B nucleotide coding sequence
SEQ ID NO 11: oxidoreductase B amino acid sequence
SEQ ID NO 29: CYP450/oxidoreductase cDNA nucleotide sequence coding region
SEQ ID NO 30: codon optimized PsCPR
SEQ ID NO 31: codon optimized STORR (CYP82Y2-oxidoreductase)
SEQ ID NO 32: codon optimized CYP82Y2 module
SEQ ID NO 33: codon optimized oxidoreductase (oxidoreductase) module
SEQ ID NO 50: oxidoreductase A nucleotide coding sequence
SEQ ID NO 51: PsCPR nucleotide coding sequence [nucleotide sequence 124 to 2175]
Nucleotide sequence SEQ ID NO: 4, 5, 6, 8, 10, 29, 50 and 51 are cDNA.

Materials & Methods
Generation of EST Libraries by Pyrosequencing
A) RNA Extraction and Library Preparation Material was harvested from stems and capsules at two developmental stages from four poppy cultivars. RNA was prepared individually from five plants per cultivar, developmental stage and organ. The harvested material was ground in liquid nitrogen using a mortar and pestle. RNA was isolated from the ground stem or capsule preparations as previously described (Chang et al., 1993, Plant Mol. Biol. Rep. 11: 113-116) with slight modifications (three extractions with chloroform:isoamylalcohol, RNA precipitation with Lithium chloride at −20° C. overnight). RNA was quantified spectrophotometrically before pooling equal amounts of RNA from five plants per cultivar, stage and organ. The pooled samples underwent a final purification step using an RNeasy Plus MicroKit (Qiagen, Crawley, UK) to remove any remaining genomic DNA from the preparations. RNA was typically eluted in 30-100 μL water. cDNA was prepared using a SMART cDNA Library Construction Kit (Clontech, Saint-Germainen-Laye, France) according to the manufacturer's instructions except that SuperScript II Reverse Transcriptase (Invitrogen, Paisley, UK) was used for first strand synthesis. The CDSIII PCR primer was modified to: (SEQ ID NO 12) 5'-ATT CTA GAT CCR ACA TGT TTT TTT TTT TTT TTT TTT TVN-3' where R=A or G, V=A, C or G; N=A/T or C/G. cDNA was digested with MmeI (New England Biolabs Inc., Hitchin, UK) followed by a final purification using a QIAquick PCR Purification kit (Qiagen, Crawley, UK).

b) cDNA Pyrosequencing

The Roche 454 GS-FLX sequencing platform (Branford, Conn., USA) was used to perform pyrosequencing on cDNA samples prepared from the following materials for each of the four *P. somniferum* cultivars—GSK MORPHINE CVS1, GSK MORPHINE CVS2, GSK NOSCAPINE CVS1 and GSK THEBAINE CVS1.

1. Stem, 1-3 days after petal fall (early harvest)
2. Stem, 4-6 days after petal fall (late harvest)
3. Capsule, 1-3 days after petal fall (early harvest)
4. Capsule, 4-6 days after petal fall (late harvest)

c) Raw Sequence Analysis, Contiguous Sequence Assembly and Annotation

The raw sequence datasets were derived from parallel tagged sequencing on the 454 sequencing platform (Meyer et al., 2008, Nature Prot. 3: 267-278). Primer and tag sequences were first removed from all individual sequence reads. Contiguous sequence assembly was only performed on sequences longer than 40 nucleotides and containing less than 3% unknown (N) residues. These high quality EST sequences were assembled into unique contiguous sequences with the CAP3 Sequence Assembly Program (Huang and Madan, 1999, Genome Res. 9: 868-877), and the resulting contigs were annotated locally using the BLAST2 program (Altschul et al., 1997, Nucleic Acids Res. 25: 3389-3402) against the non-redundant peptide database downloaded from the NCBI.

d) Expression Profiling

To estimate expression levels of the cytochrome P450-oxidoreductase A transcript in the stems and capsules of the various opium poppy cultivars EST reads were mapped against the assembled contiguous sequences. ESTs mapping to the cytochrome P450-oxidoreductase A contig were expressed as RPKM-values (mapped reads per kilobase per million mapped reads) after combining early and late developmental stages per organ and cultivar.

EMS Mutagenesis

Prior to mutagenesis, M0 seeds from *P. somniferum* cultivar GSK MORPHINE CVS1 were soaked in 0.1% (w/v) potassium chloride solution for approximately 24 hours. The seed was then imbibed for three hours with ethyl methanesulfonate (EMS) solution (200 mM EMS in 100 mM sodium hydrogen phosphate buffer, pH 5.0, supplemented with 700 mM dimethyl sulfoxide). The treated M1 seed was washed twice for 15 minutes each with 100 mM sodium thiosulphate solution and then twice for 15 minutes each with distilled water. A volume of 10 mL of the respective solutions was used per 1000 seeds and all steps were carried out on a rocking platform. The washed M1 seed was dried overnight on Whatman 3MM Blotting paper (Whatman/GE Healthcare Life Sciences, Little Chalfont, UK) and sown the following morning on top of a mixture of John Innes no 2 compost, vermiculite and perlite (4:2:1), then covered with a thin layer of compost. Seedlings were transplanted three to four weeks after germination into larger pots and grown in the glasshouse until maturity. Dried capsules were harvested by hand from the M1 population once capsules had dried to approximately 10% moisture on the plant. M2 seed was manually separated from the capsule, providing the M2 seed families that were used in the field-based trials described below.

Field-Based Trials of EMS-Mutagenised Lines

In the 2009/2010 growing season, 2 m long rows of M2 seed lines from the EMS mutagenised population (M0 seeds soaked in 200 mM EMS for 3 hours) were hand sown in the field in Tasmania. Plants were thinned to 75 mm apart, grown, and 4 plants per M2 line were self-pollinated (two immature buds per plant selected) by securing a linen bag over the bud. Open-pollinated rows were harvested at ~11% moisture, and assayed (as described below) for morphine (M), codeine (C), oripavine (O) and thebaine (T) content. Analysis of selected self-pollinated capsules from some M2 plant lines indicated significantly reduced morphinan assays, and significantly higher assays of reticuline. M3 seeds from these capsules were sown in the following growing season in Tasmania to confirm this phenotype in both open-pollinated and selected self-pollinated capsules.

Poppy Straw Analysis of Field-Based Trials

Poppy capsules were harvested from the respective mutant lines by hand once capsules had dried to approximately 10% moisture on the plant. The seed was manually separated from the capsule, and capsule straw material (poppy straw) was then shipped to the GSK extraction facility in Port Fairy, Australia.

The poppy straw samples were ground in a Retsch Model MM400 ball mill into a fine powder. Two gram samples of ground poppy straw (2±0.003 g) were extracted in 50 mL of a 10% acetic acid solution. The extraction suspension was shaken on an orbital shaker at 200 rpm for a minimum of 10 minutes then filtered to provide a clear filtrate. The final filtrate was passed through a 0.22 μm filter prior to analysis.

The solutions were analysed using a Waters Acquity UPLC system (Waters Corporation, Milford, Mass., USA) fitted with a Waters Acquity BEH C18 column, 2.1 mm×100 mm with 1.7 micron packing. The mobile phase used a gradient profile with eluent A consisting of 0.1% Trifluoroacetic acid in deionised water and eluent B consisting of 100% Acetonitrile. The mobile phase gradient conditions used are as listed in Table 1, the gradient curve number as determined using a Waters Empower chromatography software package. The flow rate was 0.6 mL per minute and the column maintained at 45 degrees centigrade. The injection volume was 1 μL injection volume and the alkaloids were detected using a UV detector at 285 nm.

The loss on drying (LOD) of the straw was determined by drying in an oven at 105 degrees centigrade for 16-20 hours.

TABLE 1

Gradient Flow Program

| TIME (minutes) | % Eluent A | % Eluent B | Flow (mL/min) | Curve No |
|---|---|---|---|---|
| 0.00 | 95.0 | 5.0 | 0.60 | INITIAL |
| 0.80 | 90.0 | 10.0 | 0.60 | 6 |
| 3.40 | 75.0 | 25.0 | 0.60 | 3 |
| 3.60 | 95.0 | 5.0 | 0.60 | 6 |
| 4.00 | 95.0 | 5.0 | 0.60 | 11 |

Alkaloid concentrations for morphine, pseudomorphine, codeine, thebaine, oripavine and noscapine were quantified using external standard calibration and the results calculated on a dry weight basis. Reticuline was quantified using the thebaine calibration (assuming the thebaine response) and results calculated on a dry weight basis (% weight relative to thebaine; % WRT).

Typical retention times are as follows:

| Compound | Retention Time (minutes) |
|---|---|
| Morphine | 1.14 |
| Pseudomorphine | 1.26 |
| Codeine | 1.69 |
| Oripavine | 1.80 |
| Reticuline | 2.05 |
| 10-Hydroxythebaine | 2.32 |
| Thebaine | 2.53 |
| Noscapine | 3.16 |

Isolation of the full-length sequence of the cytochrome P450-oxidoreductase A and mutant confirmation

*Papaver somniferum* plants of GSK MORPHINE CVS 1 as well as three high reticuline EMS mutant lines were grown under glasshouse conditions to post-flowering stages (1-6 days after petal fall) and stem segments (2.5-3 cm long) immediately beneath the flowers were harvested and flash frozen in liquid nitrogen.

Total RNA was extracted from the stems using the pine tree RNA extraction method (Chang et al., 1993. Plant Mol. Biol. Rep. 11: 113-116) and further purified using the RNeasy Plus MicroKit (Qiagen, Crawley, UK). RNA quality and purity was checked using the RNA ScreenTape system and analysed with the 2200 TapeStation Software (Agilent Technologies, Wokingham, UK).

Total RNA samples (1 μg) from high reticuline mutants and wild-type lines were treated with RQ1 DNAse (Promega, Southampton, UK) following the manufacturer's instructions. cDNA synthesis was performed using 10 μM oligo dT MW 4500 (Invitrogen/Life technologies, Paisley, UK) and 1 mM dNTP. Reactions were incubated for 5 min at 65° C. to allow annealing of oligonucleotides. First strand synthesis reactions contained 1× First Strand buffer (Invitrogen/Life Technologies), 20 mM DTT, 40 U RNAse out (Invitrogen/Life technologies). Reactions were incubated at 42° C. for 2 min and then 200 U SuperScript II reverse transcriptase (Invitrogen/Life technologies, Paisley, UK) was added followed by a 50 min incubation at 42° C. and heat inactivation at 70° C. for 15 min. Samples were diluted 5× in water and used for gene specific amplifications.

The full-length region encoding the cytochrome P450-oxidoreductase A gene was amplified from the cDNA samples using the primers (SEQ ID NO 13) 5'-GGGTT-GAATCATGGAGCTC-3', (SEQ ID NO 14) 5'-GAAGGGAATGAGATCCGTGAC-3' and the high fidelity Q5® Hot Start High-Fidelity DNA Polymerase (New England Biolabs, Hitchin, UK) according to the guidelines supplied by the manufacturer. Cycling conditions were as follows: 98° C. for 30 s, 35 cycles of 98° C. for 10 s, 64° C. for 30 s, 72° C. for 2.5 min and a final extension at 72° C. for 3 min. The 3 kb-PCR product was then ligated into the pSC-A vector using the Strataclone PCR Cloning Kit (Agilent Technologies, Wokingham, UK) and the individual clones were fully sequenced so that at least 3 clones were obtained from each one of the wild-type and mutant poppy lines. The oxidoreductase part of the transcript was designated oxidoreductase A to distinguish it from oxidoreductase B obtained by sequencing of genomic DNA (see below).

Amplification and Cloning of the Oxidoreductase B Gene from Genomic DNA

The full-length coding region encoding an oxidoreductase gene was amplified from genomic DNA of GSK MORPHINE CVS1 using the primers (SEQ ID NO 15) 5'-GC-CGTGTGTGCAGTCAGCAG-3', (SEQ ID NO:16) 5'-GAAGGGAATGAGATCCGTGAC-3' and Phusion Hot Start II DNA Polymerase (Thermo Scientific) according to the guidelines supplied by the manufacturer. Cycling conditions were as follows: 98° C. for 1 min, 35 cycles of 98° C. for 30 sec, 65° C. for 30 sec, 72° C. for 1 min and a final extension at 72° C. for 10 min. The 2 kb-PCR product was then ligated into the pSC-A vector using the StrataClone Blunt PCR Cloning Kit (Agilent Technologies, Wokingham, UK) and 3 individual clones were fully sequenced. The genomic sequence was compared with the oxidoreductase A sequence to delineate exon and intron boarders. The comparison revealed that the oxidoreductase obtained from genomic DNA was very similar (96% identity at the amino acid level) but not identical to oxidoreductase A indicating that a very similar gene exists in opium poppy that was not expressed in the stem or capsule tissue. This gene was designated oxidoreductase B. Based on the exon-introns borders delineated by comparing the genomic sequence of oxidoreductase B with cDNA sequence of oxidoreductase A, the predicted coding region of oxidoreductase B was deduced and used for production of recombinant protein.

Production of Recombinant Oxidoreductase Protein in *E. coli*

The coding sequences of oxidoreductase A and B (Seq ID NO 6 and NO 10, respectively) were codon optimised for expression in *E. coli* and the synthetic genes were cloned into the vector pET28 to yield a recombinant C-terminal 6×-His tagged enzymes (GenScript, Piscataway, N.J., USA). The constructs were transformed into *E. coli* Arctic express strain (Agilent Technologies, Wokingham, UK). Per construct, 3-5 freshly transformed Arctic express *E. coli* colonies were pre-inoculated in 10 mL 2YT medium containing 100 mg/L kanamycin and 20 mg/L gentamycin and incubated at 37° C. overnight. A 5-mL aliquot was used to inoculate 500 mL of the above medium not containing antibiotics and cells were allowed to grow at 30° C. until $OD_{600}$=0.5-0.7. A 1-mL aliquot of the uninduced cells was removed and spun down at 14,000×g and the cell pellet was lysed in SDS-PAGE sample buffer. 1 mM IPTG was added to the culture and then incubated at 20° C. for 24 h. Cells were then harvested following a 5 min spin at 5,000×g and resuspended in 20 mL ice-cold extraction buffer (0.1 M Tris pH 8, 0.3 M NaCl, 0.1% (v/v) Tween 20 and Halt EDTA-free protease inhibitor cocktail (Pierce/Thermoscientific, Cramlington, UK)). Bacterial suspensions were lysed in a French Press at 4° C. using a 25 kpsi disruption cycle (Model TS0.75 KU, Constant Cell Disruption Systems, Daventry, UK). Cell lysates were then spun down at 12,000×g for 20 min at 4° C. and thus fractionated into supernatant (soluble fraction) and pellet.

A 20 mL soluble fraction was filtered through a 0.45 µm syringe filter and the His-tagged proteins were purified using a His Trap Fast Flow crude 5 mL column (GE Healthcare, Little Chalfont, UK) installed in an AKTA Purifier UPC 10 System (GE Healthcare, Sweden) at 4° C. under the following steps: column equilibration in 50 mL 0.1 M Tris pH 8, 0.3 M NaCl, 0.1% (v/v) Tween 20 at 2 mL/min; sample loading at 0.4 mL/min; column wash in 50 mL 0.1 M Tris pH 8, 0.3 M NaCl, 0.1% (v/v) Tween 20, 5 mM imidazole at 2 mL/min; elution in 100 mL 0.1 M Tris pH 8, 0.3 M NaCl, 0.1% (v/v) Tween 20, and a 10-500 mM imidazole gradient at 2 mL/min. Two mL fractions were individually collected. Protein absorbance at 280 nm was monitored throughout the purification procedure. Elution fractions showing absorbance peaks were collected and analysed through SDS-PAGE. Purified proteins (Seq ID NO 3 and 11, respectively) were quantified using Coomassie Plus Protein Assay (Pierce/Thermoscientific, Cramlington, UK) and desalted to remove any inhibitors/interferents using 10 mL Zeba Spin Desalting Columns MWCO 7K, (Pierce/Thermoscientific, Cramlington, UK) pre-equilibrated in 20 mM Potassium Phosphate buffer pH 7.

Western Blot

Soluble protein fraction samples were quantified by Bradford Assay (Coomassie Plus Bradford Assay, Thermoscientific, Cramlington, UK) as described above and 5 µg was separated on a 4-15% polyacrylamide gradient gel (BioRad, Hemel Hempstead, UK) under denaturing conditions. Proteins were transferred onto Protran85 nitrocellulose membranes (Whatman/GE Healthcare, Little Chalfont, UK) by semi-dry blotting in Towbin buffer (250 mM Tris, 200 mM Glycine, 20% (v/v) methanol, pH 8.3) for Western blot analysis. Blots were blocked in 5% (w/v) skimmed milk powder in TBST (100 mM Tris pH7.5, 20 mM NaCl, 0.1% (v/v) Tween 20) overnight at 4° C. under constant shaking, probed with anti-polyHistidine/HRP monoclonal antibodies for 2 h (Sigma, UK) diluted to a titre of 1:5,000 and washed 3×5 min in TBST. Filters were developed using Supersignal West Pico Chemiluminescent Substrate (Thermoscientific/Pierce, UK) and exposed to Hyperfilm ECL (GE Healthcare, Little Chalfont, UK) for 30s.

Enzyme Assays

General reaction set up was carried out as previously described (Lenz & Zenk, 1995, FEBS 233:132-139). Substrates (S)-reticuline, 1,2-dehydroreticuline and coclaurine were purchased from TRC Chemicals (Toronto, Canada) and codeinone was supplied by MacFarlan-Smith (Edinburgh, UK). Assay reactions contained 300 mM NADPH, 5 µg oxidoreductase A or B preparation, 100 mM buffer covering a range of pH values (potassium phosphate pH 6-8, glycine-NaOH pH 9) and 75 µM substrate. Reactions were incubated for 2 h at 37° C. and immediately frozen at –80° C. Reactions were dried down to powder in speedvac GeneVac EZ-2 plus (Ipswich, UK) at 40° C. and resuspended in 100 µL 1:1 Hexane:Ethanol (v/v), 0.1% Diethylamine (v/v).

Chiral HPLC/UV/MS Analysis

Chiral separations were performed following the method previously described (Iwasa et al., 2009, Phytochem 70:198-206) and carried out on a TSP HPLC system equipped with a UV6000 LP detector, a P4000 pump and an AS 3000 autosampler (Thermo Separation Products/Thermoscientific, Waltham, Mass., USA) connected to a mass spectrometer LCQ Classic mass spectrometer (Finnigan Mat, San Jose, Calif., USA). A Lux 5µ Cellulose 3 250×4.6 mm column (Phenomenex, Macclesfield, UK) was used for separations. 10-µL injections were carried out and compounds were separated through isochratic runs performed at 40° C. in a 1:1 Hexane:Ethanol (v/v), 0.1% Diethylamine (v/v) mobile phase with an acquisition time of 20 min. Compound identification was based on retention times monitored through UV (236/254 nm), diode array and total ion count channels as well as mass spectra patterns as compared to that obtained for standards. The data were acquired and analysed using the software Xcalibur 2.0.7 (Thermo Fisher Scientific, Waltham, Mass., USA)

Generation of Segregating F2 Populations

Segregating F2 Populations were Set Up for the Three Mutant Lines Identified in Field Trials.

The F2 population (S-110753) segregating storr-1 resulted from self-pollinating an F1 derived from a cross between storr-1 mutant and GSK NOSCAPINE CVS 1.

The F2 population (S-110756) segregating storr-2 resulted from self-pollinating an F1 derived from a cross between a storr-2 mutant and a morphine cultivar.

The F2 population (S-110744) segregating storr-3 resulted from self-pollinating an F1 derived from a cross between a storr-3 mutant and a morphine cultivar.

Preparation of Genomic DNA from Segregating F2 Populations

Leaf samples (30-50 mg) for DNA extraction were harvested from 4-6 week old plants growing in the glasshouse. Genomic DNA was extracted using the BioSprint 96 Plant kit on the BioSprint 96 Workstation (Qiagen, Crawley, UK) according to the manufacturer's protocol. Extracted DNA was quantified on the NanoDrop™ 8000 Spectrophotometer (Fisher Scientific, Wilmington, Del., USA) and normalized to 10 ng/uL.

Genotyping of Segregating F2 Populations Using KASP Genotyping

KASP genotyping assays were used to genotype the F2 populations described above. To design allele-specific primers, sequences of 50-100 nucleotides around the mutation site (Table 2) were submitted to LGC genomics (Hoddesdon, UK) to order KASP by Design (KBD) primer mix. The sequences of the allele-specific primers as well as the common primer are shown in Table 3.

TABLE 2

DNA sequences used for marker design. The mutations are shown in square brackets, with the specific nucleotide substitution represented as [wild-type allele/mutant allele].

| Mutant allele | Sequences in 5'-3' orientation |
| --- | --- |
| storr-1 (SEQ ID NO 17) | TGGCCTAGTCAAATCTCGAGATGAACTTTTCATCAGTTC CATGCTCTG[G/A]TGCACTGATGCTCACGCTGATCGTG TCCTCCTCGCTCTTCAGAATTCGCTGA |
| storr-2 (SEQ ID NO 18) | TGCTCCAAGCAGGGTGGAACAATTTAAAGAAGCAATTAA TGAAGCATCTTATTTTATGTCGACATCTCCAGTGTCAGA TAATGTTCCAATGCTAGGGTG[G/A]ATTGACCAATTGA CAGGTCTTACGAGAAATATGAAGCACTGCGGAAAGAAAT TAGACTTGGTGGTCGAGAGCATAATTAATGATCATCGTC AAAAGAGACG |
| storr-3 (SEQ ID NO 19) | GTGTATCCTTCTCTTTGGATCTAATGCAACTGGTACTGA CTCGTCTTATTCTCGAGTTTGAAATGAAGTCTCCTAGCG GGAAAGTGGACATGACAGCAACACCA[G/A]GATTAATG AGTTACAAGGTGATCCCCCTTGACATTCTGCTCACCCAT CGTCGCATAAAGCCGTGTGTGCAGTCAGCAGCCTCTGAG AGAGACATGGAGAGTAGTGGTGTACC |

Reactions were carried out in FrameStar® 384 well plates (4Titude® Ltd, Wotton, UK) in a 5.22 μL volume per reaction, with the following reaction components: 2×KASP V4.0 mastermix (LGC genomics), 2.5 μL; KBD primer mix, 0.07 μL; HiDi Formamide (Life Technologies, Paisley, UK), 0.1 μL; HyClone molecular grade water (Thermo Scientific, Hemel Hempstead, UK), 1.5 μL; 10 ng/uL DNA, 1 μL. The plates were centrifuged for 2 minutes at 4500×g, heat-sealed using the Kube™ heat-based plate sealer (LGC genomics), and thermal cycling was carried out in a Hydrocycler™ (LGC genomics) water bath-based thermal cycler, with the following conditions: 94° C. for 15 minutes; 10 cycles: 94° C. for 20 s, 61-55° C. for 60 s (dropping 0.6° C. per cycle); 38 cycles: 94° C. for 20 s, 55° C. for 60 s. The plate reading was carried out on an Applied Biosystems ViiA7 instrument (Life Technologies), for 30 s at 25° C.

TABLE 3

Primer sequences, in 5'-3' orientation.

| Mutant allele | Primer | Primer sequence | Label |
| --- | --- | --- | --- |
| storr-1 | Wild type allele (SEQ ID NO 20) | ATCAGCGTGAGCATCAGTGCAC | Hex |
| | Mutant allele (SEQ ID NO 21) | GATCAGCGTGAGCATCAGTGCAT | FAM |
| | Common primer (SEQ ID NO 22) | TCTCGAGATGAACTTTTCATCAGTTCCAT | |
| storr-2 | Wild type allele (SEQ ID NO 23) | CGTAAGACCTGTCAATTGGTCAATC | FAM |
| | Mutant allele (SEQ ID NO 24) | CGTAAGACCTGTCAATTGGTCAATT | HEX |
| | Common primer (SEQ ID NO 25) | TCCAGTGTCAGATAATGTTCCAATGCTA | |
| storr-3 | Wild type allele (SEQ ID NO 26) | GTGGACATGACAGCAACACCAG | FAM |
| | Mutant allele (SEQ ID NO 27) | AAAGTGGACATGACAGCAACACCAA | HEX |
| | Common primer (SEQ ID NO 28) | CAAGGGGATCACCTTGTAACTCAT | |

Capsule Straw Analysis of a Glasshouse Grown F2 Population Segregating Storr-1.

Capsules from the S-110753 F2 population storr-1 were harvested once capsules had dried to approximately 10% moisture on the plants. Seed was manually separated from the capsule and single capsules were ground to a fine powder in a ball mill (Model MM04, Retsch, Haan, Germany). Samples of ground poppy straw were then weighed accurately to 10±0.1 mg and extracted in 0.5 mL of a 10% (v/v) acetic acid solution with gentle shaking for 1 h at room temperature. Samples were then clarified by centrifugation and a 50 µL subsample diluted 10× in 1% (v/v) acetic acid to give an alkaloid solution in 2% acetic acid for further analysis. All solutions were analyzed as described below (Analysis of benzylisoquinoline alkaloids by LCMS). Likewise, all data analysis was carried out using the R programming language. Putative alkaloid peaks were quantified by their pseudomolecular ion areas using custom scripts. Alkaloids were identified by comparing exact mass and retention time values to those of standards. Where standards were not available, the Bioconductor rcdk package (Smith et al., 2006), Anal. Chem. 78 (3): 779-787) was used to generate pseudomolecular formulae from exact masses within elemental constraints C=1 100, H=1 200, O=0 200, N=0 3 and mass accuracy <5 ppm. The hit with the lowest ppm error within these constraints was used to assign a putative formula.

Leaf Latex Analysis of Glasshouse Grown F2 Populations Segregating Storr-2 and -3, Respectively For the small F2 populations segregating mutant alleles storr-2 and -3, respectively, the alkaloid profile of latex was determined. Latex was collected when the first flower buds emerged (~7 week old plants) from cut petioles, with a single drop dispersed into 500 µL of 10% acetic acid. This was diluted 10× in 1% acetic acid to give an alkaloid solution in 2% acetic acid for further analysis. Alkaloids were analysed as described above for the capsule straw analysis of the glasshouse grown F2 population. The relative content of alkaloids was measured as % peak area relative to total alkaloid peak area.

Cloning and Expression and $^{15}$N-Labeling of Recombinant STORR Protein for Use in Mass Spectrometry Applications A sequence verified wild type STORR cDNA clone was used as template in a PCR-based sub-cloning reaction to provide a protein expression construct with an N-terminal 6HIS tag. Briefly, the mature coding region was amplified from the template plasmid using the polymerase chain reaction and the oligonucleotide forward and reverse primers; d(TCCAGGGACCAGCAATGGAGCTCCAATAT-ATTTCTTATTTTCAAC) (SEQ ID NO 42) and d(TGAG-GAGAAGGCGCGTTAAGCTTCATCATCCCACAAC-TCTTC) (SEQ ID NO 43), respectively. After amplification with KOD Hot-Start DNA polymerase (Novagen), the DNA product was recovered by purification (Qiagen) and combined with the destination vector pETLIC3C (Bonsor D. et al. (2006) Org. Biomol. Chem. 4, 1252-60) using an InFusion cloning reaction (prepared according to the manufacturers recommendations). The resulting construct yielded an N-terminal fusion of a 6HIS tag with a 3C-protease cleavage site (pETLIC3C) under the control of the T7 promoter. The plasmids were transformed in E. coli XL1-Blue (Stratagene) cells for propagation and the cloning was confirmed by DNA sequence analysis.

Routine protein expression was performed in E. coli strain BL21(DE3) (Novagen) by inoculating a single colony from an LB agar plate containing 30 µg/ml kanamycin into 10 ml of LB medium containing 30 µg/ml kanamycin. After 16 hours incubation at 37° C. and 200 rpm, the starter-culture was transferred to 500 ml LB medium containing 30 µg/ml kanamycin and incubated at 37° C., 180 rpm until an OD600 nm of 0.6 AU was obtained. Induction was then achieved by the addition of IPTG to a final concentration of 1 mM before incubation was continued for 4 hours. The induced cells were harvested by centrifugation at 5,000×g, washed (phosphate buffered saline), and the pellet stored at −80° C. until required for protein purification. Protein expression of recombinant $^{15}$N-labeled STORR was performed in E. coli strain ArcticExpress(DE3) (Agilent Technologies) by inoculating a single colony from an LB agar plate containing 1% (w/v) glucose, 30 µg/ml kanamycin into 10 ml of LB medium containing 1% (w/v) glucose, 30 µg/ml kanamycin. After 16 hours incubation at 37° C. and 200 rpm, the starter-culture was centrifuged at 2,700×g for 5 min at 20° C. and the cell pellet resuspended in 750 ml $^{15}$N-labeled M9 minimal media ($^{15}$N ammonium chloride, Cambridge Isotope Laboratories, Inc., Tewksbury, Mass., USA) containing 30 µg/ml kanamycin and incubated at 37° C., 180 rpm until an OD600 nm 0.6Au was obtained. Induction was then achieved by the addition of IPTG to a final concentration of 1 mM before incubation was continued for 4 hours. The induced cells were harvested by centrifugation at 5,000×g, washed (phosphate buffered saline), and the pellet stored at −80° C. until required for protein purification.

The purification of routine and $^{15}$N-labeled protein was performed using the following procedure. Frozen cell pellets were thawed and resuspended in lysis buffer (20 mM Tris-HCl, pH 8.0, 150 mM NaCl, 1 mM DTT containing protease inhibitor cocktail (Roche)) prior to disruption using sonication. A pellet was then recovered by centrifugation at 12,000×g for 10 min at 4° C. and washed twice by resuspending in lysis buffer and centrifuging as above. The washed pellet was then incubated in solubilisation buffer (25 mM Tris-HCl, pH 8.0, 8 M guanidine HCL and 1 mM DTT) by gently mixing at 4° C. for 16 h before the solution was clarified by filtration through a 0.8 µm syringe filter (Sartorius, Epsom, UK). The filtrate was then further purified by loading the extract at a flow rate of 1 ml/min onto $Ni^{2+}$-affinity chromatography using a HiTrap column (GE Healthcare) previously equilibrated in Buffer A (50 mM sodium phosphate, pH 8.0, 300 mM NaCl, 6 M urea and 20 mM imidazole). On completion of sample loading, the column was washed with 10 column volumes (CV) of Buffer A before step elution of specific protein using 5 CV Buffer B (50 mM sodium phosphate, pH 8.0, 300 mM NaCl, 6 M urea and 500 mM imidazole). Fractions containing the STORR expressed protein were confirmed by SDS-PAGE and the protein concentration estimated by $A_{280}$ nm. Analysis of the purified recombinant STORR protein showed full-length expression at the anticipated molecular weight of 103 kDa. The identity of this protein as STORR was confirmed by tryptic digestion and peptide mapping. Likewise, a second product at approximately 40 kDa was confirmed to be an N-terminal fragment of the CYP82Y2 module of the STORR protein. For the relative quantification of the native STORR protein in opium poppy stem extracts only the full length $^{15}$N-labeled recombinant STORR protein was used.

Preparation of Crude Protein Extracts from Stems of Wild Type High Morphine Cultivar HM2 (=High Morphine CVS1)

Stem tissue from just below the flower was harvested from HM2 wild type plants shortly after onset of anthesis. The tissue samples were immediately frozen in liquid nitrogen and stored at −80° C. until extraction. Stem samples from five plants were ground together in liquid nitrogen to a fine powder with a mortar and pestle. 200 mg of tissue powder was extracted with 300 µL of 1.5× cracking buffer (preparation of 5× cracking buffer: 1 mL 0.5 M Tris-HCl, pH 6.8, 1.6 mL glycerol, 1.6 mL 10% (w/v) SDS, 0.4 mL 2-mercaptoethanol, 0.4 mL 5% (w/v) bromophenol blue, 3 mL H$_2$O). The samples were vortexed thoroughly until a homogeneous suspension was achieved. The suspension was incubated for 5 min at 95° C., vortexed for 1 min and then centrifuged at 16,000×g in a bench top centrifuge. 200 µL of the cleared supernatant was transferred into a fresh tube and used for SDS-PAGE.

SDS-PAGE Separation of Wild Type HM2 Stem Crude Protein Extracts and Recombinant A 40 µL aliquot of each sample was run into a 7 cm NuPAGE Novex 4-12% Bis-Tris gel (Life Technologies) at 200 V until the 25 kDa mass marker (PageRuler Plus, prestained protein ladder—Thermo Scientific, Huntingdon, UK) reached the bottom of the gel. The gel was stained with SafeBLUE protein stain (NBS biologicals) for 1 hour before destaining with ultrapure water for 1 h.

In-Gel Tryptic Digestion

Each gel lane was divided into 15 regions (FIG. 6) before excision to LoBind tubes (Eppendorf, Stevenage, UK), washed twice with 50% (v:v) aqueous acetonitrile containing 25 mM ammonium bicarbonate, reduced with DTT (10 mM) and alkylated with iodoacetamide (50 mM). Following dehydration with acetonitrile, gel pieces were digested with 0.2 µg sequencing-grade, modified porcine trypsin (Promega) at 37° C. overnight. Peptides were extracted from the gel by washing three times with 50% (v:v) aqueous acetonitrile, before drying in a vacuum concentrator and reconstituting in 0.1% (v:v) aqueous trifluoroacetic acid.

LC-MS/MS Peptide Analysis

The tryptic digests were loaded onto a nanoAcquity UPLC system (Waters, Elstree, UK) equipped with a nanoAcquity Symmetry C$_{18}$, 5 µm trap (180 µm×20 mm Waters) and a nanoAcquity HSS T3 1.8 µm C$_{18}$ capillary column (75 µm×250 mm, Waters). The trap wash solvent was 0.1% (v/v) aqueous formic acid and the trapping flow rate was 10 µL/min. The trap was washed for 5 min before switching flow to the capillary column. The separation used a gradient elution of two solvents (solvent A: 0.1% (v/v) formic acid; solvent B: acetonitrile containing 0.1% (v/v) formic acid). The flow rate for the capillary column was 300 nL/min. Column temperature was 60° C. and the gradient profile was linear 2-30% B over 125 min then linear 30-50% B over 5 min. The column was washed with 95% solvent B for 2.5 min, returned to initial conditions and re-equilibrated for 25 min before subsequent injections.

The nanoLC system was interfaced to a maXis HD LC-MS/MS System (Bruker Daltonics, Coventry, UK) with a CaptiveSpray ionisation source (Bruker Daltonics). Positive ESI-MS & MS/MS spectra were acquired using AutoMSMS mode. Instrument control, data acquisition and processing were performed using Compass 1.7 software (microTOF control, Hystar and DataAnalysis, Bruker Daltonics). Instrument settings were: ion spray voltage: 1,450 V, dry gas: 3 L/min, dry gas temperature 150° C., ion acquisition range: m/z 150-2,000, quadrupole low mass: 300 m/z, transfer time: 120 ms, collision RF: 1,400 Vpp, MS spectra rate: 5 Hz, cycle time: 1 s, and MS/MS spectra rate: 5 Hz at 2,500 cts to 20 Hz at 250,000 Hz. The collision energy and isolation width settings were calculated automatically using the AutoMSMS fragmentation table, absolute threshold 200 counts, preferred charge states: 2-4, singly charged ions excluded. A single MS/MS spectrum was acquired for each precursor and former target ions were excluded for 0.8 min unless the precursor intensity increased fourfold.

Relative Quantification of STORR Protein in SDS-PAGE Fractions

Recombinant, $^{15}$N-labeled (heavy) STORR protein was used as an internal standard. An equal amount of a tryptic digest of heavy protein was spiked into the in-gel digest of each SDS-PAGE region, and the spiked regions were analysed by LC-MS/MS as described above. Extracted-ion chromatograms (EIC) were created using DataAnalysis version 4.2 (Bruker Daltonics) for multiply-protonated molecule species of the heavy and light (endogenous) versions of the following STORR peptides:

| Peptide sequence | Predicted sequence position | z | Calculated m/z Light | Heavy |
|---|---|---|---|---|
| TAVLSHQR (SEQ ID NO 44) | 50-57 | 2 | 456.257 | 463.236 |
| YGPIFSFPTGSHR (SEQ ID NO 45) | 90-102 | 3 | 489.246 | 495.228 |
| IVCGFQSGPK (SEQ ID NO 46) | 234-243 | 2 | 546.779 | 552.761 |
| LYPASPVVER (SEQ ID NO 47) | 433-442 | 2 | 565.814 | 572.295 |
| IKPCVQSAASER (SEQ ID NO 48) | 568-579 | 3 | 449.235 | 454.885 |
| IGEIPQCR (SEQ ID NO 49) | 869-876 | 2 | 486.750 | 492.732 |

The EIC mass tolerance was 10 mDa and the chromatograms were baseline subtracted and smoothed before integration with the following parameters: signal/noise threshold, 3; intensity threshold, 3%. The ratio of light to heavy peptides (L:H) was calculated from the resulting integrated EIC peak areas. The lowest observable L:H ratio was determined by adding different amounts of a digest of recombinant, light STORR protein plus a constant amount of digested heavy protein to a background consisting of the in-gel digest of an SDS-PAGE fraction that contained no observable STORR peptides; the amount of heavy protein digest was the same as that used to spike the fractions as described above. Confident detection of light STORR peptides was observed at L:H ratios ≥0.01.

Reticuline Standards and Isolation of (S)-Reticuline for Enzymatic Assays (R)-reticuline was obtained from Santa Cruz Biotechnology (Dallas, Tex.) and prepared as a 10 mM stock solution in methanol+0.1% acetic acid. 1,2-dehydroreticuline was obtained from US Biologicals (Salem, Mass., USA) and prepared as a 10 mM stock solution in DMSO. (S)-reticuline was prepared from a mutant poppy line known to contain a high content of (S)-reticuline. The poppy capsule was deseeded to produce poppy straw which was then ground to a fine powder using a Retsch (Haan, Germany) SM300 cutting mill at 2600 rpm with a ≤1 mm screen. The milled straw was then extracted using a four stage solid-liquid counter-current method. Four batches of 50 g poppy straw and 3.5 g calcium oxide were prepared. To the first batch, 500 mL of water was added and the resulting slurry was stirred at room temperature for 25-35 min. The slurry was filtered and 200 mL of the aqueous extract was removed and added to the second batch of straw and the volume brought up to 500 mL with water. The process was repeated such that each batch of straw had been extracted four times. The four 200 mL extracts were then combined to make 800 mL of aqueous alkaloid rich extract at pH 12.3. Sodium carbonate (25 g) was then added to precipitate calcium carbonate. After 15 min of stirring, the extract was filtered through Celite filter aid. The pH was then adjusted to 3-4 using 10% v/v sulphuric acid and the solution filtered through Celite. The extract was adjusted to pH 9.2 with 10% v/v sodium hydroxide and extracted three times with 200 mL of dichloromethane and the solvent was removed by rotary evaporation. The extract was then dissolved in 2% methanol, 1% acetic acid and purified by reverse phase (C18) silica gel flash chromatography using a 2% to 50% methanol in 1% acetic acid gradient. The (S)-reticuline containing fractions were then dried in a speedvac at room temperature, and used to prepare stock solutions at 10 mM in methanol+0.1% acetic acid.

Heterologous Protein Expression in *Saccharomyces cerevisiae*

Genscript created synthetic DNA sequences were created for PsCPR [Genbank accession AAC05021, (Rosco A. et al. (1997) Arch. Biochem. Biophys. 348, 369-77), the full length STORR (CYP82Y2-Oxidoreductatse ("Oxired")) protein, the N-terminal CYP82Y2 module and C-terminal oxidoreductase (Oxidoreductase) module, that were codon optimised for expression is *Saccharomyces cerevisiae*. The codon-optimized sequences are provided with the SEQ ID NO 30-33.

The codon optimized genes were then amplified by PCR using the following primers which incorporate a restrictions site and 5'-AAAA-3' Kozak sequences preceding the start codon:

Defined (SD) medium composed of 2% carbon source, 0.5% ammonium sulfate, 1.7 g L$^{-1}$ yeast nitrogen base (without amino acids and ammonium sulfate) and 1.92 g L$^{-1}$ or tryptophan drop-out supplement (Sigma-Aldrich, Gillingham, UK). Cultures grown using glucose as a carbon source were used to inoculate 200 ml cultures with raffinose as a carbon source to an OD 600 nm of 0.10 in 1 L conical flasks. These were grown at 30° C., 250 rpm, and at and OD 600 nm of 1.8 to 2.2, 20 mL of 20% galactose was added to induce expression on the plasmid-borne transgenes. After a further 16 hours of cultivation, the yeast cells were harvested by centrifugation at 2,000 g for 10 min. The yeast cells were then washed once with 50 mL of water, then suspended in 2 mL of extraction buffer containing 50 mM Bis-tris propane (pH 8.0), 1.2 M sorbitol, 100 mM NaCl, 1 mM EDTA, 1 mM DTT and 1/250 dilution of protease inhibitor cocktail (Sigma-Aldrich P8215). Soluble and microsomal preparations were then prepared as described previously (King A. et al. (2007) Planta 226, 381-94).

Enzyme Assays

Enzymes assays were set up in 250 μL volumes containing final concentrations of 50 mM Bis-tris propane buffer, 1 mM NADPH and 100 μM of substrate. The assays were started by the addition of 50 μL of 2 mg mL$^{-1}$ soluble or microsomal extract, and incubated at 37° C. for 3 hours. After this time, 50 μL of the extract was removed and quenched by the additional of 50 μL of methanol+1% acetic acid containing 100 mM noscapine as an internal standard. The reaction was then centrifuged at 20,000×g for 2 min, and the supernatant recovered for analysis of 1,2-dehydroreticuline and (R/S)-reticuline content (i.e., non-chiral method). The remaining 200 μL of assay was used for chiral analysis. The reaction was quenched by the addition of 0.5

| Primer name | Target | Sequence |
| --- | --- | --- |
| CPR_XhoI_F (SEQ ID 34) | Codon optimized cytochrome P450 reductase (CPR) | 5'-AAAAGGATCCAAAAATGGGTTCAAACAACTTAGCCAACTC-3' |
| CPR_BamHI_R (SEQ ID 35) | | 5'-AAAACTCGAGTTACCAAACATCTCTCAAATATCTTTCTTC-3' |
| CYP82X-Oxidoreductase_NotI_F (SEQ ID 36) | Codon optimized full-length CYP82Y2-Oxidoreductasefusion protein | 5'-AAAAGCGGCCGCAAAAATGGAATTACAATACATCTCCTACTTTC-3' |
| CYP82X-Oxidoreductase_PacI_R (SEQ ID 37) | | 5'-AAAATTAATTAATTATGCTTCGTCATCCCATAATTC-3' |
| CYP82X_NotI_F (SEQ ID 38) | Codon optimized N-terminal CYP82Y2 module | 5'-AAAAGCGGCCGCAAAAATGGAATTACAATACATTTCTTACTTTC-3' |
| CYP82X_PacI_R (SEQ ID 39) | | 5'-AAAATTAATTAATCTCTTTCAGATGCAGCAC-3' |
| Oxidoreductase_NotI_F (SEQ ID 40) | Codon optimized C-terminal Oxidoreductase module | 5'-AAAAGCGGCCGCAAAAATGGAATCCTCTGGTGTCCCTG-3' |
| Oxidoreductase_PacI_R (SEQ ID 41) | | 5'-AAAATTAATTAATTATGCTTCGTCATCCCACAATTC-3' |

Expression vector pESC-TRP::soloxired was created by digesting the corresponding PCR product with NotI and PacI and inserting this behind the GAL10 promoter of pESC-TRP. pESC-TRP::CPR was created by digesting the corresponding PCR product with BamHI and XhoI and inserting this behind the GAL1 promoter of pESC-TRP. This was then used to created pESC-TRP::CPR::CYP82Y2 and pESC-TRP::CPR::CYP82Y2-Oxidoreductase. These plasmids were then transformed in *S. cerevisiae* G175 (Sorger D. et al. (2004) J. Biol. Chem. 279, 31190-6) using lithium acetate protocol (Geitz R. D. and Woods R. A. (2002) *Methods in Enzymology* 350, 87-96). Yeasts were cultivated in Synthetic M sodium carbonated buffer (pH 10.0). Reticuline was then extracted from the reaction products by three sequential extractions with 400 μL of dichloromethane. The solvent extracts were combined and evaporated to dryness in a speedvac. The extract was then dissolved in 100 μL of 50:50:0.1 hexane/ethanol/diethylamine and analysed by the chiral HPLC method to determine the relative amounts of (R)- and (S)-reticuline.

Analysis of Benzylisoquinoline Alkaloids by LCMS

Poppy capsules were processed and analysed by UPLC-MS and R-scripts as previously described ("the standard method"; (Winzer T. et al. (2012) Science 336, 1704-8)).

Compounds were annotated by generation of empirical formulae from exact masses (<5 ppm mass accuracy) and comparison to authentic standards. Unknowns were annotated by a masstag in the format MxTy, where x is mass and y is retention time in seconds. The standard method did not resolve reticuline epimers, so chiral separation methods were developed specifically for this purpose. These were based on methods described by Iwasa et al. (2009) *Phytochem*. 70, 198-206, and achieved using Lux cellulose 3 columns (Phenomenex, Macclesfield, UK) with isocratic separations employing hexane:ethanol:diethylamine (50:50: 0.1 v/v) as mobile phase. Extracted samples were dried and reconstituted in this solvent prior to analysis. Two separation systems were used; the first used a 250×4.6 mm column with a 5 μm particle size on a TSP HPLC system interfaced to LCQ mass spectrometer operating in positive APCI mode (Thermo Separation Products, Hemel Hempstead, UK). On this system, the injection volume was set to 10 μL, the column temperature to 40° C. and the flow rate to 0.5 mL/min. Under these conditions, (S)- and (R)-reticuline eluted at 10.8 and 14.0 min, respectively. This system was used to analyse reticuline epimers from capsule extracts. A second system with increased sensitivity was used to analyse epimers from in vitro assays. This used a 100×4.6 mm column with a 3 μm particle size on the Waters Acquity UPLC system interfaced to an LTQ-Orbitrap mass spectrometer operating in positive APCI mode described previously (Winzer T. et al. (2012) Science 336, 1704-8). The same separation conditions were used as described for the LCQ system, but with the injection volume reduced to 2 μL. Under these conditions, (S)- and (R)-reticuline eluted at 4.3 and 5.5 min, respectively. 1,2-dehydroreticuline from capsules could not be measured with the chiral methods, but was successfully measured using the standard method. However aliquots from in vitro assays exhibited irreproducible retention times and poor peak shapes for this compound. Measurement of this analyte from in vitro assays was achieved under ion-pairing conditions. For selected 1,2-dehydroreticuline analyses, the UPLC-MS system was fitted with a Luna HST C18(2) column (Phenomenex) with dimensions 50×2 mm and a 2.5 μm particle size. Solvent A was water and solvent B was methanol, both with 0.1% (v/v) trifluoroacetic acid added. Samples were injected in 2 μL and eluted at 37° C. and 0.5 mL/min on the column over the following linear gradient: initial 2 min isocratic 98% A; 2-8 min to 98% B. Under these conditions, 1,2-dehydroreticuline eluted at 4.0 min.

EXAMPLE 1

Figure 2:
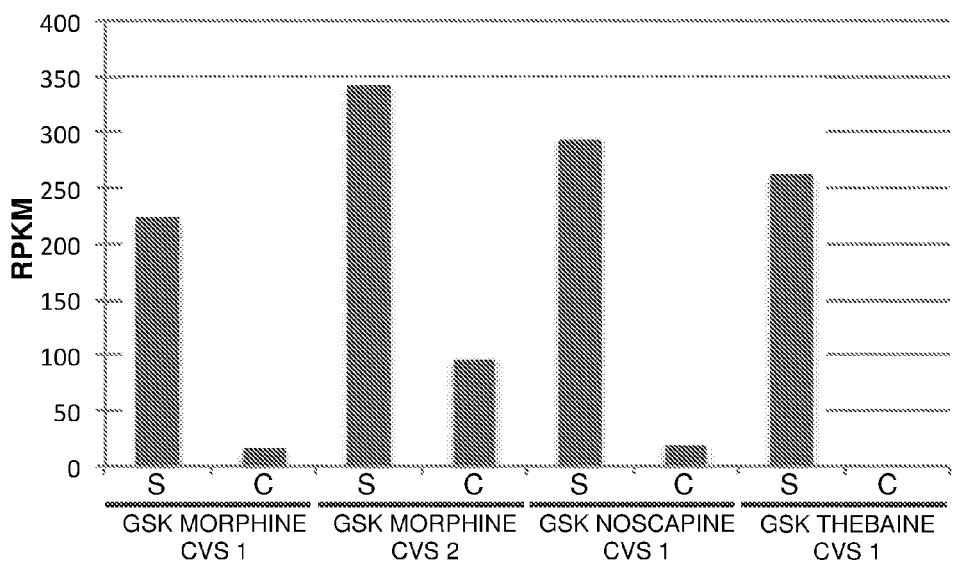
FIG. 2 shows the expression levels of the cytochrome P450-oxidoreductase A transcript in the Expressed Sequence Tag (EST) libraries from stem (S) and capsule (C) samples of opium poppy cultivars GSK MORPHINE CVS 1, MORPHINE CVS 2, Noscapine CVS 1 and THEBAINE CVS 1. EST abundance/expression levels are expressed as mapped reads per kilobase per million mapped reads (RPKM)
Figure 3:
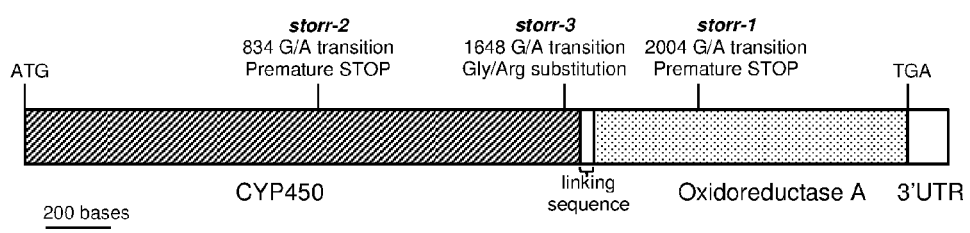
FIG. 3 is a schematic illustration of the CYP450-oxidoreductase A transcript represented by sequence ID No. 4. The nucleotide change and base position of the three mutations identified in high reticuline mutant lines are indicated.

EST library analysis from stem and capsule samples of opium poppy cultivars GSK MORPHINE CVS 1, MORPHINE CVS 2, Noscapine CVS 1 and THEBAINE CVS 1, revealed a contig comprising a cytochrome P450 linked to an oxidoreductase. Analysis of the ESTs mapping to this cytochrome P450 and the oxidoreductase showed that the transcript is expressed in stems and capsules of all cultivars except THEBAINE CVS 1 where corresponding ESTs were only found in the stem library (FIG. 2). Amplification and sequencing from cDNA obtained from stem tissue of MORPHINE CVS 1 confirmed that both genes are transcriptionally fused in the same reading frame. (Sequence ID NO 4, FIG. 3). The corresponding genetic locus was designated 'Storr' for '(S)- to (R)-reticuline'.

EXAMPLE 2

High (S)-reticuline mutant lines identified by forward screening of an EMS mutagenised M2 population contain mutations in the cytochrome P450 or oxidoreductase A part of the transcript.

Three high reticuline mutant lines were identified in a field trials of EMS-mutagenised M2 seed lines, designated mutant line 1, 2 and 3. Analysis of selected self-pollinated capsules of the three M2 mutant lines indicated significantly reduced morphinan content, and significantly higher amount of reticuline (Table 4). M3 seeds obtained from these self-pollinated capsules were sown in the following growing season in Tasmania, and the high reticuline/low morphinan phenotype held true in both the open-pollinated capsules as well in selected self-pollinated capsules from within these lines. Sequencing of Storr cDNA clones obtained from stem tissue of these lines revealed that mutant line 1 harboured a G to A transition at base position 2004 with respect to Seq ID NO: 4 introducing a premature STOP codon in the oxidoreductase A part of the transcript (mutant allele storr-1). Mutant line 2 was found to harbour a G to A transition at base position 834 with respect to Seq ID NO: 4 introducing a premature STOP codon in the cytochrome P450 part of the transcript (mutant allele storr-2). Finally, mutant line 3 was found to harbour a G to A transition at base position 1648 with respect to Seq ID NO: 4 leading to the replacement of a glycine for an arginine (mutant allele storr-3).

Table 4

Table 4 shows the content of the main morphinan alkaloids morphine (M), codeine (C), oripavine (O), thebaine (T) as well as reticuline content in the M2 and M3 generation of the high reticuline mutant lines. Data are from open-pollinated capsules (open-poll.) collected from plants grown in a 2 m long row per mutant line and from individual self-pollinated (self-poll.) capsules. M3 seed harvested from self-pollinated M2 capsules exhibiting a high reticuline phenotype were sown in the following season to confirm the phenotype in both open-pollinated and self-pollinated capsules. Commercial GSK MORPHINE cultivars were used as controls. Morphinan alkaloid content is expressed as % capsule dry weight (DVV) whereas reticuline content is expressed relative to thebaine (% weight relative to thebaine, % WRT).

| | | | | % capsule DW | | | | % WRT |
|---|---|---|---|---|---|---|---|---|
| Season | Notes | Line | Data from | M | C | O | T | Reticuline |
| | | | Mutant line 1 | | | | | |
| October 2009 | | Control | open poll. caps | 3.752 | 0.292 | 0.030 | 0.143 | 0.026 |
| | | M2: | open poll. caps | 2.623 | 0.077 | 0.021 | 0.058 | 0.385 |
| | | S-106542 | self poll. cap C | 0.207 | 0.163 | 0.031 | 0.008 | 1.741 |

|  |  |  |  | % capsule DW | | | | % WRT |
| --- | --- | --- | --- | --- | --- | --- | --- | --- |
| Season | Notes | Line | Data from | M | C | O | T | Reticuline |
| November 2010 |  | Control | open poll. caps | 2.296 | 0.074 | 0.016 | 0.095 | 0.031 |
|  | progeny of | M3: | open poll. caps | 0.204 | 0.081 | 0.017 | 0.054 | 0.922 |
|  | S-106542 | MUB 1601 | self poll. cap A | 0.193 | 0.152 | 0.024 | 0.007 | 0.947 |
|  | self- |  | self poll. cap B | 0.252 | 0.055 | 0.026 | 0.009 | 0.554 |
|  | pollinated |  | self poll. cap C | 0.171 | 0.186 | 0.028 | 0.007 | 1.241 |
|  | capsule C |  | self poll. cap D | 0.211 | 0.025 | 0.011 | 0.004 | 0.581 |
|  |  |  | Mutant line 2 | | | | | |
| October 2009 |  | Control | open poll. caps | 3.687 | 0.300 | 0.034 | 0.141 | 0.026 |
|  |  | M2: | open poll. caps | 2.208 | 0.181 | 0.070 | 0.286 | 0.577 |
|  |  | S-105768 | self poll. cap C | 0.179 | 0.026 | 0.018 | 0.001 | 1.744 |
| November 2010 |  | Control | open poll. caps | 2.120 | 0.112 | 0.017 | 0.134 | 0.017 |
|  | progeny of | M3: | open poll. caps | 0.265 | 0.053 | 0.019 | 0.032 | 1.419 |
|  | S-105768 | MUB 1548 | self poll. cap A | 0.166 | 0.174 | 0.024 | 0.013 | 1.386 |
|  | self- |  | self poll. cap B | 0.291 | 0.122 | 0.021 | 0.085 | 1.561 |
|  | pollinated |  | | | | | | |
|  | capsule C |  | | | | | | |
|  |  |  | Mutant line 3 | | | | | |
| October 2009 |  | Control | open poll. caps | 3.369 | 0.330 | 0.024 | 0.194 | 0.047 |
|  |  | M2: | open poll. caps | 1.635 | 0.111 | 0.017 | 0.027 | 1.134 |
|  |  | S-107868 | sell-pollinated capsule A | 0.251 | 0.106 | 0.027 | 0.001 | 2.097 |
| November 2010 |  | Control | open poll. caps | 2.296 | 0.074 | 0.016 | 0.095 | 0.031 |
|  | progeny of | M3: | open poll. caps | 0.252 | 0.048 | 0.014 | 0.022 | 1.446 |
|  | S-107868 | MUB 1605 | self poll. cap A | 0.368 | 0.071 | 0.023 | 0.007 | 2.066 |
|  | self- |  | self poll. cap B | 0.225 | 0.068 | 0.018 | 0.003 | 1.180 |
|  | pollinated |  | self poll. cap C | 0.210 | 0.078 | 0.019 | 0.011 | 1.068 |
|  | capsule A |  | self poll. cap D | 0.301 | 0.042 | 0.019 | 0.004 | 2.193 |

EXAMPLE 3

The storr alleles co-segregate with the high reticuline phenotype providing genetic evidence for a role of the genes in the conversion of (S)- to (R)-reticuline.

A segregating F2 population resulting from self-pollinating an F1 derived from a cross between storr-1 and GSK NOSCAPINE CVS 1 was generated. 55 F2 individuals were assayed for their alkaloid content in dried capsules and genotyped for storr-1 (Table 5). storr-1 strictly co-segregated with elevated reticuline levels. Very high reticuline levels and very low morphinan alkaloid levels were observed in plants homozygous for mutant storr-1 (Table 5).
Table 5

Table 5 summarises the results of the co-segregation analysis of mutant allele storr-1 with the high reticuline phenotype in a segregating F2 population (S-110753) resulting from self-pollinating an F1 derived from a cross between storr-1 and GSK NOSCAPINE CVS 1. 55 F2 individuals were genotyped for the mutant allele 1 and the concentration of the main morphinan alkaloids, morphine (M), codeine (C), oripavine (O), thebaine (T), as well as noscapine (N) and reticuline were determined in dried capsules. Alkaloid levels are expressed as % capsule dry weight (DVV). Mutant allele 1 strictly co-segregated with elevated levels of reticuline. WT=wild type, Het=heterozygous for mutant allele 1, Hom=homozygous for mutant allele 1

TABLE 5

| Mutant allele | F2 population | Genotype | % capsule DW | | | | | |
| --- | --- | --- | --- | --- | --- | --- | --- | --- |
|  |  |  | M | C | O | T | N | Reticuline |
| storr-1 | S-110753 n = 55 | WT n = 12 | 2.66 ± 0.47 | 0.065 ± 0.05 | 0.000 | 0.014 ± 0.02 | 1.80 ± 0.09 | 0.006 ± 0.002 |
|  |  | Het n = 29 | 3.37 ± 0.58 | 0.140 ± 0.08 | 0.005 ± 0.006 | 0.039 ± 0.05 | 0.20 ± 0.09 | 0.063 ± 0.021 |
|  |  | Hom n = 14 | 0.01 ± 0.001 | 0.1 ± 0.03 | 0.000 | 0.000 | 0.000 | 0.89 ± 0.22 |

For mutant alleles 2 and 3 the alkaloid profile of leaf latex of F2 populations (19 F2 individuals each) was determined. Both, storr-2 and storr-3, strictly co-segregated again with elevated reticuline levels and very high reticuline and low morphinan levels were observed in plants homozygous for the respective mutant alleles (Table 6).
Table 6

Table 6 summarises the results of the co-segregation analysis of storr-2 and storr-3 with the high reticuline phenotype in their respective segregating F2 populations (storr-2: S-110756, 15 F2 individuals; storr-3: S-110744, 19 F2 individuals) and leaf latex was analysed for morphine (M), codeine (C), oripavine (O), thebaine (T), as well as reticuline and where applicable noscapine (N). Relative alkaloid levels are expressed % peak area of total latex alkaloid peak area. Both F2 populations resulted from self-pollinating F1 plants derived from crosses between the respective mutant alleles and a morphine cultivar. WT=wild type, Het=heterozygous for respective mutant allele, Hom=homozygous for storr-2 or storr-3, respectively.

| Mutant allele | F2 population | Genotype | Relative % latex peak area | | | | |
|---|---|---|---|---|---|---|---|
| | | | M | C | O | T | Reticuline |
| storr-2 | S-110756 n = 15 | WT n = 6 | 26.0 ± 13.2 | 11.1 ± 5.1 | 1.2 ± 0.8 | 56.1 ± 14.4 | 0.8 ± 0.3 |
| | | Het n = 4 | 10.7 ± 7.0 | 23.2 ± 18.6 | 0.3 ± 0.3 | 40.5 ± 15.1 | 12.3 ± 3.1 |
| | | Hom n = 5 | 0.5 ± 1.0 | 0.1 ± 0.1 | 0.04 ± 0.08 | 0.6 ± 1.2 | 72.5 ± 2.0 |
| storr-3 | S-110744 n = 19 | WT n = 8 | 39.3 ± 11.2 | 24.3 ± 12.4 | 0.8 ± 0.7 | 27.2 ± 10.3 | 0.6 ± 0.3 |
| | | Het n = 4 | 41.3 ± 6.5 | 20.0 ± 10.3 | 0.4 ± 0.3 | 16.0 ± 9.8 | 6.9 ± 1.2 |
| | | Hom n = 7 | 0.2 ± 0.1 | 0.1 ± 0.03 | 0.0 | 0.1 ± 0.04 | 65.1 ± 3.1 |

Taken together, the results from the co-segregation analysis provided genetic evidence for the involvement of cytochrome P450-oxidoreductase A in the epimerisation of (S)- to (R)-reticuline.

EXAMPLE 4

The recombinantly expressed oxidoreductase A part of the Storr transcript converts 1,2 dehydroreticuline to (R)-reticluine.

The activity of the recombinantly expressed oxidoridoreductase A part of the Storr transcript was tested on the following substrates: (S)-reticuline, 1,2-dehydroreticuline, codeinone and coclaurine under pH conditions ranging from 6 to 9 (Table 7). Recombinant expression was carried out in E. coli.

Table 7 shows the activity profiles for recombinant oxidoreductase A and oxidoreductase B. Purified oxidoreductase A and B were assayed in the presence of the substrates (S)-reticuline (not accepted by either of the oxidoreductases as substrate), 1,2-dehydroreticuline (generating (R)-reticuline) and codeinone (generating codeine and neopine, respectively) at pH values between 6 and 9. The respective reaction products were separated through chiral HPLC/UV/MS and quantified using (S)-reticuline and codeine and neopine standards. (R)-reticuline was identified based on parental ion and fragmentation pattern. Measurements are averages of triplicate reactions±standard deviation.

Reactions containing (S)-reticuline or coclaurine showed no transformation of the substrate regardless of the enzyme preparation assayed. In contrast, enzyme assays containing 1,2-dehydroreticuline as a substrate for oxidoreductase A showed high accumulation of the product (R)-reticuline. Accumulation of this product peaked at pH values of 6 and 9 (respectively 0.207 and 0.312 nmol) and dropped to ~0.1 nmol within the pH range 7-8.

At pH 9 recombinant oxidoreductase A also catalysed the conversion of codeinone to codeine. Due to spontaneous interconversion of codeinone to neopinone, two possible products, codeine and neopine, can potentially be formed from the NADPH dependent reduction of the codeinone substrate. Codeine was the only product detected, accumulating exclusively at pH 9.

The enzymatic data show that the oxidoreductase A part of the Storr transcript is capable of catalysing the second step of the epimerisation of (S)- to (R)-reticuline, the conversion of 1,2-dehydroreticuline to (R)-reticuline (FIG. 1, 4 and Table 7) thus supporting and complementing the genetic evidence obtained from the co-segregation analyses.

EXAMPLE 5

Recombinant oxidoreductase B, a close homologue of the oxidoreductase A, also converts 1,2-dehydroreticuline to (R)-reticuline.

Amplification from genomic DNA yielded the sequence of a close homologue (96% amino acid identity) of the oxidoreductase A, designated oxidoreductase B. No ESTs mapping to this gene were found in the stem and capsule libraries suggesting it was not expressed in those tissues.

| Recombinant Oxidoreductase | Substrate in used assay | Expected/ Observed Product | nmol product formation at pH | | | |
|---|---|---|---|---|---|---|
| | | | 6.0 | 7.0 | 8.0 | 9.0 |
| Oxidoreductase A | coclaurine | No product observed | 0.0 | 0.0 | 0.0 | 0.0 |
| | (S)-reticuline | dehydroreticuline | 0.0 | 0.0 | 0.0 | 0.0 |
| | dehydroreticuline | (R)-reticuline | 0.207 ± 0.015 | 0.089 ± 0.038 | 0.092 ± 0.016 | 0.312 ± 0.025 |
| | codeinone | codeine | 0.0 | 0.0 | 0.0 | 0.150 ± 0.069 |
| | | neopine | 0.0 | 0.0 | 0.0 | 0.0 |
| Oxidoreductase B | coclaurine | No product observed | 0.0 | 0.0 | 0.0 | 0.0 |
| | (S)-reticuline | dehydroreticuline | 0.0 | 0.0 | 0.0 | 0.0 |
| | dehydroreticuline | (R)-reticuline | 0.148 ± 0.036 | 0.130 ± 0.021 | 0.164 ± 0.020 | 0.202 ± 0.026 |
| | codeinone | codeine | 0.0 | 0.0 | 0.0 | 0.0 |
| | | neopine | 0.040 ± 0.020 | 0.005 ± 0.001 | 0.016 ± 0.008 | 0.000 |

Oxidoreductase B activity was tested on the following substrates: (S)-reticuline, 1,2-dehydroreticuline, codeinone and coclaurine under pH conditions ranging from 6 to 9 (Table 7). As for oxidoreductase A, reactions containing (S)-reticuline or coclaurine showed no transformation of the substrate whereas 1,2-dehydroreticuline was efficiently converted to (R)-reticuline. In contrast to oxidoreductase A, (R)-reticuline production increased steadily throughout pH values between 6 and 9. Unlike oxidoreductase A, oxidoreductase B did not form codeine from codeinone in an NADPH dependent reduction of this substrate instead showing neopine production within pH values 6 to 8 (FIG. 4, Table 7). These data indicate that despite the high sequence identity shared by oxidoreductase A and B, these reductases have distinct substrate specificity. Regardless of these differences both recombinant oxidoreductases A and B were capable of catalysing the conversion of 1,2-dehydroreticuline to (R)-reticuline.

EXAMPLE 6

Figure 5A:
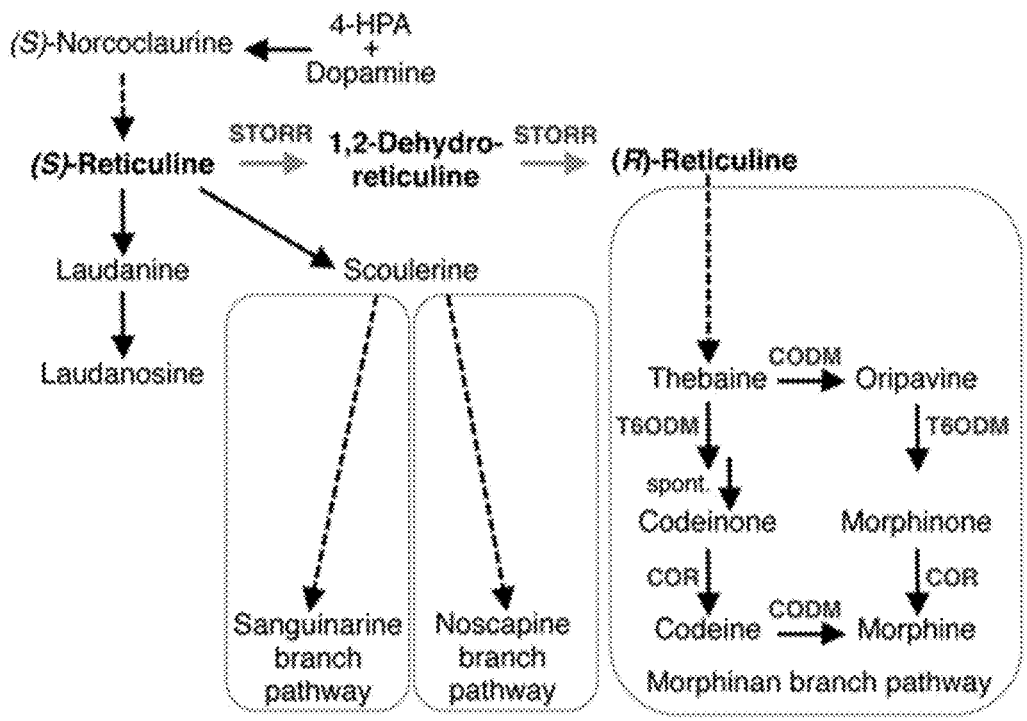

(S)-reticuline is the central intermediate of BIA metabolism (FIG. 5A) and conversion to its R-epimer is believed to occur in a two step process [Iwasa et al. (2009) *Phytochem.* 70, 198-206, Altschul E et al. (1997) *Nucleic Acids Res.* 25, 3389-402,]. The S-epimer is first oxidized to the quaternary, positively charged amine, 1,2-dehydroreticuline, followed by reduction to (R)-reticuline (FIGS. 5A and B). Activities for each step have been reported but the identity of the corresponding proteins has not been established [T. Winzer, et al., *Science* 336, 1704 (2012), Chang et al., *Plant Mol. Biol. Rep.* 11, 113 (1993)]. Adopting a candidate gene approach together with genetic analyses of F2 populations of *P. somniferum* segregating for mutations that are deficient in (S)- to (R)-reticuline conversion has now allowed us to discover a novel fusion protein capable of sequentially catalyzing both steps of the epimerization.

Knocking down codeinone reductase in opium poppy by means of RNAi was previously reported to lead to the unexpected accumulation of (S)-reticuline, which is eight steps upstream of the codeinone reductase substrate (Allen R. S. et al. (2004) *Nat. Biotechnol.* 22, 1559-66).

Figure 5B:
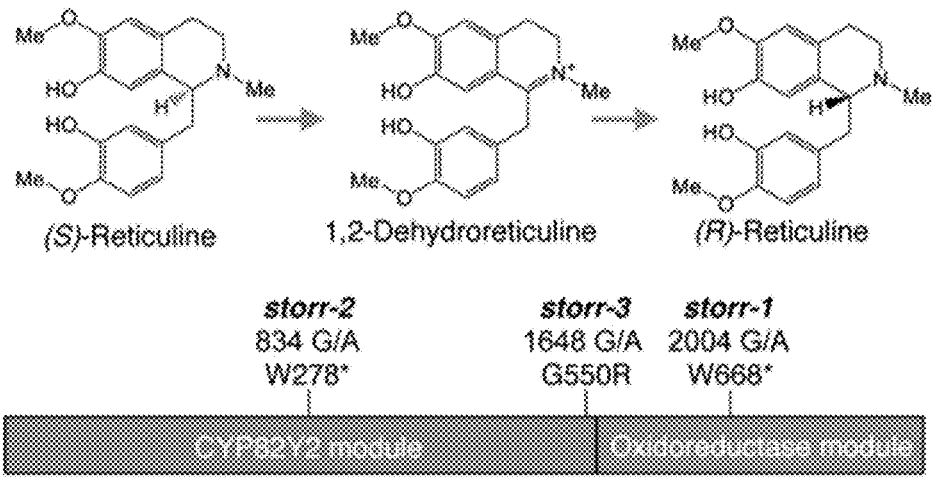

While metabolite channeling was proposed as a possible explanation by the authors, we considered an alternative hypothesis to be off-target co-silencing of a closely related oxidoreductase involved in conversion of (S)- to (R)-reticuline. Using the sequence of the RNAi silencing construct to query an in house EST-library from stem and capsule tissue of opium poppy, we identified a contiguous assembly comprising a cytochrome P450 monooxygenase 3'-linked to an oxidoreductase. Sequencing cDNA clones from opium poppy stems confirmed the in-frame fusion transcript (FIG. 5B). The P450 module has been designated CYP82Y2.

To investigate if the corresponding gene is a candidate for one or both steps in the epimerization of (S)- to (R)-reticuline we sequenced corresponding cDNA clones from three independent mutants identified from an ethyl methanesulfonate mutagenized population of a high morphine cultivar, HM2. All three mutants have lost the ability to produce morphinan alkaloids and instead accumulate high levels of (S)-reticuline as well as the (S)-reticuline-derived alkaloids laudanine and laudanosine (FIGS. 5C and E; Table 8). We found that all three mutant lines carry mutations in the corresponding gene locus (FIG. 5B), which we name STORR ((S)- to (R)-reticuline). The storr-1 allele carries a premature stop codon corresponding to amino acid position W668 in the oxidoreductase module of the predicted fusion protein. Storr-1 plants also accumulate 1,2-dehydroreticuline (FIG. 5D) suggesting that the oxidoreductase module catalyzes the second step of the epimerization, the reduction of 1,2-dehydroreticuline to (R)-reticuline. Storr-2 and storr-3 are both disrupted in the CYP82Y2 module: storr-2 contains a premature stop at codon position W278 and storr-3, a missense mutation causing a G to R substitution at position 550 (FIG. 5B). Unlike dried capsules of storr-1 plants, storr-2 and storr-3 do not accumulate 1,2-dehydroreticuline suggesting that the CYP82Y2 module is responsible for the first epimerization step, the oxidation of (S)-reticuline to 1,2-dehydroreticuline. Segregation analysis of all three mutants confirmed association with the high reticuline mutant phenotype (Table 5 and 6).

TABLE 8

Reticuline epimers in storr mutants. (S)- and (R)-reticuline epimers were resolved by chiral HPLC as described in the methods and the [M + H]+ pseudomolecular ion at m/z 330.17 used to quantify each epimer.

| Mutation | Plant | Peak Areas | | Epimer composition (%) | |
| --- | --- | --- | --- | --- | --- |
| | | (S)-Reticuline | (R)-Reticuline | (S)-Reticuline | (R)-Reticuline |
| storr-1 | 1 | 193951969 | 228894 | 99.88 | 0.12 |
| | 2 | 78769877 | 123097 | 99.84 | 0.16 |
| | 3 | 203130725 | 404437 | 99.80 | 0.20 |
| | 4 | 190190017 | 418958 | 99.78 | 0.22 |
| | 5 | 86282424 | 203210 | 99.77 | 0.23 |
| | 6 | 190124212 | 472528 | 99.75 | 0.25 |
| | 7 | 84069601 | 225883 | 99.73 | 0.27 |
| | 8 | 51997079 | 142964 | 99.73 | 0.27 |
| | 9 | 206014385 | 857515 | 99.59 | 0.41 |
| | 10 | 83810777 | 427471 | 99.49 | 0.51 |
| | 11 | 67295542 | 436143 | 99.36 | 0.64 |
| | 12 | 178730687 | 1308507 | 99.27 | 0.73 |
| | mean | 134530608 | 437467 | 99.67 | 0.33 |
| | SD | 62796474 | 339334 | 0.20 | 0.20 |
| storr-2 | 1 | 520359208 | 251005 | 99.95 | 0.05 |
| | 2 | 370727515 | 241554 | 99.93 | 0.07 |
| | 3 | 108897212 | 79229 | 99.93 | 0.07 |
| | 4 | 154134338 | 126075 | 99.92 | 0.08 |
| | 5 | 289659860 | 238567 | 99.92 | 0.08 |
| | 6 | 114540297 | 114693 | 99.90 | 0.10 |

TABLE 8-continued

Reticuline epimers in storr mutants. (S)- and (R)-reticuline epimers were resolved by chiral HPLC as described in the methods and the [M + H]+ pseudomolecular ion at m/z 330.17 used to quantify each epimer.

| | | Peak Areas | | Epimer composition (%) | |
|---|---|---|---|---|---|
| Mutation | Plant | (S)-Reticuline | (R)-Reticuline | (S)-Reticuline | (R)-Reticuline |
| | 7 | 348519342 | 351006 | 99.90 | 0.10 |
| | 8 | 105038247 | 121516 | 99.88 | 0.12 |
| | 9 | 526976855 | 678815 | 99.87 | 0.13 |
| | 10 | 191487938 | 250501 | 99.87 | 0.13 |
| | 11 | 172226213 | 277557 | 99.84 | 0.16 |
| | 12 | 155844498 | 252069 | 99.84 | 0.16 |
| | 13 | 235645412 | 484513 | 99.79 | 0.21 |
| | 14 | 127590915 | 310733 | 99.76 | 0.24 |
| | 15 | 125500009 | 563301 | 99.55 | 0.45 |
| | 16 | 132278512 | 695276 | 99.48 | 0.52 |
| | 17 | 102549230 | 583898 | 99.43 | 0.57 |
| | mean | 222469153 | 330606 | 99.81 | 0.19 |
| | SD | 140505956 | 198515 | 0.16 | 0.16 |
| storr-3 | 1 | 679690881 | 219435 | 99.97 | 0.03 |
| | 2 | 376570063 | 186977 | 99.95 | 0.05 |
| | 3 | 274171284 | 213661 | 99.92 | 0.08 |
| | 4 | 416724371 | 339626 | 99.92 | 0.08 |
| | 5 | 132344291 | 126899 | 99.90 | 0.10 |
| | 6 | 297068936 | 307636 | 99.90 | 0.10 |
| | 7 | 306622485 | 325573 | 99.89 | 0.11 |
| | 8 | 232824354 | 269834 | 99.88 | 0.12 |
| | 9 | 476240726 | 573810 | 99.88 | 0.12 |
| | 10 | 78300200 | 119211 | 99.85 | 0.15 |
| | 11 | 184559563 | 305635 | 99.83 | 0.17 |
| | 12 | 258032848 | 438033 | 99.83 | 0.17 |
| | 13 | 240979799 | 629862 | 99.74 | 0.26 |
| | 14 | 199605477 | 530382 | 99.73 | 0.27 |
| | 15 | 469154205 | 1352617 | 99.71 | 0.29 |
| | mean | 308192632 | 395946 | 99.86 | 0.14 |
| | SD | 154332995 | 306876 | 0.08 | 0.08 |

EXAMPLE 7

Figure 6:
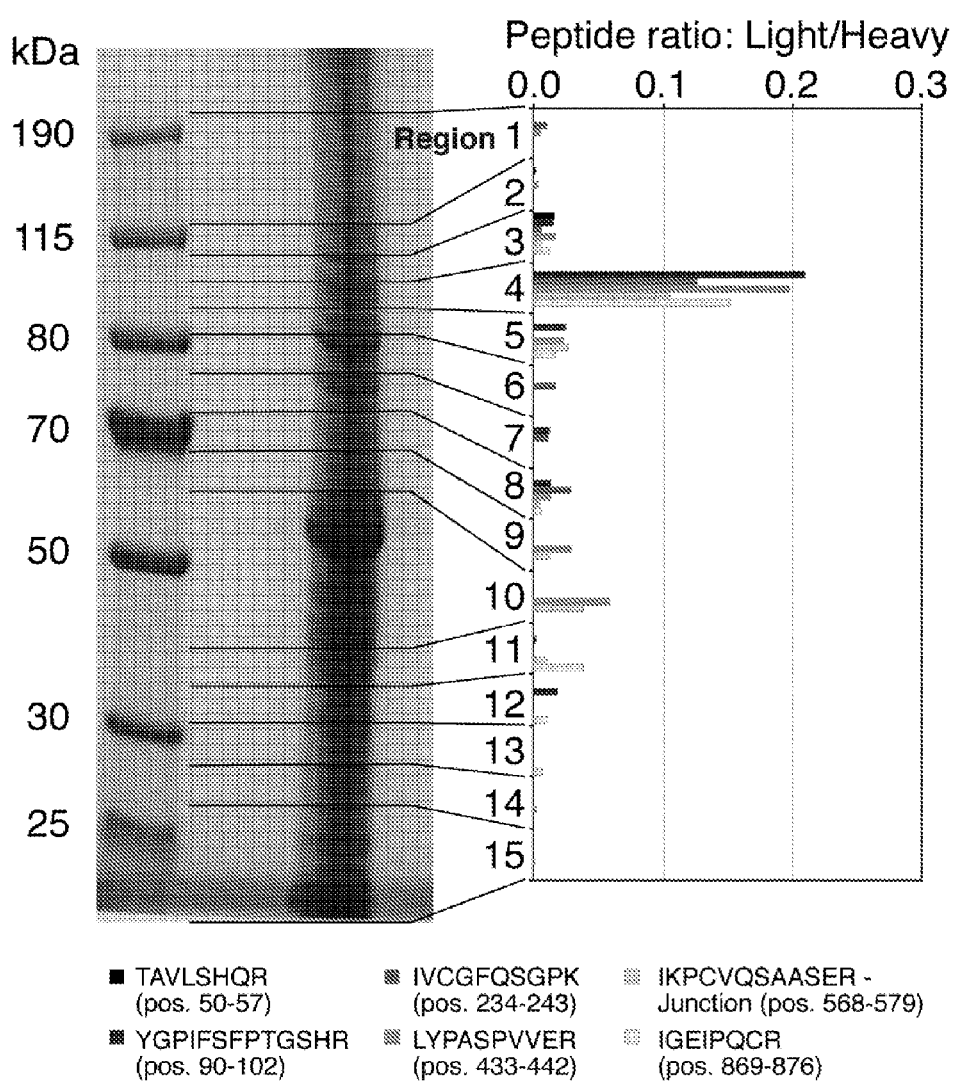
FIG. 6 Size-determination of STORR protein in opium poppy stem extracts. The relative abundance of STORR peptides in gel regions is shown. Total stem protein from wild type cultivar HM2 was separated by SDS-PAGE and the resulting gel divided into 15 size regions as indicated by the horizontal lines to give highest resolution across the size ranges of the predicted STORR fusion protein (100.65 kDa) and the putative individual CYP82Y2-(64.99 kDa) and oxidoreductase-(35.7 kDa) modules. An equal amount of a tryptic digest of 15N-labeled recombinant STORR protein was spiked into the in-gel digest of each SDS-PAGE region prior to mass spectrometry analysis. The ratio of light to heavy peptides from across the STORR protein sequence were determined in each gel region. The highest ratios of light to heavy peptides were found in gel region 4, which covers the predicted size of the full-length STORR protein SEQ ID NO: 1.

The STORR locus is not only transcribed but also translated as a fusion protein. To establish whether the STORR locus is not only transcribed but also translated as a fusion protein, we used a quantitative mass-spectrometry approach following gel fractionation of crude protein extract from HM2 (=High MORPHINE CVS2). Peptides from across the entire STORR protein were found to be most abundant in the gel regions covering the 100.65 kDa predicted size of the fusion protein, confirming this as the in-vivo form (FIG. 6).

EXAMPLE 8

Heterologous expression in yeast demonstrates that the STORR fusion protein is capable of catalyzing the two-step conversion of (S)- to (R)-reticuline with each of is modules performing an individual step in the sequential reaction.

Figure 4A:
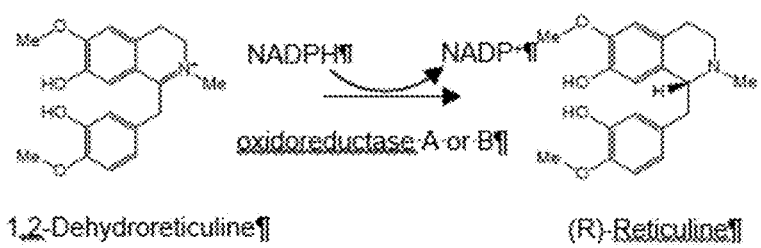
FIGS. 4A-4B summarize the reactions catalysed by oxidoreductase A and B, respectively in *E. coli*. (A) Both oxidoreductases catalyse the NADPH dependent reduction of 1,2-dehydroreticuline into (R)-reticuline, the central precursor of the morphinan biosynthetic pathway. (B) In addition to 1,2-dehydroreticuline, oxidoreductase A also accepts codeinone as a substrate, reducing the ketone functional group to the corresponding alcohols, therefore generating codeine. Due to equilibrium, codeinone is interconverted into neopinone which is in turn accepted by oxidoreductase B and therefore reduced to neopine.
Figure 4B:
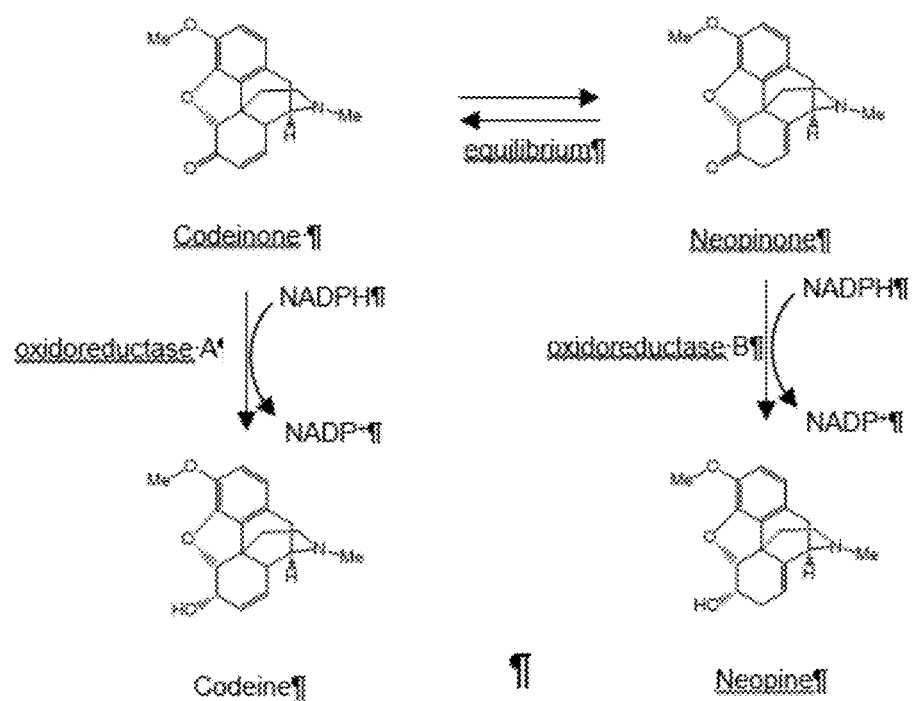
Figure 7A:
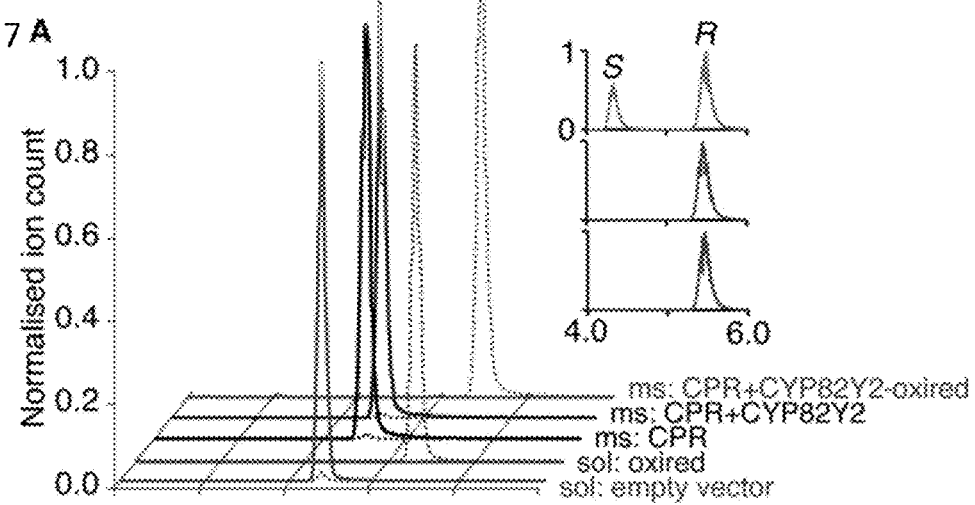
FIGS. 7A-7B: Functional characterization of the STORR fusion protein by heterologous expression in *S. cerevisiae*. (A) HPLC-MS analysis of the in-vitro conversion of dehydroreticuline to (R)-reticuline. Crude soluble (sol) or microsomal (ms) preparations harboring the empty pESC-TRP vector (empty vector), vector containing the oxidoreductase module (oxired), an opium poppy cytochrome P450 reductase (CPR) redox partner (CPR), CPR+CYP82Y2 (CPR+CPY82Y2 ) or CPR+CYP82Y2-oxidoreductase fusion (CPR+CYP82Y2-oxired) were assayed [21]. The solid lines of the HPLC-MS chromatograms show the normalized total ion count at m/z 328 corresponding to 1,2-dehydroreticuline (substrate) whereas the dotted lines show the normalized total ion count at m/z 330 corresponding to reticuline (product). The inset panel shows the chiral analysis of reticuline: The grey trace is for an (S)- and (R)-reticuline standard, the purple and red traces correspond to reticuline derived by activity of the oxidoreductase and CYP82Y2-oxidoreductase fusion respectively. (B) HPLC-MS analysis of the conversion of (S)-reticuline into dehydroreticuline and (R)-reticuline. Crude microsomal preparations obtained from *S. cerevisiae* harboring expression vector pESC-TRP containing CPR only (black), CPR+CYP82Y2 module (blue) or CPR+CYP82Y2-oxidoreductase fusion (red) were assayed. The solid lines of the HPLC-MS chromatograms show the normalized total ion count at m/z 328 corresponding to 1,2-dehydroreticuline, dotted lines show the normalized total ion count at m/z 330 corresponding to reticuline. The inset panel shows the chiral analysis of reticuline, with the same abbreviations as for the main panel.
Figure 7B:
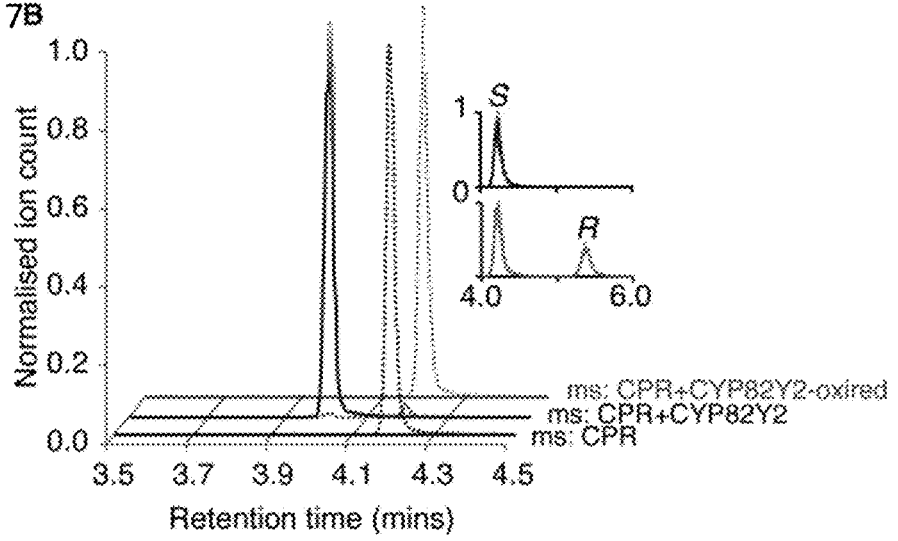

For direct functional characterization the STORR fusion and the separate modules were expressed in *Saccharomyces cerevisiae* and enzyme assays performed on soluble extracts and microsomal preparations (FIG. 7). 1,2-dehydroreticuline is converted to (R)-reticuline with 100% conversion efficiency by both the STORR fusion and the oxidoreductase module but not by the CYP82Y2 module plus redox partner (FIG. 7A) confirming the results obtained with oxidoreductase module recombinantly expressed in *E. coli* (FIG. 4A). In contrast, the CYP82Y2 module plus redox partner catalyzed near-100% conversion of (S)-reticuline to 1,2-dehydroreticuline demonstrating that it acts as a 1,2-dehydroreticuline synthase (FIG. 7B). Microsomal preparations harbouring the entire STORR fusion converted about 20% of the added (S)-reticuline to (R)-reticuline, confirming the bifunctional role of the protein in performing sequential reactions in the epimerization of reticuline.

P450-redox systems where the P450 enzyme is covalently linked to redox partner reductase components are well known in both prokaryotes and lower eukaryotes (Guengerich F. P. and Munro A. W. (2013) J. Biol. Chem. 288, 17065-73). The discovery of the STORR fusion demonstrates that covalent linkage of a P450 to a reductase that is involved in a sequential reaction rather than as a redox partner exists in nature. Other forms of bifunctional P450 fusions with oxygenase/peroxidase, hydrolase and dioxygenase modules have been reported to occur in ascomycetes and all of these also appear to catalyze sequential reactions (Brodhun F. et al. (2009) J. Biol. Chem. 284, 11792-805; Hansen B. G. et al. (2012) Appl. Environ. Microbiol. 78, 4908-13; Hoffmann I. et al. (2014) J. of Lipid Res. 55, 2113-23). STORR represents the first example of a P450 fusion protein from higher eukaryotes. A possible explanation as to why such fusion proteins evolve is that they facilitate efficient channeling of highly unstable, reactive or potentially toxic intermediates. Evidence for efficient substrate channeling in the case of the STORR fusion comes from the observation that microsomal fractions harboring the fusion protein directly convert (S) to (R)-reticuline with no detectable accumulation of 1,2-dehydroreticuline (FIG. 7B).

EXAMPLE 9

A query of the 1K plant transcriptome resource (http://www.onekp.com) identified similar predicted module arrangements in EST collections from two other morphinan producing *Papaver* species, *P. bracteatum* and *P. setigerum* but not in *P. rhoeas* which does not make morphinans (Table 10). We hypothesize that the STORR fusion was the key step in the evolution of the morphinan branch of BIA metabolism. Subsequent to this other enzymes were recruited and adapted, including dioxygenases and reductases, ultimately giving rise to codeine and morphine in *P. somniferum* and *P. setigerum* (S. C. Farrow S. C. and Facchini P. (2013) J. Biol. Chem. 288, 28997-9012). This discovery, along with that of gene clustering (Winzer T. et al. (2012) Science 336, 1704-8) highlights the importance of genome reorganization as well as enzyme modification in the evolution of plant secondary metabolic pathways.

Table 10 Contiguous assemblies encoding predicted P450-oxidoreductase fusions identified in the EST database of the 1K plant transcriptome project. Blast searches were performed with the tblastn algorithm (Altschul F. et al. (1997) Nucleic Acids Res. 25, 3389-402) using STORR protein as query sequence. Contiguous assemblies encoding highly similar predicted STORR homologues were identified in various organs of *P. setigerum* and *P. bracteatum* but not of *P. rhoeas*.

TABLE 10

| Species | Tissue | Contiguous assembly | Amino acid identity of predicted protein |
|---|---|---|---|
| *Papaver somniferum* | leaf | scaffold-BMRX-2007040 | 100% |
| *Papaver setigerum* | flower bud | scaffold-STDO-2019715 | 99% (899 out of 901 residues) |
| *Papaver setigerum* | stem | scaffold-MLPX-2016196 | 99% (899 out of 901 residues) |
| *Papaver setigerum* | developing fruit (capsule) | scaffold-EPRK-2027940 | 99% (899 out of 901 residues) |
| *Papaver bracteatum* | bulb | scaffold-TMWO-2027322 | 95% (854 out of 901 residues) |
| *Papaver bracteatum* | root | scaffold-ZSNV-2027701 | 95% (853 out of 901 residues) |

The invention claimed is:

1. An isolated nucleic acid molecule, comprising:
   i) the cDNA nucleotide sequence of SEQ ID NO: 29 or the nucleotide sequence of SEQ ID NO: 31;
   ii) a nucleotide sequence degenerate as a result of the genetic code to the nucleotide sequence defined in (i) and encoding the amino acid sequence of SEQ ID NO: 1; or
   iii) a nucleic acid molecule comprising at least 95% sequence identity to SEQ ID NO: 31, and which encodes a polypeptide that has cytochrome P450 and/or oxidoreductase activity.

2. The isolated nucleic acid molecule according to claim 1, wherein the isolated nucleic acid molecule
   comprises the cDNA nucleotide sequence of SEQ ID NO: 29; or
   a nucleotide sequence degenerate as a result of the genetic code to the cDNA nucleotide sequence of SEQ ID NO: 29 and encoding the amino acid sequence of SEQ ID NO: 1.

3. The isolated nucleic acid molecule according to claim 1, wherein said nucleic acid molecule comprises:
   i) the nucleotide sequence of SEQ ID NO: 31;
   ii) a nucleotide sequence degenerate as a result of the genetic code to the nucleotide sequence defined in (i) and encoding the amino acid sequence of SEQ ID NO: 1; or
   iii) a nucleic acid molecule comprising at least 98% sequence identity to SEQ ID NO: 31, and which encodes a polypeptide that has cytochrome P450 and/or oxidoreductase activity.

4. The isolated nucleic acid molecule according to claim 3, wherein said isolated nucleic acid molecule
   comprises at least 99% sequence identity to the nucleotide sequence of SEQ ID NO: 31; or
   consists of the nucleotide sequence of SEQ ID NO: 31.

5. A vector comprising the isolated nucleic acid molecule of claim 1, wherein said isolated nucleic acid molecule is operably linked to a promoter sequence.

6. An isolated cell transformed or transfected with the isolated nucleic acid molecule of claim 1.

7. The isolated cell according to claim 6 wherein said cell is a plant cell or a microbial cell.

8. The cell according to claim 7 wherein said microbial cell is a bacterial cell or a yeast cell.

9. The cell according to claim 7, wherein said microbial cell expresses a cytochrome P450 reductase.

10. A plant comprising the plant cell according to claim 7.

11. The plant according to claim 10, wherein said plant is from the genus *Papaver*; preferably *Papaver somniferum*, *P. setigerum*, *P. bracteatum*, *P. orientale*, *P. pseudo-orientale*, *P. lasiothrix*, *P. cylindricum*, *P. fugax*, *P. triniifolium*.

12. A process for producing a polypeptide, comprising:
    i) providing a cell that expresses a polypeptide comprising the amino acid sequence of SEQ ID NO: 1
    ii) culturing said cell under cell culture conditions conducive to the expression of said polypeptide; and optionally
    iii) extracting said polypeptide from the cell or cell culture medium.

13. The process according to claim 12, wherein said cell is a yeast cell.

14. A nucleic acid molecule comprising a transcription cassette wherein said cassette comprises a promoter operably linked to the nucleic acid sequence of SEQ ID NO: 29, wherein both sense and antisense molecules are transcribed from said cassette.

15. The nucleic acid molecule according to claim 14, wherein said nucleic acid molecule is part of a vector adapted for expression in a plant cell.

16. A plant cell transfected with the nucleic acid molecule of claim 14.

17. A process for transforming (S)-reticuline to (R)-reticuline, comprising:
  i) providing the transgenic plant cell according to claim 7;
  ii) cultivating said plant cell to produce a transgenic plant; and optionally
  iii) harvesting said transgenic plant, or part thereof.

18. The process according to claim 17, wherein said harvested plant material is dried and (R)-reticuline is extracted.

19. A viral vector comprising the cDNA nucleic acid molecule according to claim 1.

* * * * *